(12) United States Patent
Chartrand et al.

(10) Patent No.: US 10,092,574 B2
(45) Date of Patent: Oct. 9, 2018

(54) INHIBITORS OF POLYNUCLEOTIDE REPEAT-ASSOCIATED RNA FOCI AND USES THEREOF

(71) Applicant: VALORISATION-RECHERCHE, LIMITED PARTNERSHIP, Montreal (CA)

(72) Inventors: Pascal Chartrand, Montreal (CA); Emmanuelle Querido, Montreal (CA)

(73) Assignee: VALORISATION-RECHERCHE, LIMITED PARTNERSHIP, Montreal (CA)

( * ) Notice: Subject to any disclaimer, the term of this patent is extended or adjusted under 35 U.S.C. 154(b) by 0 days.

(21) Appl. No.: 15/024,169

(22) PCT Filed: Sep. 25, 2013

(86) PCT No.: PCT/CA2013/050730
§ 371 (c)(1),
(2) Date: Mar. 23, 2016

(87) PCT Pub. No.: WO2015/042685
PCT Pub. Date: Apr. 2, 2015

(65) Prior Publication Data
US 2016/0213679 A1 Jul. 28, 2016

(51) Int. Cl.
*A61K 31/55* (2006.01)
*A61K 31/5375* (2006.01)
(Continued)

(52) U.S. Cl.
CPC .............. *A61K 31/55* (2013.01); *A61K 31/18* (2013.01); *A61K 31/352* (2013.01);
(Continued)

(58) Field of Classification Search
None
See application file for complete search history.

(56) References Cited

U.S. PATENT DOCUMENTS 6,340,678 B1 1/2002 Matsuhisa et al.
6,645,990 B2 11/2003 Askew et al.
(Continued)

FOREIGN PATENT DOCUMENTS

AU 2003292720 A1 7/2004
CA 2389681 A1 5/2001
(Continued)

OTHER PUBLICATIONS

Danziger et al., Automated Site-directed Drug Design: A General Algorithm for Knowledge Acquisition about Hydrogen-Bonding Regions at Protein Surfaces, Mar. 22, 1989, The Royal Society, Proceedings of the Royal Society of London.Series B, Biological Sciences, vol. 236, No. 1283, p. 101-113.*
(Continued)

*Primary Examiner* — Kathrien Ann Cruz
*Assistant Examiner* — Andrew P Lee
(74) *Attorney, Agent, or Firm* — Goudreau Gage Dubuc; Alain Dumont

(57) ABSTRACT

Compounds which inhibit the formation and/or accumulation of RNA foci, such as those due to polynucleotide repeats (e.g., trinucleotide repeats) are described herein. Also described herein are uses of such compounds, such as for the inhibition of the formation and accumulation such RNA foci, as well as for the treatment of polynucleotide repeat disorders (e.g., trinucleotide repeat disorders), such as myotonic dystrophy (e.g., DM1). Such compounds include compounds of formula 1, 1a, 1b, 2, 2a and (3) described herein.

22 Claims, 18 Drawing Sheets
Specification includes a Sequence Listing.

(51) Int. Cl.
| | |
|---|---|
| A61K 31/18 | (2006.01) |
| A61K 31/505 | (2006.01) |
| A61K 31/40 | (2006.01) |
| A61K 31/495 | (2006.01) |
| A61K 31/381 | (2006.01) |
| A61K 31/352 | (2006.01) |
| A61K 31/445 | (2006.01) |
| A61K 31/357 | (2006.01) |
| A61K 31/4453 | (2006.01) |
| A61K 31/4406 | (2006.01) |
| A61K 31/454 | (2006.01) |
| A61K 31/415 | (2006.01) |
| A61K 31/4155 | (2006.01) |
| A61K 31/4439 | (2006.01) |
| A61K 31/353 | (2006.01) |

(52) U.S. Cl.
CPC .......... *A61K 31/353* (2013.01); *A61K 31/357* (2013.01); *A61K 31/381* (2013.01); *A61K 31/40* (2013.01); *A61K 31/415* (2013.01); *A61K 31/4155* (2013.01); *A61K 31/445* (2013.01); *A61K 31/4406* (2013.01); *A61K 31/4439* (2013.01); *A61K 31/4453* (2013.01); *A61K 31/454* (2013.01); *A61K 31/495* (2013.01); *A61K 31/505* (2013.01); *A61K 31/5375* (2013.01)

(56) References Cited

U.S. PATENT DOCUMENTS

| | | |
|---|---|---|
| 7,105,538 B2 | 9/2006 | Hennies et al. |
| 7,119,091 B2 | 10/2006 | Habashita et al. |
| 7,271,192 B2 | 9/2007 | Sundermann et al. |
| 7,368,470 B2 | 5/2008 | Sundermann et al. |
| 7,595,311 B2 | 9/2009 | Busch et al. |
| 7,951,815 B2 | 5/2011 | Sundermann et al. |
| 2006/0276511 A1 | 12/2006 | Serrano-Wu et al. |
| 2013/0102606 A1 | 4/2013 | Hwang et al. |
| 2013/0149397 A1 | 6/2013 | Chen et al. |

FOREIGN PATENT DOCUMENTS

| | | |
|---|---|---|
| CA | 2613874 A1 | 1/2007 |
| CA | 2 618 370 | 2/2007 |
| EP | 0367110 A1 | 5/1990 |
| FR | 2924931 B1 | 6/2009 |
| WO | 0035919 A2 | 6/2000 |
| WO | 0102424 A2 | 1/2001 |
| WO | 0132626 A1 | 5/2001 |
| WO | 0136386 A1 | 5/2001 |
| WO | 0187038 A2 | 11/2001 |
| WO | 0190101 A1 | 11/2001 |
| WO | 03037274 A2 | 5/2003 |
| WO | 03037890 A2 | 5/2003 |
| WO | 03099821 A1 | 12/2003 |
| WO | 2004074283 A1 | 9/2004 |
| WO | 2004089415 A2 | 10/2004 |
| WO | 2004089416 A2 | 10/2004 |
| WO | 2004089470 A2 | 10/2004 |
| WO | 2005061462 A2 | 7/2005 |
| WO | 2006002421 A2 | 1/2006 |
| WO | 2007092435 A2 | 8/2007 |
| WO | 2007146122 A2 | 12/2007 |
| WO | 2008011476 A2 | 1/2008 |
| WO | 2008134354 A1 | 11/2008 |
| WO | 2009013211 A2 | 1/2009 |
| WO | 2013062667 A1 | 5/2013 |
| WO | 2013089832 A1 | 6/2013 |
| WO | PCT/CA2013/050730 | 12/2013 |

OTHER PUBLICATIONS

Brook, J. D., McCurrach, M. E., Harley, H. G., Buckler, A. J.Church, D., Aburatani, H., Hunter, K., Stanton, V. P., Thirion, J. P., Hudson, T. et al. (1992). Molecular basis of myotonic dystrophy: expansion of a trinucleotide (CTG) repeat at the 3' end of a transcript encoding a protein kinase family member. Cell 68, 799-808.

Buxton, J., Shelbourne, P., Davies, J., Jones, C., Van Tongeren, T., Aslanidis, C., de Jong, P., Jansen, G., Anvret, M., Riley, B. et al. (1992). Detection of an unstable fragment of DNA specific to individuals with myotonic dystrophy. Nature 355, 547-548.

Charizanis K., Lee K.Y., Batra R., Goodwin M., Zhang C., Yuan Y., Shiue L., Cline M., Scotti M.M., Xia G. et al. (2012). Muscleblind-like 2-mediated alternative splicing in the developing brain and dysregulation in Myotonic Dystrophy. Neuron 75: 437-50.

Daughters, R. S., Tuttle, D. L., Gao, W., Ikeda, Y., Moseley, M. L., Ebner, T. J., Swanson, M. S. and Ranum, L. P. W. (2009). RNA gain-of-function in spinocerebellar ataxia type 8. PLoS Genet. 5, e1000600.

Davis, B. M., McCurrach, M. E., Taneja, K. L., Singer, R. H., and Housman, D. E. (1997) Expansion of a CUG trinucleotide repeat in the 3' untranslated region of myotonic dystrophy protein kinase transcripts results in nuclear retention of transcripts PNAS 94: 7388-7393.

Fardaei, M., Larkin, K., Brook, J.D., and Hamshere, M.G. (2001). In vivo co-localisation of MBNL protein with DMPK expanded-repeat transcripts. Nucleic Acids Research. 29, 2766-2771.

Fu, Y. H., Pizzuti, A., Fenwick, R.G. Jr., King, J., Rajnarayan, S., Dunne, P.W., Dubel, J., Nasser, G.A., Ashizawa, T., de Jong, P., et al. (1992) An unstable triplet repeat in a gene related to myotonic muscular dystrophy. Science 255:1256-1258.

Goers, E.S., Purcell, J., Voelker, R.B., Gates, D.P., and Berglund, J.A. (2010). MBNL1 binds GC motifs embedded in pyrimidines to regulate alternative splicing. Nucleic Acids Research 38, 2467-2484.

Ho T.H., Bundman D., Armstrong Di., Cooper T.A. (2005). Transgenic mice expressing CUG-BP1 reproduce splicing mis-regulation observed in myotonic dystrophy. Hum. Mol. Genet. 14:1539-47.

Jiang et al. (2012). Neuroprotective role of Sirt 1 in mammalian models of Huntingtons's disease through activation of multiple sirt 1 targets. Nature Medicine. 18:153-158.

Jeong et al. (2012). Sirt 1 mediates neuroprotection from mutant huntington by activation of the TORC1 and CREB transcripitional pathway. Nature Medicine. 18:156-165.

Kimura T., Nakamori M., Lueck J.D., Pouliquin P., Aoike F., Fujimura H., Dirksen R.T., Takahashi M.P., Dulhunty A.F., Sakoda S. (2005). Altered mRNA splicing of the skeletal muscle ryanodine receptor and sarcoplasmic/endoplasmic reticulum Ca2+-ATPase in myotonic dystrophy type 1. Hum. Mol. Genet. 14 :2189-2200.

Kuyumcu-Martinez, N. M., Wang, G.-S., and Cooper, T. A. (2007) Increased Steady-State Levels of CUGBP1 in Myotonic Dystrophy 1 Are Due to PKC-Mediated Hyperphosphorylation. Molecular Cell 28, 68-78.

Liquari, CL et al., (2001). Myotonic dystrophy type 2 caused by a CCTG expansion in intron 1 of ZNF9. Science 293, 864-867.

Mahadevan, M., Tsilfidis, C., Sabourin, L., Shutler, G., Amemiya, C., Jansen, G., Neville, C., Narang, M., Barcelo, J., O'Hoy, K. et al. (1992). Myotonic dystrophy mutation: an unstable CTG repeat in the 3 untranslated region of the gene. Science 255, 1253-1255.

Philips, Anne V., Timchenko, Lubov T., and Cooper, Thomas A., Disruption of Splicing Regulated by a CUG-Binding Protein in Myotonic Dystrophy. Science 280 (5364), 737 (1998).

Ranum, L. P. W. and Cooper, T. A. (2006). RNA-mediated neuromuscular disorders. Annu. Rev. Neurosci. 29, 259-277.

Rudnicki, D. D., Holmes, S. E., Lin, M. W., Thornton, C. A., Ross, C. A. and Margolis, R. L. (2007). Huntington's disease-like 2 is associated with CUG repeat-containing RNA foci. Ann. Neurol. 61, 272-282.

Tassone, F., Iwahashi, C. and Hagerman, P. J. (2004). FMR1 RNA within the intranuclear inclusions of fragile X-associated tremor/ataxia syndrome (FXTAS). RNA Biol. 1, 103-105.

(56) References Cited

OTHER PUBLICATIONS

Warf MB, Diegel JV, von Hippel PH., Berglund JA. (2009). The protein factors MBNL1 and U2AF65 bind alternative RNA structures to regulate splicing. Proc Natl Acad Sci USA. Jun 9; 106(23): 9203-8.

Wheeler, T. M., Thornton, C.A. (2007) Myotonic dystrophy: RNA-mediated muscle disease. Curr. Opin. Neural. 20, 572-576.

Wheeler, T. M. (2008) Myotonic Dystrophy: Therapeutic Strategies for the Future. Neurotherapeutics 5, 592-600.

Khanfar et al., Development and characterization of 3-(benzylsulfonamido) benzamides as potent and selective SIRT2 inhibitors, 2014, European Journal of Medicinal Chemistry 76: 414-426.

Extended European Search Report in respect of EP application No. 13894694.2, dated May 19, 2017.

\* cited by examiner

A) Para-amino sulfonamide family compound 15

B) Benzyl Methylthiophene amide family compound 32

| compound | LacZ-145CUG (assay 1) | | | LacZ-145CUG (assay 2) | | | LacZ-5CUG | | |
|---|---|---|---|---|---|---|---|---|---|
| | EC50 (µM) | Conc 1.5 fold (µM) | Max | EC50 (µM) | Conc 2 fold (µM) | Max | EC50 (µM) | Conc 2 fold (µM) | Max |
| 8 | 8,90 | 13,13 | 1,73 | 6,24 | >12.5 | 1,99 | 3,81 | ND | 0,89 |
| 12 | 0,30 | 1,27 | 1,81 | 2,46 | 2,55 | 2,48 | 4,87 | ND | 0,98 |
| 16 | 3,04 | 5,56 | 1,70 | 5,38 | 7,62 | 2,32 | 11,48 | ND | 0,88 |
| 19 | 5,28 | ND | 1,43 | 7,07 | ND | 1,90 | 6,14 | ND | 0,90 |
| 21 | 7,57 | ND | 1,64 | 8,51 | ND | 1,76 | 4,50 | ND | 0,87 |
| 22 | 6,29 | 10,13 | 1,57 | 5,70 | >12.5 | 1,92 | 4,74 | ND | 0,83 |
| 23 | 5,73 | 6,61 | 1,83 | 4,91 | ND | 1,68 | 1,73 | ND | 0,85 |
| 24 | 1,93 | ND | 1,31 | 4,03 | ND | 1,44 | 20,04 | ND | 0,89 |
| 27 | 4,26 | 7,07 | 1,61 | 4,53 | ND | 1,81 | 3,99 | ND | 0,96 |
| 28 | 4,09 | 8,42 | 1,52 | 12,49 | 14,89 | 2,41 | 10,36 | ND | 0,89 |
| 29 | 4,98 | ND | 1,38 | 10,19 | ND | 1,31 | 1,81 | ND | 0,88 |
| 31 | 5,23 | 5,31 | 1,73 | 5,91 | ND | 1,78 | 2,22 | ND | 0,89 |
| 32n | 24,94 | ND | 1,35 | 5,15 | ND | 1,37 | 12,01 | ND | 0,81 |
| 34 | 5,13 | 13,99 | 1,62 | 5,36 | ND | 1,64 | 1,93 | ND | 0,87 |
| 43 | 6,39 | 10,55 | 1,62 | 13,93 | ND | 1,76 | 6,99 | ND | 0,86 |
| 46 | 15,64 | 17,61 | 1,68 | 8,00 | ND | 1,24 | 27,97 | ND | 0,90 |

A) Para-amino sulfonamide family

Active compounds (2<sup>nd</sup> screen)

compound 12 compound 8 compound 19 compound 32n

Compound 24 compound 21   compound 22   compound 23 compound 27   compound 28   compound 29 compound 31   compound 34 compound 16

B) Benzyl Methylthiophene amide family

Active compound (1st screen)

compound 32

Active compounds (2nd screen)

compound 43 compound 46

Compound 102

Compound 196

Compound 214

Compound 195

Compound 213

Compound 215

Compound 216

Compound 217

Compound 218

Compound 219

Compound 220

Compound 221

| Analog | % MBNL2 exon 7 splicing correction | % MBNL1 exon 7 splicing correction | % Serca1 exon 22 splicing correction | Ratio Viable cell number | % Dead cells |
|---|---|---|---|---|---|
| 15 (HIT) | 33% | 30% | 28% | 0,22 | 14,5 |
| 8 | 31% | 21% | 8% | 0,60 | 2,05 |
| 12 | 27% | 26% | 4% | 0,68 | 19,4 |
| 19 | 29% | 19% | 8% | 0,56 | 1,10 |
| 21 | 33% | 24% | 6% | 0,58 | 2,07 |
| 22 | 38% | 25% | 6% | 0,58 | 3,10 |
| 23 | 30% | 21% | 2% | 0,51 | 1,56 |
| 24 | 12% | 9% | 2% | 0,74 | 1,09 |
| 27 | 25% | 21% | 3% | 0,67 | 1,56 |
| 28 | 15% | 13% | 2% | 0,74 | 2,16 |
| 29 | 8% | 3% | 2% | 0,77 | 8,00 |
| 31 | n.d. | n.d. | n.d. | 0,09 | 25,7 |
| 32n | 45% | 35% | 8% | 0,71 | 1,19 |
| 34 | 15% | 8% | 3% | 0,43 | 2,00 |
| 32 (HIT) | 43% | 21% | 4% | 0,79 | 2,05 |
| 43 | 27% | 15% | 2% | 0,65 | 2,53 |
| 46 | 30% | 14% | 7% | 0,85 | 1,85 |

0%: no splicing correction
100%: complete splicing correction

FIG. 10

| Analog | % MBNL2 exon 7 splicing correction | % MBNL1 exon 7 splicing correction | % TNNT2 exon 5 splicing correction | % Serca1 exon 22 splicing correction |
|---|---|---|---|---|
| 8 | 33% | 21% | 9% | 10% |
| 32n | 35% | 28% | 12% | 8% |
| 32 (HIT) | 35% | 19% | 7% | 5% |
| 102 | 38% | 19% | 7% | 3% |
| 195 | 13% | 7% | 1% | -2% |
| 196 | 44% | 34% | 17% | 31% |
| 213 | 9% | 4% | 3% | 4% |
| 214 | 25% | 13% | 3% | 6% |
| 215 | 15% | 5% | -1% | 0% |
| 216 | -1% | 3% | -5% | 0% |
| 217 | 5% | 3% | 0% | -3% |
| 218 | 3% | 1% | -2% | -2% |
| 219 | 4% | 1% | -2% | 0% |
| 220 | 26% | 13% | 5% | 5% |
| 221 | 10% | 3% | -1% | 4% |

0%: no splicing correction
100%: complete splicing correction
Negative: opposite effect

FIG. 11

SEQUENCE LISTING

```
<160> NUMBER OF SEQ ID NOS: 8

<210> SEQ ID NO 1
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 1
acaagtgaca acaccgtaac cg                                                  22

<210> SEQ ID NO 2
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 2
tttggtaaag gatgaagagc acc                                                 23

<210> SEQ ID NO 3
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 3
atgatcttca agctccgggc                                                     20

<210> SEQ ID NO 4
<211> LENGTH: 20
<212> TYPE: DNA
<213> ORGANISM: Artificial Sequence
<220> FEATURE:
<223> OTHER INFORMATION: Synthetic oligonucleotide
```

```
<400> SEQUENCE: 4
cagctctgcc tgaagatgtg                                          20

<210> SEQ ID NO 5
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 5
atagaagagg tggtggaaga gtac                                     24

<210> SEQ ID NO 6
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 6
gtctcagcct ctgcttcagc atcc                                     24

<210> SEQ ID NO 7
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 7
ctgaagcgac tgagtccgcg                                          20

<210> SEQ ID NO 8
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 8
acagtctgta agctttcccc                                          20
```

INHIBITORS OF POLYNUCLEOTIDE REPEAT-ASSOCIATED RNA FOCI AND USES THEREOF

CROSS-REFERENCE TO RELATED APPLICATIONS

The present application is a National Entry Application of PCT application no. PCT/CA2013/050730 filed on Sep. 25, 2013 and published in English under PCT Article 21(2), which is herein incorporated by reference in its entirety.

SEQUENCE LISTING

Pursuant to 37 C.F.R. 1.821(c), a sequence listing is submitted herewith as an ASCII compliant text file named 12810_575-Seq listing_ST25.txt, created on Mar. 10, 2016 and having a size of 2 kilobytes. The content of the aforementioned file is hereby incorporated by reference in its entirety.

TECHNICAL FIELD

The present invention generally relates to polynucleotide repeat disorders such as trinucleotide repeat disorders, and more particularly to compounds and uses thereof such as for the treatment of diseases associated with the presence of polynucleotide repeats, such as myotonic dystrophy.

BACKGROUND ART

Polynucleotide repeat disorders are a set of genetic disorders caused by polynucleotide repeat expansions (typically trinucleotide repeat expansions). The expanded polynucleotide/trinucleotide repeats have been shown to cause the retention of transcripts in the nucleus, where it accumulates in numerous foci (RNA aggregates). More and more RNA aggregates or foci have been identified in different pathologies, for example Myotonic Dystrophy type 1 (DM1) (Davis et al., 1997) and type 2 (DM2) (Liquori et al., 2001), Fragile X-associated tremor/ataxia syndrome (FXTAS) (Tassone et al., 2004), Spinocerebellar ataxia type 8 (SCA8) (Daughters et al., 2009) and Huntington's disease-like 2 (HDL2) (Rudnicki et al., 2007). All these diseases are characterized by microsatellite expansions of CNG or CCTG repeats in specific genes, leading to the accumulation of their transcripts as nuclear RNA foci (Ranum and Cooper, 2006).

Myotonic dystrophy is a chronic, slowly progressing, highly variable, inherited multisystemic disease. Two types of myotonic dystrophy exist. Type 1 (DM1), also known as Steinert disease, has a severe congenital form and a milder childhood-onset form. Type 2 (DM2), also known as proximal myotonic myopathy (PROMM), is rarer and generally manifests with milder signs and symptoms than DM1. DM1 is the most common adult form of muscular dystrophy with a prevalence of up to 1 in 7,000 worldwide. DM1 is highly prevalent in the Saguenay region of Quebec where its carrier rate reaches 1 in 550, making DM1 a Canadian-specific disease. There is no current treatment for the progressive myopathy, which eventually kills the patients, highlighting the urgent medical need for therapeutics. It is a multisystemic disorder (FIG. 1), caused by an expansion of CUG trinucleotide repeats in the 3' untranslated region (UTR) of the protein kinase DMPK mRNA (Brook et al. 1992, Buxton et al. 1992, Fu et al. 1992, Mahadevan et al. 1992). The expanded CUG repeats have been shown to cause the retention of this transcript in the nucleus, where it accumulates in numerous foci (FIG. 2; Taneja et al. 1995, Davis et al. 1997). The current toxic RNA hypothesis posits that the retention of mutant DMPK (dystrophia myotonica protein kinase) mRNAs in the nucleus alters the function of RNA-binding proteins, such as the alternative splicing factors MBNL1 and CUGBP1. As a consequence, mRNA missplicing has been reported for several genes in DM1 (reviewed in Wheeler and Thornton 2007). One of the mechanisms proposed is that these nuclear RNA foci sequester essential proteins that normally interact with CUG nucleotides in mRNAs and interfere with their normal function in the cell. Disrupting these nuclear RNA foci and promoting the nuclear export of the CUG-rich transcripts should reduce the alteration of splicing factor function and prevent the development of symptoms in patients with DM1 (Wheeler 2008).

There is thus a need for the development of novel strategies to inhibit the aggregation of RNA with expanded tracts of triplet repeats, for the treatment of diseases associated with the presence of triplet repeats The present description refers to a number of documents, the content of which is herein incorporated by reference in their entirety.

SUMMARY OF THE INVENTION

The present invention relates to compounds, as well as to uses thereof, such as to treat a polynucleotide repeat disorder (such as a trinucleotide repeat disorder, such as myotonic dystrophy).

In a first aspect, the present invention provides method for treating a polynucleotide repeat disorder, said method comprising administering to a subject in need thereof an effective amount of a compound of formula (1), (2), or (3):

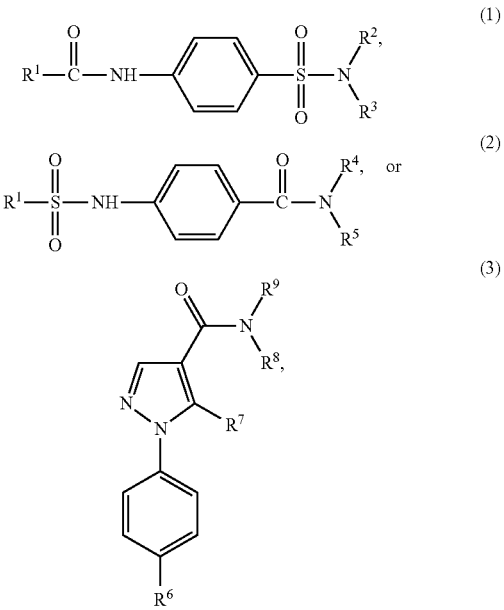

wherein:
R¹ is:
  aryl, heteroaryl, arylmethyl, or heteroarylmethyl, said aryl, heteroaryl, arylmethyl, and heteroarylmethyl being optionally substituted on the aryl ring or on the methyl group by alkyl, alkenyl, or alkynyl, and said heteroaryl and heteroarylmethyl comprising only oxygen and/or nitrogen atoms as heteroatom(s), or alkyl, alkenyl or alkynyl, said alkyl, alkenyl and alkynyl being substituted by cycloalkyl, cycloalkenyl or cycloalkynyl, $R^2$ and $R^3$ are independently:
a hydrogen atom,
alkyl, alkenyl, or alkynyl,
cycloalkyl, cycloalkenyl, cycloalkynyl,
an aryl free of heteroatom,
aralkyl, or
an aliphatic heterocycle,
with the proviso that at least one of $R^2$ and $R^3$ is not a hydrogen atom or a $C_1$-$C_2$ alkyl, or $R^2$ and $R^3$, together with the nitrogen atom to which they are attached, form a 6- or more membered, optionally substituted, aromatic or aliphatic heterocycle, optionally comprising one or more additional nitrogen atom, $R^4$ and $R^5$ are independently:
a hydrogen atom,
alkyl, alkenyl, or alkynyl,
cycloalkyl, cycloalkenyl, cycloalkynyl,
an aryl free of heteroatom,
aralkyl, or
an aliphatic heterocycle,
with the proviso that at least one of $R^4$ and $R^5$ is not a hydrogen atom or a $C_1$-$C_2$ alkyl, or $R^4$ and $R^5$, together with the nitrogen atom to which they are attached, form a 6 membered, optionally substituted, aromatic or aliphatic heterocycle, optionally comprising one or more additional nitrogen or oxygen atom.

$R^6$ is H, halogen, or $C_1$-$C_8$ alkyl optionally substituted with one or more halogen atoms, $R^7$ is $C_1$-$C_8$ alkyl optionally substituted with one or more halogen atoms, $R^8$ and $R^9$ are independently alkyl, alkenyl, or alkynyl, said alkyl, alkenyl, and alkynyl being substituted by optionally substituted aryl or optionally substituted thioaryl, or $R^8$ and $R^9$, together with the nitrogen atom to which they are attached, form a 5- or more membered, optionally substituted, aromatic or aliphatic heterocycle, optionally comprising one or more additional nitrogen atom, and substituted with optionally substituted aryl, with the proviso that when $R^7$ is $C_1$, alkyl, $R^8$ and $R^9$ are independently alkyl, alkenyl, or alkynyl, said alkyl, alkenyl, and alkynyl being substituted by aryl or thioaryl, or a pharmaceutically acceptable salt thereof.

In embodiments of Formula (1), $R^1$ is substituted aryl, such as aryl substituted with one to three alkyl groups, preferably methyl groups. In embodiments, the substituted aryl is phenyl substituted with two methyl groups, such as:

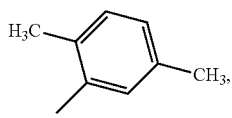

In embodiments of Formula (1), $R^1$ is an arylmethyl, preferably:

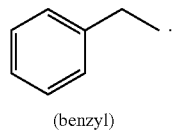
(benzyl)

In embodiments, the arylmethyl, such as benzyl, is substituted by an alkyl group, preferably a $C_{1-3}$ alkyl group, such as ethyl. In embodiments, the alkyl group substitutes the methyl group of the arylmethyl. In embodiments, $R^1$ is:

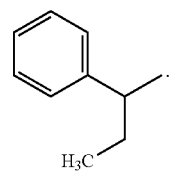

In embodiments of Formula (1), $R^1$ is an unsubstituted or substituted heteroaryl. In embodiment, the heteroaryl comprises one or two oxygen atoms, such as:

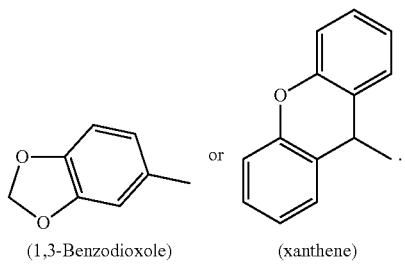
(1,3-Benzodioxole)   (xanthene)

In other embodiments, the heteroaryl comprises one or two nitrogen atoms, preferably one nitrogen atom, such as:

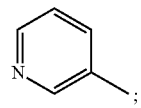

The heteroaryl may be substituted, for example with one to three alkyl groups, preferably methyl groups. In embodiments, the substituted heteroaryl is 1-phenyl-1H-pyrazole substituted with one methyl group, such as:

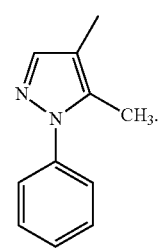

In embodiments of Formula (1), $R^1$ is an alkyl substituted cycloalkyl, preferably $C_{1-6}$ alkyl substituted with $C_{5-6}$ cycloalkyl. In a further embodiment $R^1$ is:

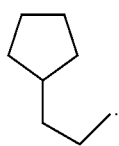

In embodiments, one of $R^2$ and $R^3$ is hydrogen or alkyl (preferably $C_1$-$C_3$ alkyl), and the other is alkyl comprising 3 or more carbon atoms, aralkyl (preferably phenyl-alkyl) or cycloalkyl (preferably cyclohexyl or adamantyl).

In an embodiment, $R^2$ and $R^3$ are $C_{3-6}$ alkyl, preferably propyl.

In an embodiment, $R^2$ is H and $R^3$ is a $C_3$-$C_6$ alkyl, in a further embodiment, $R^3$ is a $C_4$ alkyl, such as n-butyl, tert-butyl, or sec-butyl.

In an embodiment, $R^2$ is H and $R^3$ is a $C_3$-$C_{12}$ cycloalkyl. In a further embodiment, $R^3$ is adamantyl, such as adamant-1-yl:

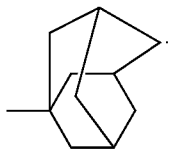

In an embodiment, $R^2$ is H and $R^3$ is an arylalkyl, such as benzyl.

In an embodiment, $R^2$ is alkyl and $R^3$ is alkyl comprising more than 3 carbon atoms.

In another embodiment, $R^2$ and $R^3$ form a substituted or unsubstituted 6- to 12-membered aliphatic heterocycle, which optionally comprises one or more additional nitrogen atom. In a further embodiment, said heterocycle is 6-membered. In yet a further embodiment, said heterocycle is 6-membered heterocycloalkyl comprising 0 or 1 additional nitrogen atom. In embodiments, the substituents are one to three $C_{1-6}$ alkyl, preferably methyl. In embodiments, $R^2$ and $R^3$ form:

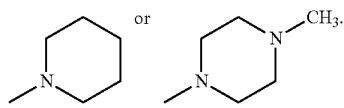

In embodiments of Formula (2), $R^1$ is substituted aryl, such as aryl substituted with one to three alkyl groups. In embodiment, the aryl is phenyl. In embodiments, the alkyl groups are methyl. In embodiments, there are two methyl groups. In embodiments, $R^1$ is:

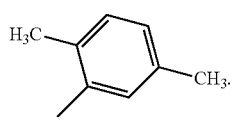

In embodiments, $R^4$ and $R^5$, together with the nitrogen atom to which they are attached, form a 6-membered, optionally substituted, aliphatic heterocycle, optionally comprising one or more additional nitrogen or oxygen atom. In further embodiments, the heterocycle comprises one further oxygen atom. In embodiments, the heterocycle is substituted with one to three alkyl groups, preferably two methyl groups. In embodiments, $R^4$ and $R^5$, together with the nitrogen atom to which they are attached, form:

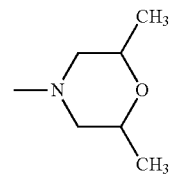

In an embodiment, $R^6$ is H or a halogen, in a further embodiment the halogen is Cl.

In an embodiment, $R^7$ is a $C_1$-$C_3$ alkyl optionally substituted with one or more halogen atoms, such as three fluoride atoms. In embodiments, R7 is methyl, ethyl, propyl, or —$CF_3$, preferably methyl, propyl or —$CF_3$, more preferably propyl.

In an embodiment, $R^8$ and $R^9$ are independently alkyls, such as $C_{1-3}$ alkyls, preferably methyl groups, substituted by aryl or thioaryl, preferably phenyl and/or 2-thienyl. In a further embodiment, $NR^8R^9$ is:

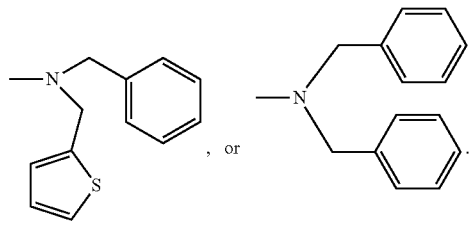

In another embodiment, when $R^7$ is not a $C_1$ alkyl, $R^8$ and $R^9$, together with the nitrogen atom to which they are attached, join to form a substituted 5- or more membered aliphatic heterocycle. In embodiments, the aliphatic heterocycle may be pyrrolidinyl or piperidinyl. In a further embodiment, the heterocycle is substituted with an optionally substituted aryl, preferably optionally substituted phenyl. Substituents for the aryl include $C_{1-6}$ alkyl and $C_{1-6}$ alkyloxy. In yet a further embodiment, $NR^8R^9$ is:

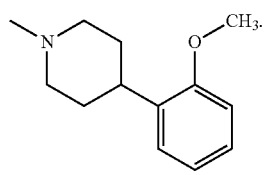

In further embodiments, the compound is:

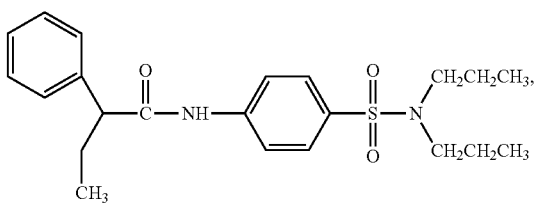

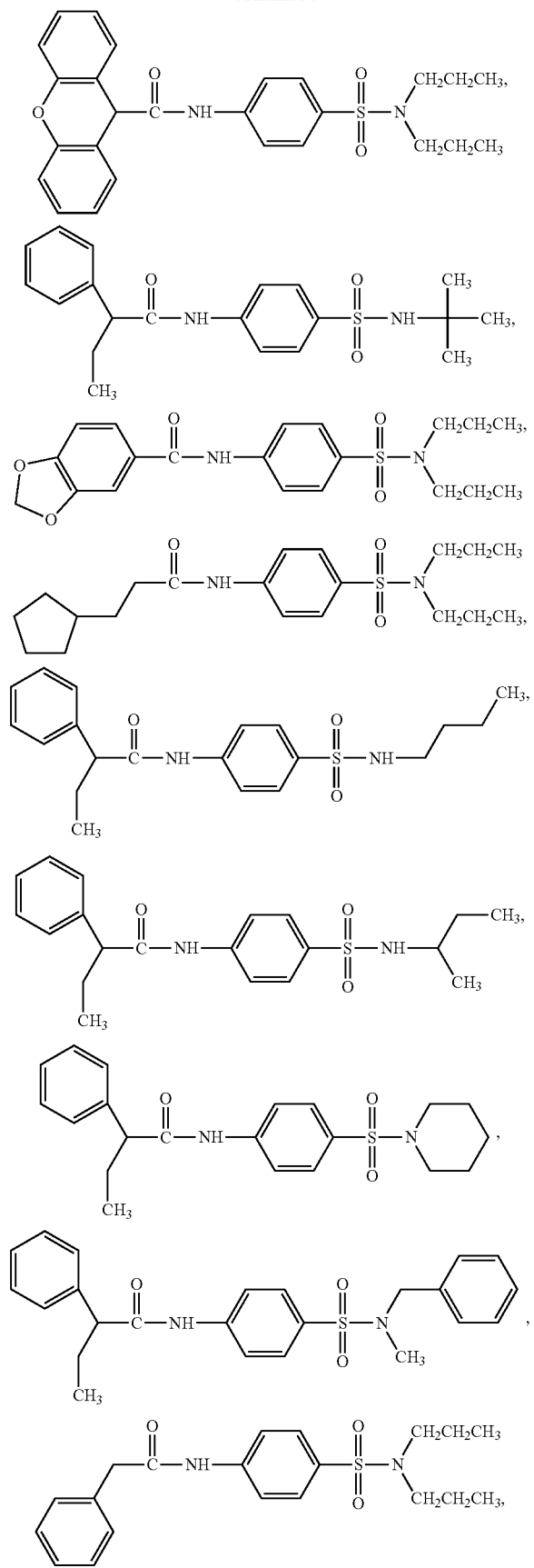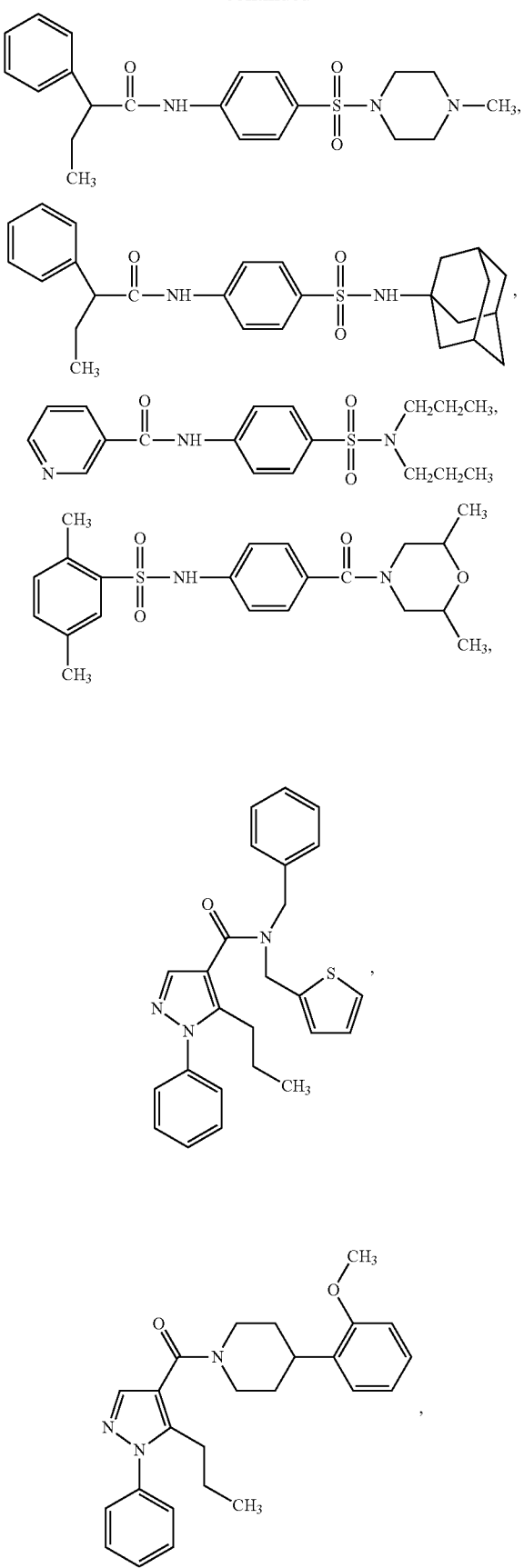

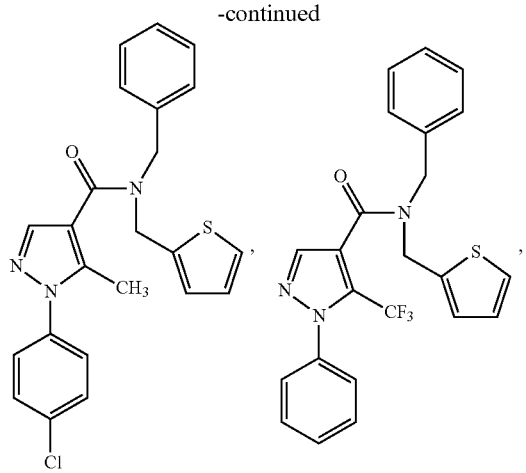

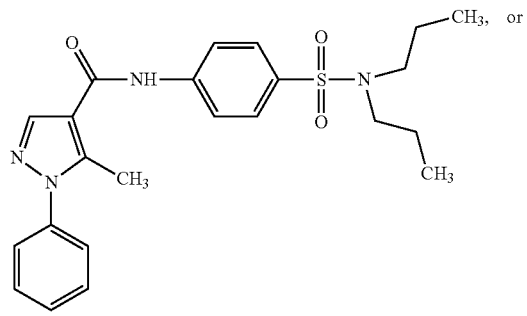

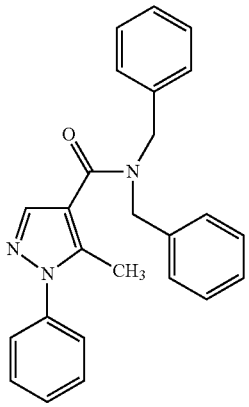

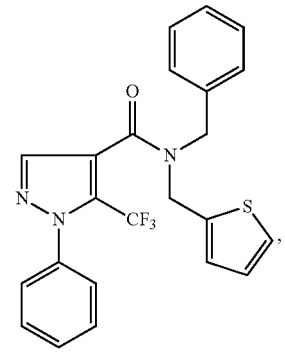

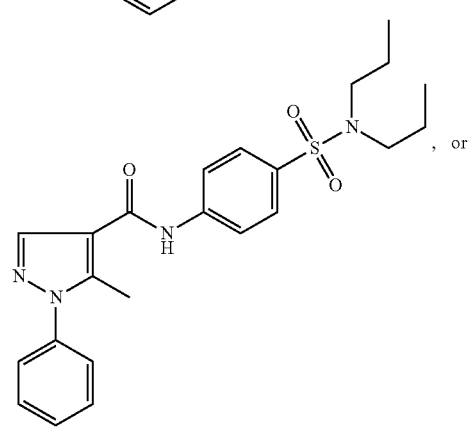

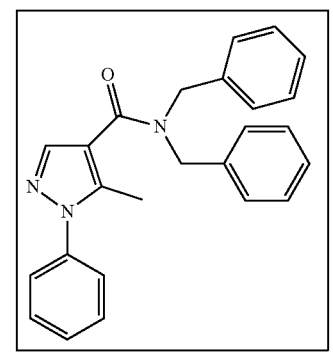

or a pharmaceutically acceptable salt thereof.

In another aspect, the present invention provides the compound defined above for treating a polynucleotide repeat disorder in a subject. In another aspect, the present invention provides the compound defined above for the manufacture of a medicament for treating a polynucleotide repeat disorder in a subject.

In another aspect, the present invention provides the use of the compound defined above for treating a polynucleotide repeat disorder in a subject. In another aspect, the present invention provides the use of the compound defined above for the manufacture of a medicament for treating a polynucleotide repeat disorder in a subject.

In an embodiment, the polynucleotide repeat disorder is myotonic dystrophy, in a further embodiment myotonic dystrophy type 1 (Steinert's disease). In another aspect, the present invention provides a compound, wherein said compound is the compound defined above. In another related aspect, the present invention provides a composition comprising the above-mentioned compounds and a pharmaceutically acceptable carrier. In particular embodiments of these aspects of the invention, the compound is In another aspect, the present invention provides a method for reducing the formation of RNA foci or aggregates in a cell, said method comprising contacting said cell with the compound defined above. In an embodiment, the method is in vitro. In another embodiment, the method is in vivo. In an embodiment, the RNA is a mutated mRNA comprising polynucleotide repeats, such as trinucleotide (or triplet) repeats.

In another aspect, the present invention provides a method for determining whether a test compound may be useful for treating a polynucleotide repeat disorder, said method comprising contacting said test compound with a cell expressing a reporter construct, said reporter construct comprising a first domain encoding a reporter transcript and a second domain comprising a plurality of polynucleotide repeats located downstream of said first domain, and determining the aggregation of said reporter transcript in said cell, wherein a decrease in the aggregation of said reporter transcript in said cell in the presence of said test compound, relative to the aggregation in the absence of said test compound, is indicative that said test compound may be useful for treating a polynucleotide repeat disorder.

In an embodiment, said second domain of said reporter construct comprises at least 100 polynucleotide repeats, in a further embodiment, at least 200 polynucleotide repeats, in a further embodiment, at least 300 polynucleotide repeats, in a further embodiment, 100-1500 polynucleotide repeats, in further embodiments, 100, 200, 300 or 1250 polynucleotide repeats.

In an embodiment, the polynucleotide repeat is a trinucleotide repeat.

In an embodiment, the decrease in the aggregation of said reporter transcript in said cell is determined by quantifying the number of reporter transcript foci in the nucleus of said cell.

In an embodiment, the above-mentioned reporter transcript is a luciferase or beta-galactosidase transcript.

In an embodiment, the above-mentioned reporter construct is under inducible expression.

In an embodiment, the above-mentioned reporter construct is operably linked to a tetracycline-responsive element (TRE).

In an embodiment, the above-mentioned cell further expresses the tetracycline-responsive transcriptional activator (tTA) from the strong immediate early promoter of cytomegalovirus ($P_{CMV}$).

In an embodiment, the above-mentioned expression is induced by culturing said cell in the absence of tetracycline (Tc), or a derivative thereof. In a further embodiment, the tetracycline (Tc) derivative is doxycycline (Dox).

In an embodiment, the above-mentioned method comprises:
culturing said cell in the absence of tetracycline (Tc), or a derivative thereof to induce expression of the reporter transcript; and
contacting said test compound with said cell in the presence of tetracycline (Tc), or a derivative thereof to inhibit expression of the reporter transcript.

Other objects, advantages and features of the present invention will become more apparent upon reading of the following non-restrictive description of specific embodiments thereof, given by way of example only with reference to the accompanying drawings.

BRIEF DESCRIPTION OF DRAWINGS

In the appended drawings:

FIG. 10 shows the effect of compounds #15 and 32 and representative analogues thereof on the alternative splicing of the endogenous MBNL2, MBNL1 and Serca1 transcripts. Myoblasts from a DM1 patient were treated with DMSO, compound 15 (or analogs 8, 12, 19, 21, 22, 23, 24, 27, 28, 29, 31, 32n, 34), or compound 32 (or analogs 43, 46) at 20 µM concentration during 7 days. Correction of mis-splicing is reported in %, where 0% means no correction, while 100% reflects complete splicing correction. Toxicity of compounds is indicated by the ratio of viable cell number (where 1 corresponds to no toxicity), and the percentage of dead cells (%). Toxicity was measured by treating the cells for 7 days with 20 µM of compound or DMSO. All the values were obtained from the average of 3 independent experiments;

FIG. 11 shows the effect of analogs of compounds 15 and 32 on the alternative splicing of the endogenous MBNL2, MBNL1, Serca1 and TNNT2 transcripts. Myoblasts from a DM1 patient were treated with DMSO, analogues of compound 15 (8, 32n), or compound 32 (and analogues 102, 195, 196, 213, 214, 215, 216, 217, 218, 219, 220, 221) at 20 μM concentration during 7 days. Correction of mis-splicing is reported in %, where 0% means no correction, while 100% reflects complete splicing correction. All the values were obtained from the average of 3 independent experiments;

DISCLOSURE OF INVENTION

Figure 1:
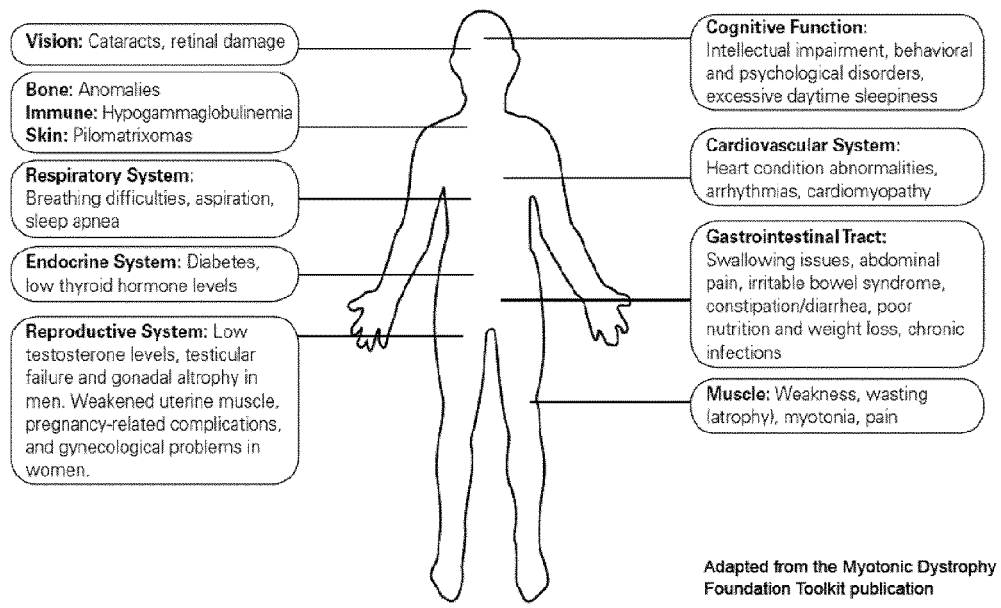
FIG. 1 shows the symptoms of myotonic dystrophy.
Figure 2:
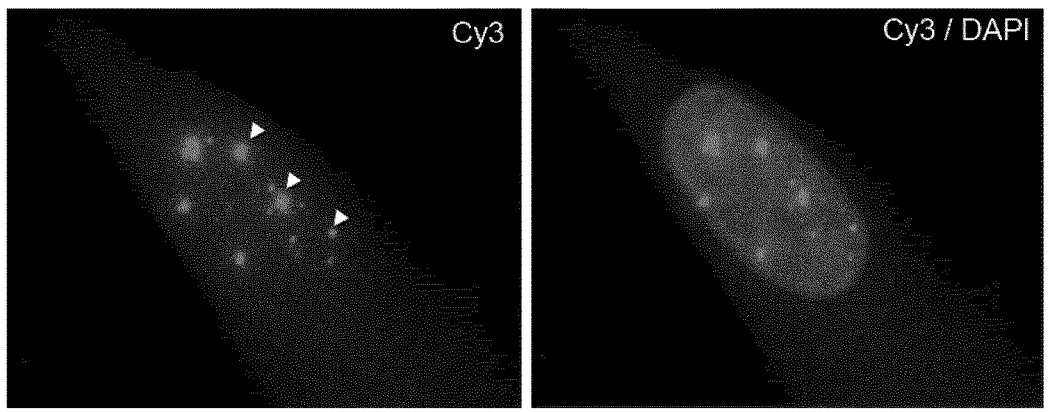
FIG. 2 shows DM1 patient fibroblasts with a 2000 CUG-triplet repeat expansion in the 3'UTR of the DMPK mRNA. This mutant mRNA forms nuclear foci which can be detected by fluorescent in situ hybridisation (FISH) (arrows)

In the studies described herein, the present inventors have demonstrated that compounds having the structure of formula (1) and (2) defined below reduce the formation of mutant DMPK mRNA foci in DM1 patient myoblasts, have the capacity to correct the stabilization of the CUGBP1 alternative splicing factor in DM1 myoblasts, and correct the mis-splicing of specific mRNAs in DM1 cells. These compounds may thus be useful for the treatment of diseases associated with the accumulation of RNA foci (RNA aggregates), such as expanded polynucleotide (e.g. trinucleotide) repeat disorders.

Accordingly, in a first aspect, the present invention provides method for treating a polynucleotide repeat disorder, said method comprising administering to a subject in need thereof an effective amount of a compound of formula (1), (2), or (3):

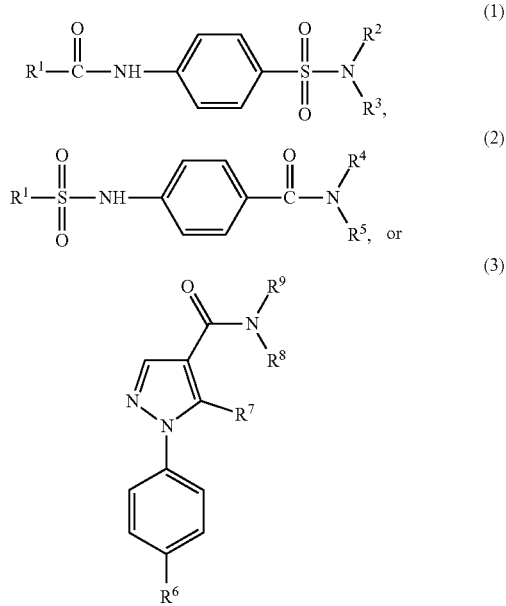

wherein:
$R^1$ is:
  aryl, heteroaryl, arylmethyl, or heteroarylmethyl, said aryl, heteroaryl, arylmethyl, and heteroarylmethyl being optionally substituted on the aryl ring or on the methyl group by alkyl, alkenyl, or alkynyl, and said heteroaryl and heteroarylmethyl comprising only oxygen and/or nitrogen atoms as heteroatom(s), or
  alkyl, alkenyl or alkynyl, said alkyl, alkenyl and alkynyl being substituted by cycloalkyl, cycloalkenyl or cycloalkynyl,
$R^2$ and $R^3$ are:
  a hydrogen atom,
  alkyl, alkenyl, or alkynyl,
  cycloalkyl, cycloalkenyl, cycloalkynyl,
  an aryl free of heteroatom,
  aralkyl, or
  an aliphatic heterocycle,
  with the proviso that at least one of $R^2$ and $R^3$ is not a hydrogen atom or a $C_1$-$C_2$ alkyl, or $R^2$ and $R^3$, together with the nitrogen atom to which they are attached, form a 6- or more membered, optionally substituted, aromatic or aliphatic heterocycle, optionally comprising one or more additional nitrogen atom,
$R^4$ and $R^5$ are:
  a hydrogen atom,
  alkyl, alkenyl, or alkynyl,
  cycloalkyl, cycloalkenyl, cycloalkynyl,
  an aryl free of heteroatom,
  aralkyl, or
  an aliphatic heterocycle,
  with the proviso that at least one of $R^4$ and $R^5$ is not a hydrogen atom or a $C_1$-$C_2$ alkyl, or $R^4$ and $R^5$, together with the nitrogen atom to which they are attached, form a 6 membered, optionally substituted, aromatic or aliphatic heterocycle, optionally comprising one or more additional nitrogen or oxygen atom,
$R^6$ is H, halogen, or $C_1$-$C_8$ alkyl optionally substituted with one or more halogen atoms,
$R^7$ is $C_1$-$C_8$ alkyl optionally substituted with one or more halogen atoms,
$R^8$ and $R^9$ are independently alkyl, alkenyl, or alkynyl, said alkyl, alkenyl, and alkynyl being substituted by optionally substituted aryl or optionally substituted thioaryl, or
$R^8$ and $R^9$, together with the nitrogen atom to which they are attached, form a 5- or more membered, optionally substituted, aromatic or aliphatic heterocycle, optionally comprising one or more additional nitrogen atom, and substituted with optionally substituted aryl,
with the proviso that when $R^7$ is $C_1$ alkyl, $R^8$ and $R^9$ are independently alkyl, alkenyl, or alkynyl, said alkyl, alkenyl, and alkynyl being substituted by aryl or thioaryl,
or a pharmaceutically acceptable salt thereof.

As used herein, "alkyl" or the prefix "alk" refers to an optionally substituted straight or branched chain saturated hydrocarbon group. Examples of straight or branched chain alkyl groups include, but are not limited to, methyl, trifluoromethyl, ethyl, 1-propyl, 2-propyl, 1-butyl, 2-butyl, 2-methyl-1-propyl, 2-methyl-2-propyl, 1-pentyl, 2-pentyl, 3-pentyl, 2-methyl-1-butyl, 3-methyl-1-butyl, 2-methyl-3-butyl, 2,2-dimethyl-1-propyl, 1-hexyl, 2-hexyl, 3-hexyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3, 3-dimethyl-1-butyl, 2-ethyl-1-butyl, 1-heptyl, and 1-octyl. A substituted alkyl can be substituted with one or more (e.g., 2, 3, 4, 5, 6, or 7) substituent groups such as -halogen, $—NH_2$, $—NH(C_1$-$C_{12}$ alkyl), —N(C$_1$-C$_{12}$ alkyl)$_2$, —OH, —O—(C$_1$-C$_{12}$ alkyl), or C$_6$-C$_{10}$ aryl groups, such as phenyl or naphthyl groups, or any other substituent group described herein. In an embodiment, the alkyl group contains 1-12 carbons, in further embodiments 1-8, 1-6 or 1-3 carbons.

As used herein, "aryl" refers to an optionally substituted monocyclic or polycyclic structure wherein all rings are aromatic, either fused together (e.g. naphthalene) or linked together (e.g. biphenyl) and formed by carbon atoms. Exemplary aryl groups include phenyl, naphthyl, and biphenyl. Where an aryl group is substituted, substituents can include any substituent groups described herein. In an embodiment, the aryl comprises from 6 to 15 carbons (C$_6$-C$_{15}$ aryl).

As used herein, "heteroaryl" or "heteroaromatic" refers to an aryl where one or more carbon atom has been replaced by an heteroatom, such as N, O, or S. In an embodiment, the heteroaryl is 5-6 membered.

As used herein, "arylalkyl" refers to an aryl group attached to the parent molecular group through an alkyl group. In an embodiment, the "arylalkyl" is a "C$_7$-C$_{14}$ arylalkyl" having the formula —(C$_x$-alkyl)-(C$_y$-aryl) wherein (x+y) is an integer between 7 and 14 and x is at least 1. Where an arylalkyl group is substituted, substituents can include any substituent group described herein.

As used herein, "arylalkenyl" and "arylalkynyl" refer to an aryl group attached to the parent molecular group through an alkenyl and alkynyl group, respectively.

As used herein, "cycloalkyl" refers to an optionally substituted, aliphatic, saturated or unsaturated monocyclic or polycyclic (e.g., bicyclic or tricyclic) hydrocarbon ring system. Polycyclic cycloalkyls may be linear, fused, bridged, or spirocyclic. In an embodiment, the cycloalkyl contains 3-12 carbon atoms (C$_3$-C$_{12}$ cycloalkyl).

As used herein, "cycloalkylalkyl" refers to a cycloalkyl group attached to the parent molecular group through an alkyl group. As used herein, "cycloalkylalkenyl" and "cycloalkylalkynyl" refer to a cycloalkyl group attached to the parent molecular group through an alkenyl and alkynyl group, respectively.

As used herein, "alkenyl" refers to an optionally substituted unsaturated, straight or branched chain hydrocarbon group containing at least one carbon-carbon double bond. In an embodiment, the alkenyl comprises from 2 to 8 carbon atoms "C$_2$-C$_8$ alkenyl", in a further embodiment from 2 to 6 or 2 to 4 carbon atoms.

As used herein, "alkynyl" refers to an optionally substituted unsaturated, straight or branched chain hydrocarbon group containing at least one carbon-carbon triple bond. In an embodiment, the alkynyl comprises from 2 to 8 carbon atoms "C$_2$-C$_8$ alkynyl", in a further embodiment from 2 to 6, or 2 to 4 carbon atoms.

As used herein, "halogen" refers to —F, —Cl, —Br, or —I.

As used herein, a "heterocycle" or "heterocyclyl" is an optionally substituted aromatic or aliphatic monocyclic or bicyclic ring system that includes one or more carbon atoms and heteroatoms (e.g., 1, 2, 3, or 4 heteroatoms), such as oxygen, nitrogen, and sulfur. Aliphatic heterocycles may have one or more double bonds. Examples of double bonds include carbon-carbon double bonds (C=C), carbon-nitrogen double bonds (C=N), and nitrogen-nitrogen double bonds (N=N). Examples of 3- to 9-membered heterocycles include, but are not limited to, aziridinyl, oxiranyl, thiiranyl, azirinyl, diaziridinyl, diazirinyl, oxaziridinyl, azetidinyl, azetidinonyl, oxetanyl, thietanyl, diazinanyl, piperidinyl, tetrahydropyridinyl, piperazinyl, morpholinyl, azepinyl or any partially or fully saturated derivatives thereof, diazepinyl or any partially or fully saturated derivatives thereof, pyrrolyl, oxazinyl, thiazinyl, diazinyl, triazinyl, tetrazinyl, imidazolyl, benzimidazolyl, tetrazolyl, indolyl, isoquinolinyl, quinolinyl, quinazolinyl, pyrrolidinyl, purinyl, isoxazolyl, benzisoxazolyl, furanyl, furazanyl, pyridinyl, oxazolyl, benzoxazolyl, thiazolyl, benzthiazolyl, thiophenyl, pyrazolyl, triazolyl, benzodiazolyl, benzotriazolyl, pyrimidinyl, isoindolyl, and indazolyl. Where an heterocycle is substituted, substituents can include any substituent group described herein. In an embodiment, the heterocycle is a "3- to 9-membered heterocycle".

As used herein, "heterocyclylalkyl" refers to a heterocyclic group attached to the parent molecular group through an optionally substituted alkyl group.

As used herein, "aromatic" refers to a cyclic ring system having (4n+2) π electrons in conjugation, where n is 1, 2, or 3.

Any group described herein may be substituted or unsubstituted. When substituted, they may be with any desired substituent or substituents that do not adversely affect the desired activity of the compound. Examples of preferred substituents are those found in the exemplary compounds and embodiments disclosed herein, as well as substituents such as: halogen (chloro, iodo, bromo, or fluoro); C$_{1-6}$ alkyl; C$_{2-6}$ alkenyl; C$_{2-6}$ alkynyl; hydroxyl; C$_{1-6}$ alkoxyl; amino (primary, secondary, or tertiary); nitro; thiol; thioether; imine; cyano; amido; carbamoyl; phosphonato; phosphine; a phosphorus (V) containing group; carboxyl; thiocarbonyl; sulfonyl; sulfonamide; ketone; aldehyde; ester; oxo; haloalkyl (e.g., trifluoromethyl); cycloalkyl, which may be monocyclic or fused or non-fused polycyclic (e.g., cyclopropyl, cyclobutyl, cyclopentyl, or cyclohexyl), or aliphatic heterocyclic, which may be monocyclic or fused or non-fused polycyclic (e.g., pyrrolidinyl, piperidinyl, piperazinyl, morpholinyl, or thiazinyl); and aromatic carbocyclic or heterocyclic, monocyclic or fused or non-fused polycyclic (e.g., phenyl, naphthyl, pyrrolyl, indolyl, furanyl, thiophenyl, imidazolyl, oxazolyl, isoxazolyl, thiazolyl, triazolyl, tetrazolyl, pyrazolyl, pyridinyl, quinolinyl, isoquinolinyl, acridinyl, pyrazinyl, pyridazinyl, pyrimidinyl, benzimidazolyl, benzothiophenyl, or benzofuranyl). Specific substituent groups includes benzyloxy; —N(CH$_3$)$_2$; O-alkyl (O—CH$_3$); O-aryl; aryl; aryl-lower alkyl; —CO$_2$CH$_3$; —OCH$_2$CH$_3$; methoxy; —CONH$_2$; —OCH$_2$CONH$_2$; —SO$_2$NH$_2$; —OCHF$_2$; —CF$_3$; and —OCF$_3$. A substituted group may have 1, 2, 3, 4, 5, 6, 7, or 8 substituent groups. These substituent groups may optionally be further substituted with a substituent listed herein. Substituents may also be optionally substituted by a fused-ring structure or bridge, for example —OCH$_2$O—. In other embodiments, these substituents are not further substituted.

As used herein, "pharmaceutically acceptable salt(s)," includes but are not limited to salts of acidic or basic groups that may be present in compounds used in the present compositions. Exemplary pharmaceutically acceptable salts are described in Berge et al., *J. Pharm. Sci.* 1977; 66:1-19 and in Pharmaceutical Salts: Properties, Selection, and Use, (Eds. P. H. Stahl and CG. Wermuth, Wiley-VCH, 2008). Compounds included in the present compositions that are basic in nature are capable of forming a wide variety of salts with various inorganic and organic acids. The acids that may be used to prepare pharmaceutically acceptable acid addition salts of such basic compounds are those that form non-toxic acid addition salts, i.e., salts containing pharmacologically acceptable anions, including, but not limited to, sulfuric, citric, maleic, acetic, oxalic, hydrochloride, hydrobromide, hydroiodide, nitrate, sulfate, bisulfate, phosphate, acid phosphate, isonicotinate, acetate, lactate, salicylate, citrate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, mesylate, hydroxymethylsulfonate, hydroxyethyl sulfonate, and pamoate (i.e., 1,1'-methylene-bis-(2-hydroxy-3-naphthoate)) salts. Similarly, compounds of the invention that include ionizable hydrogens can be combined with various inorganic and organic bases to form salts. Representative alkali or alkaline earth metal salts include sodium, lithium, potassium, calcium, magnesium and the like, as well as nontoxic ammonium, quaternary ammonium, and amine cations, including, but not limited to, ammonium, tetramethylammonium, tetraethylammonium, methylamine, dimethylamine, trimethylamine, triethylamine, ethylamine, and the like.

In embodiments of Formula (1), $R^1$ is substituted aryl, such as aryl substituted with one to three alkyl groups, preferably methyl groups. In embodiments, the substituted aryl is phenyl substituted with two methyl groups, such as:

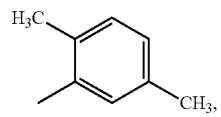

In an embodiment, $R^1$ is an arylmethyl. In embodiments, $R^1$ is an unsubstituted arylmethyl. In embodiments, the aryl group in the arylmethyl is phenyl. In a further embodiment, $R^1$ is:

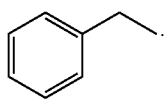

In other embodiments, $R^1$ is an arylmethyl substituted by an alkyl group, preferably a $C_{1-3}$ alkyl group, such as ethyl. In embodiments, the alkyl group substitutes the methyl group of the arylmethyl. In a further embodiment, $R^1$ is:

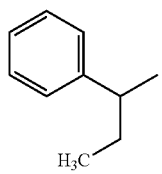

In another embodiment, $R^1$ is unsubstituted or substituted heteroaryl. In an embodiment, the heteroaryl group is unsubstituted.
In embodiments, the heteroaryl has an aryl ring fused to a 5-membered ring comprising one or two heteroatoms, preferably two oxygen atoms. In a further embodiment, $R^1$ is:

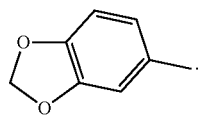

In other embodiments, the heteroaryl has two aryl rings fused to a 6-membered ring comprising one or two heteroatoms, preferably two oxygen atoms. In a further embodiment, $R^1$ is:

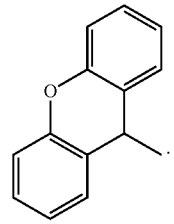

In another embodiment, $R^1$ is a heteroaryl comprising one or two heteroatoms. In an embodiment, the heteroaryl is unsubstituted. In an embodiment, the heteroaryl is 6-membered. In an embodiment, the heteroaryl has one heteroatom. In a further embodiment, the heteroatom is a nitrogen atom. In a further embodiment, $R^1$ is:

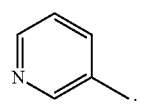

In other embodiments, the heteroaryl is substituted, for example with one to three alkyl groups, preferably methyl groups. In an embodiment, the heteroaryl comprises a 6-membered ring linked to a 5-membered ring. In embodiments, the 5-membered ring comprises one or two heteroatoms, preferably two nitrogen atoms. In embodiments, the substituted heteroaryl is 1-phenyl-1H-pyrazole substituted with one methyl group, such as:

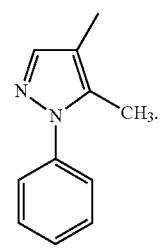

In another embodiment, $R^1$ is alkyl substituted with cycloalkyl. In a further embodiment $R^1$ is otherwise unsubstituted alkyl substituted with unsubstituted cycloalkyl. In an embodiment, the alkyl group in the alkylcycloalkyl is a $C_{1-6}$ alkyl, such as a $C_{1-4}$ alkyl. In a further embodiment, the alkyl is an ethyl group. In an embodiment, the cycloalkyl is a 5-membered cycloalkyl. In a further embodiment, $R^1$ is:

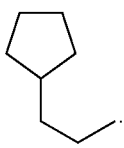

In an embodiment, $R^1$ is not:

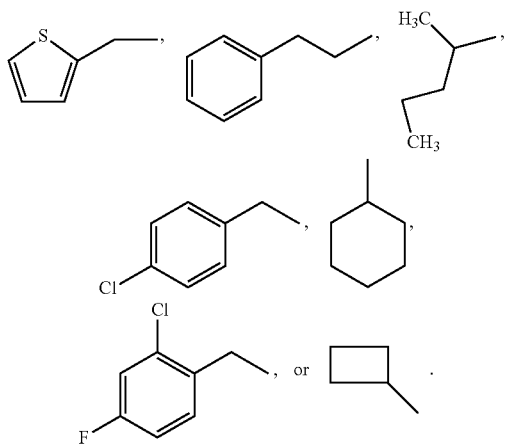

In embodiments, one of $R^2$ and $R^3$ is hydrogen or alkyl (preferably $C_1$-$C_3$ alkyl), and the other is alkyl comprising 3 or more carbon atoms, aralkyl (preferably phenyl-alkyl) or cycloalkyl (preferably cyclohexyl or adamantyl).

In an embodiment, $R^2$ is H and $R^3$ is a $C_3$-$C_6$ alkyl. In an embodiment, $R^3$ is linear. In another embodiment, $R^3$ is branched. In a further embodiment, $R^3$ is a $C_4$ alkyl. In a further embodiment, $NR^2R^3$ is:

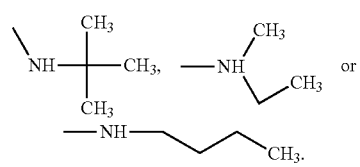

In an embodiment, $NR^2R^3$ is:

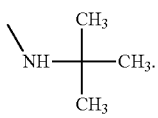

In an embodiment, $NR^2R^3$ is:

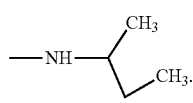

In an embodiment, $NR^2R^3$ is:

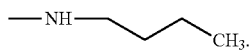

In an embodiment, $R^2$ and $R^3$ are $C_{3-6}$ alkyl, preferably propyl.

In another embodiment, $R^2$ is H and $R^3$ is a $C_3$-$C_{12}$ cycloalkyl, in a further embodiment a $C_{10}$ cycloalkyl. In a further embodiment, $R^3$ is adamantly, and $NR^2R^3$ is for example adamant-1-yl:

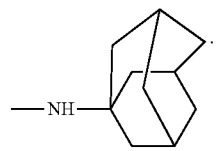

In another embodiment, $R^2$ is H and $R^3$ is a $C_7$-$C_{14}$ arylalkyl, such as a $C_7$-$C_{10}$ arylalkyl, in a further embodiment an unsubstituted arylalkyl. In a further embodiment $NR^2R^3$ is:

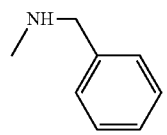

In another embodiment, $R^2$ and $R^3$ together with the nitrogen atom to which they are attached form an optionally substituted 6- to 9-membered non heterocycle. In an embodiment, the heterocycle comprises zero or one additional heteroatom, in a further embodiment the additional heteroatom is nitrogen. In an embodiment, the heterocycle is a 6-membered aliphatic heterocycle. In another embodiment, the heterocycle is substituted, in a further embodiment substituted with an alkyl, such as a $C_1$-$C_6$ or $C_1$-$C_4$ alkyl, preferably methyl. In a further embodiment, the substituent is methyl. In a further embodiment, $NR^2R^3$ is:

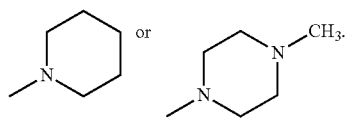

In an embodiment, $NR^2R^3$ is:

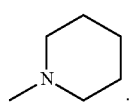

In an embodiment, $NR^2R^3$ is:

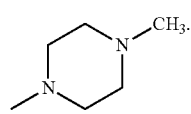

In an embodiment, $NR^2R^3$ is not:

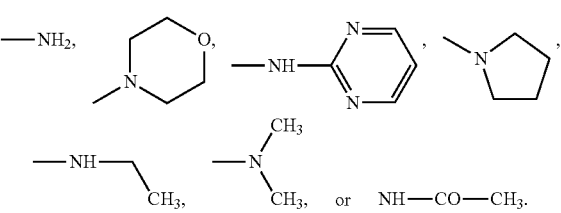

In an embodiment, the compound is a compound of formula (1a):
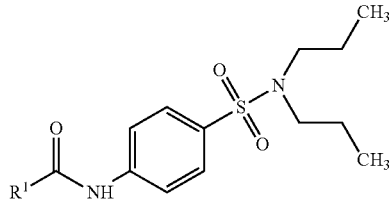
wherein $R^1$ is as defined above, or a pharmaceutically acceptable salt thereof.
In another embodiment, the compound is a compound of formula (1b):
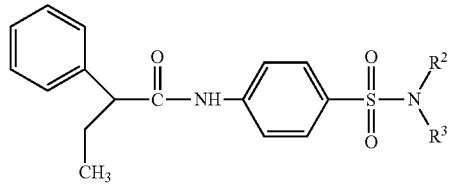
wherein $R^2$ and $R^3$ are as defined above, or a pharmaceutically acceptable salt thereof.
In a further embodiment, the compound is:
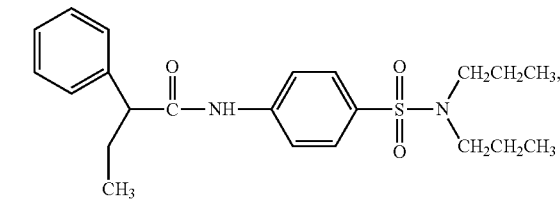
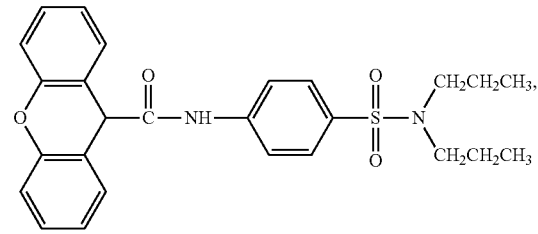
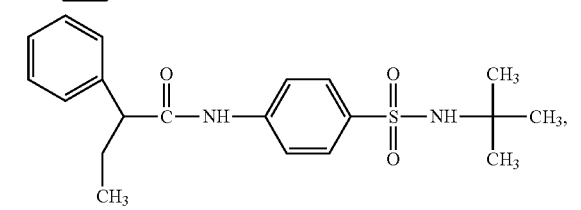
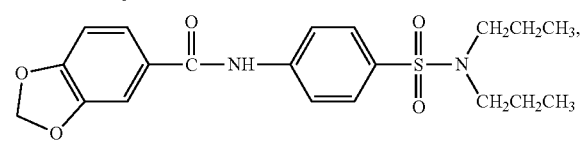
-continued
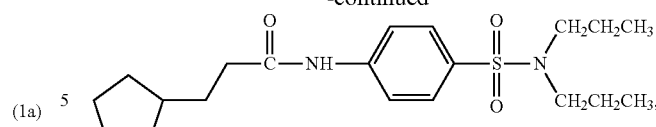
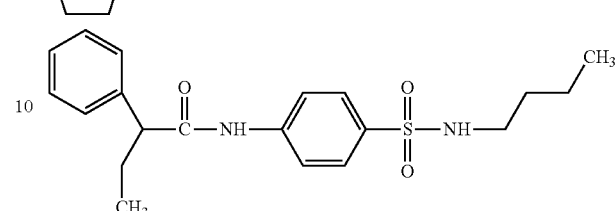
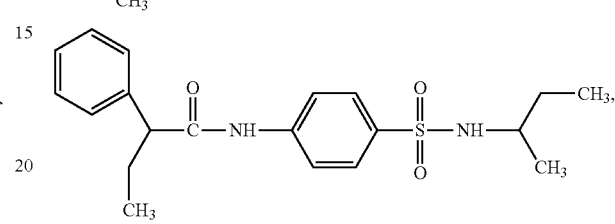
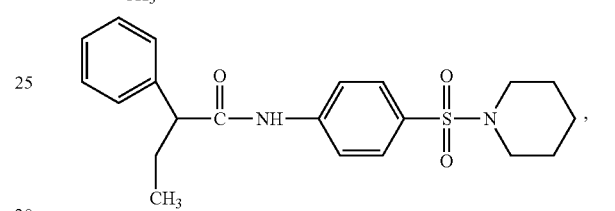
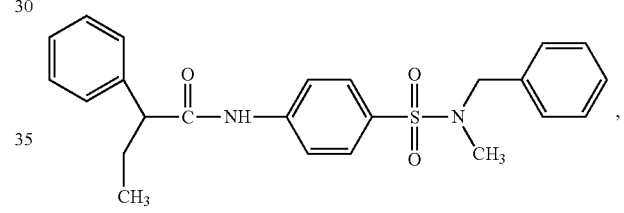
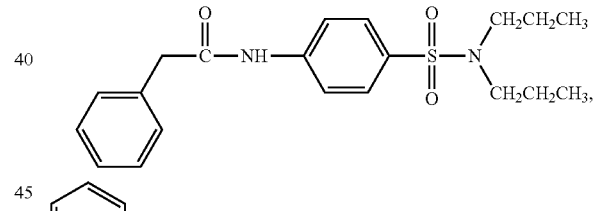
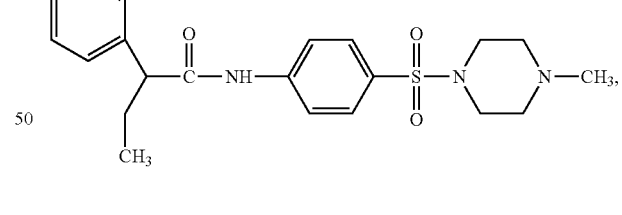
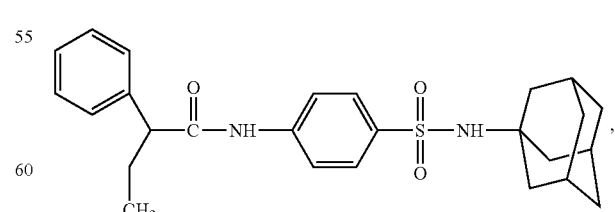
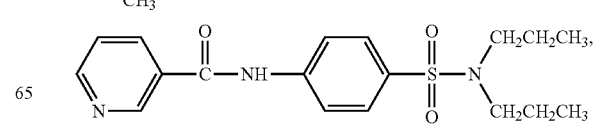

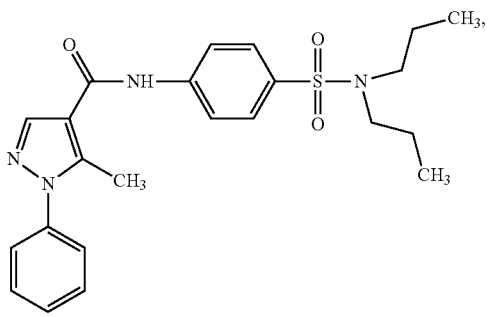 [SMILES: CCCN(CCC)S(=O)(=O)c1ccc(NC(=O)c2cnn(-c3ccccc3)c2C)cc1]

or a pharmaceutically acceptable salt thereof.

In an embodiment, the compound is:

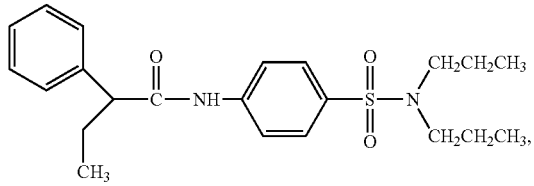

or a pharmaceutically acceptable salt thereof.

In an embodiment, the compound is:

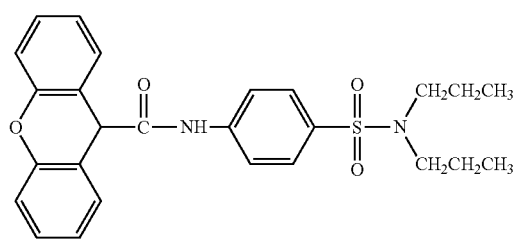

or a pharmaceutically acceptable salt thereof.

In an embodiment, the compound is:

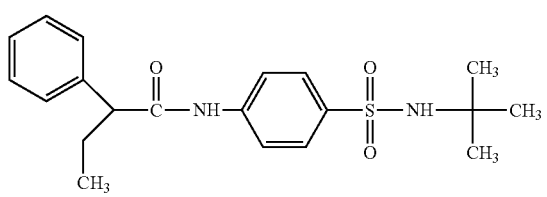 [SMILES: CCC(C(=O)Nc1ccc(S(=O)(=O)NC(C)(C)C)cc1)c1ccccc1]

or a pharmaceutically acceptable salt thereof.

In an embodiment, the compound is:

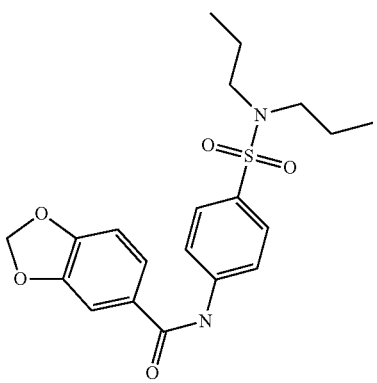 [SMILES: CCCN(CCC)S(=O)(=O)c1ccc(NC(=O)c2ccc3c(c2)OCO3)cc1]

or a pharmaceutically acceptable salt thereof.

In an embodiment, the compound is:

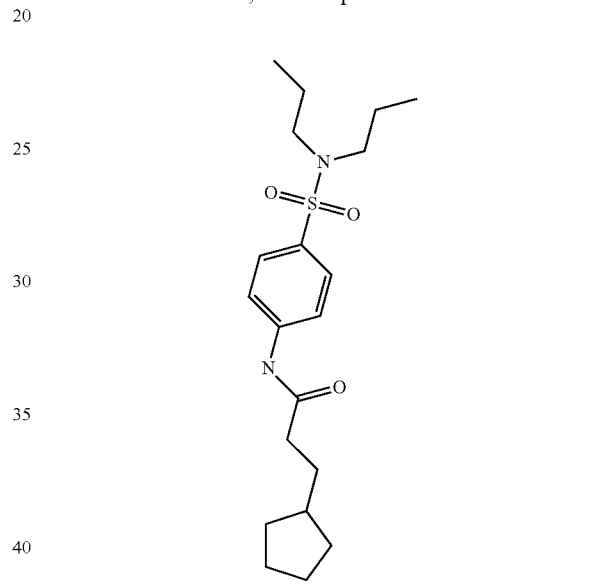

or a pharmaceutically acceptable salt thereof.

In an embodiment, the compound is:

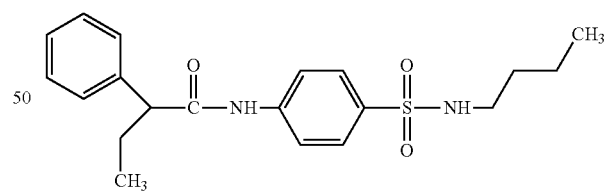

or a pharmaceutically acceptable salt thereof.

In an embodiment, the compound is:

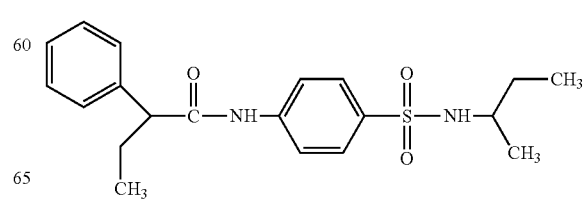

or a pharmaceutically acceptable salt thereof.
In an embodiment, the compound is:

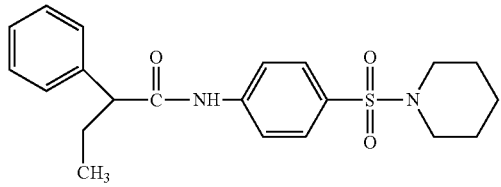 [SMILES: CCC(C(=O)Nc1ccc(S(=O)(=O)N2CCCCC2)cc1)c1ccccc1]

or a pharmaceutically acceptable salt thereof.
In an embodiment, the compound is:

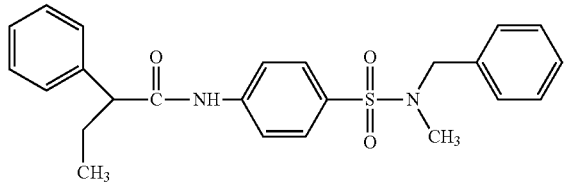 [SMILES: CCC(C(=O)Nc1ccc(S(=O)(=O)N(C)Cc2ccccc2)cc1)c1ccccc1]

or a pharmaceutically acceptable salt thereof.
In an embodiment, the compound is:

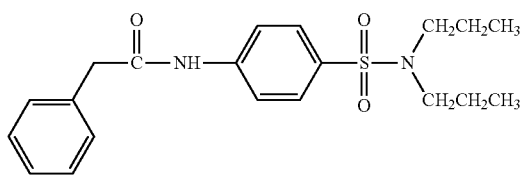

or a pharmaceutically acceptable salt thereof.
In an embodiment, the compound is:

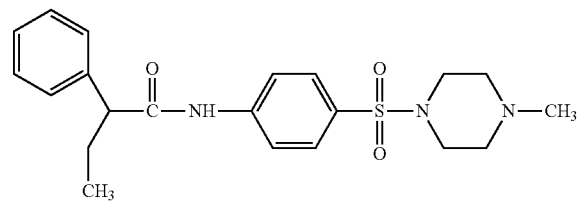

or a pharmaceutically acceptable salt thereof.
In an embodiment, the compound is:

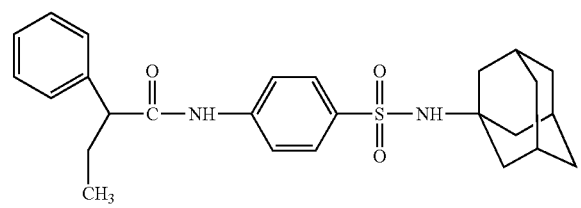 [SMILES: CCC(C(=O)Nc1ccc(S(=O)(=O)NC23CC4CC(CC(C4)C2)C3)cc1)c1ccccc1]

or a pharmaceutically acceptable salt thereof.
In an embodiment, the compound is:

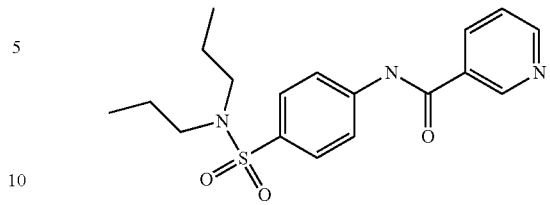

or a pharmaceutically acceptable salt thereof.
In an embodiment, the compound is:

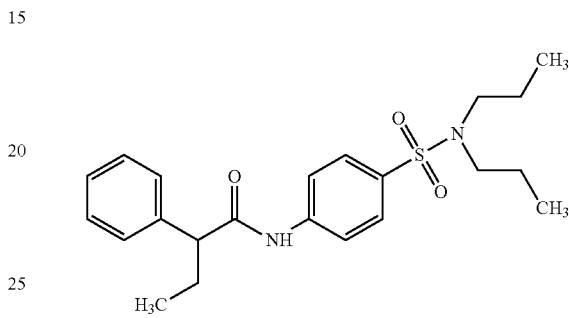

or a pharmaceutically acceptable salt thereof.
In an embodiment, the compound is:

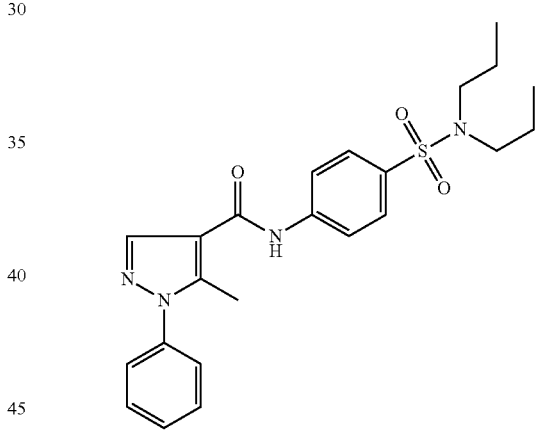

or a pharmaceutically acceptable salt thereof.

In embodiments of Formula (2), $R^1$ is a substituted or unsubstituted aryl, in a further embodiment a substituted aryl. In an embodiment, the aryl is substituted with an alkyl, for example one or three alkyl, in a further embodiment a $C_1$-$C_6$ or $C_1$-$C_4$ alkyl, such as a methyl. In embodiments, the substituted aryl is phenyl substituted with two methyl groups, such as:

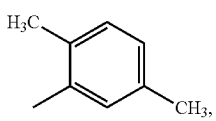

In embodiments, $R^4$ and $R^5$, together with the nitrogen atom to which they are attached, form a 6-membered, optionally substituted, aliphatic heterocycle, optionally comprising one or more additional nitrogen or oxygen atom. In further embodiments, the heterocycle comprises one further oxygen atom. In embodiments, the heterocycle is substituted with one to three alkyl groups, preferably two alkyl groups, preferably methyl groups. In embodiments, $R^4$ and $R^5$, together with the nitrogen atom to which they are attached, form:

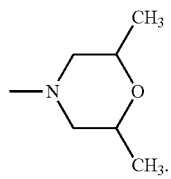

In an embodiment, the compound is:

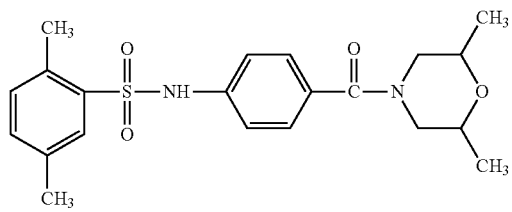

or a pharmaceutically acceptable salt thereof.

In an embodiment, $R^6$ is H or a halogen, in a further embodiment the halogen is Cl.

In an embodiment, $R^7$ is a $C_3$-$C_8$ alkyl, in a further embodiment a $C_3$-$C_6$ alkyl. In embodiment, the alkyl is substituted with one or more halogen atoms, for examples one to three such atoms, for example three fluoride atoms.

In an embodiment, $R^8$ and $R^9$ are independently alkyls, such as $C_{1-3}$ alkyls, preferably methyl groups, substituted by optionally substituted aryl or optionally substituted thioaryl. In embodiment, substituted preferably monocyclic aryl or thioaryl, for example phenyl and/or 2-thienyl, which are preferably unsubstituted. In a further embodiment, $NR^8R^9$ is:

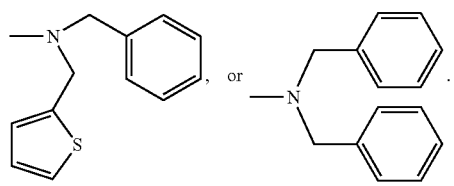

In another embodiment, when $R^7$ is not a $C_1$ alkyl, $R^8$ and $R^9$, together with the nitrogen atom to which they are attached, join to form a 5- or more membered substituted aliphatic heterocycle. In embodiments, the aliphatic heterocycle may be substituted pyrrolidinyl or piperidinyl:

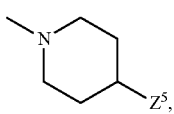

wherein $Z^5$ is a substituted or unsubstituted aryl. In a further embodiment, $Z^5$ is a substituted aryl, in a further embodiment the substituent is alkyloxy, such as a methoxy (—O—$CH_3$). In a further embodiment, $NR^8 R^9$ is:

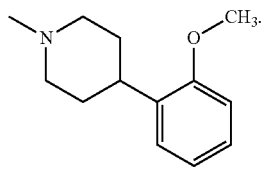

In a further embodiment, the compound is:

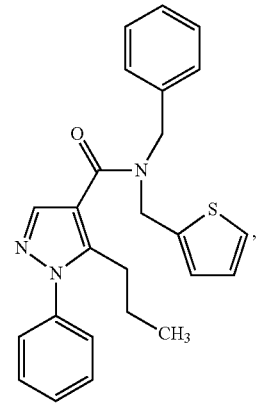

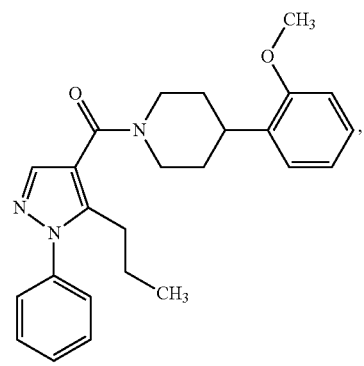

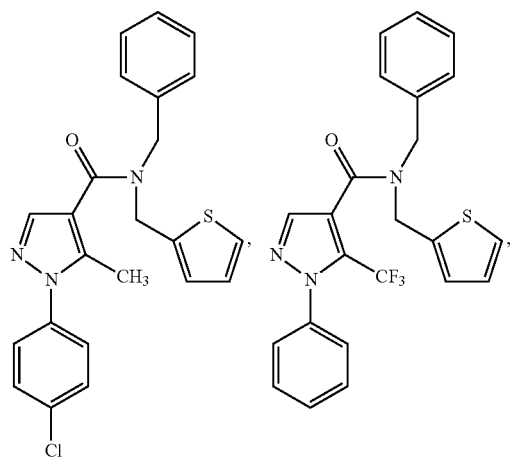

-continued

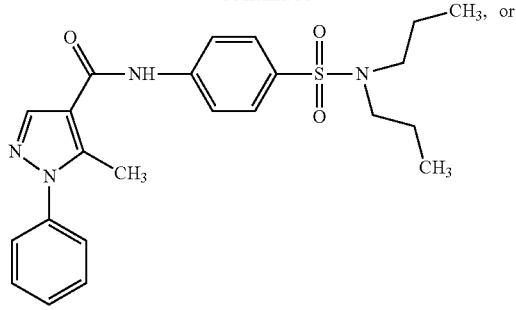

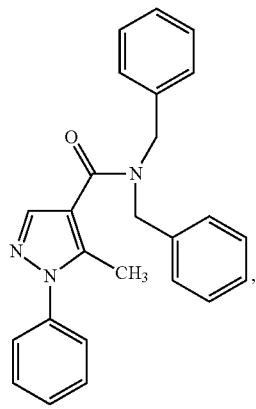 [SMILES: Cc1c(C(=O)N(Cc2ccccc2)Cc2ccccc2)cnn1-c1ccccc1]

or a pharmaceutically acceptable salt thereof.
In an embodiment, the compound is:

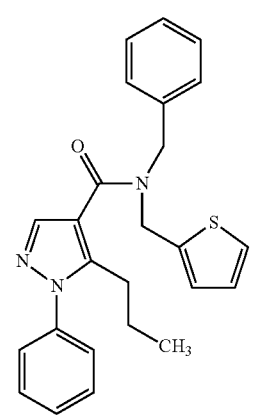 [SMILES: CCCc1c(C(=O)N(Cc2ccccc2)Cc2cccs2)cnn1-c1ccccc1]

or a pharmaceutically acceptable salt thereof.
In an embodiment, the compound is:

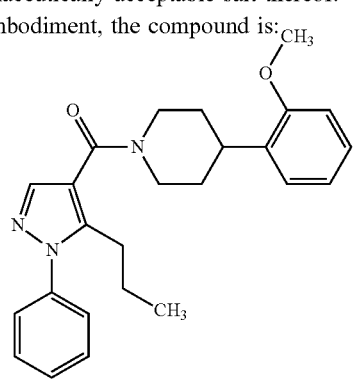

or a pharmaceutically acceptable salt thereof.

In an embodiment, the compound is:

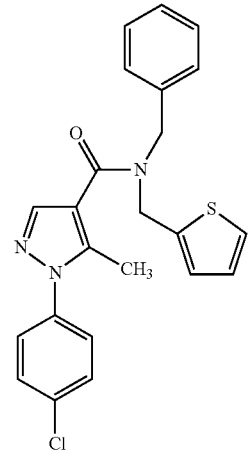 [SMILES: Cc1c(C(=O)N(Cc2ccccc2)Cc2cccs2)cnn1-c1ccc(Cl)cc1]

or a pharmaceutically acceptable salt thereof.
In an embodiment, the compound is:

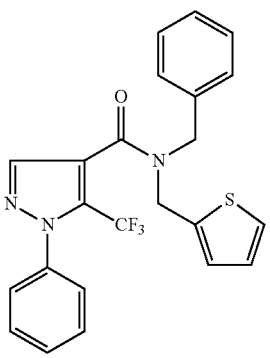 [SMILES: O=C(c1cnn(-c2ccccc2)c1C(F)(F)F)N(Cc1ccccc1)Cc1cccs1]

or a pharmaceutically acceptable salt thereof.
In an embodiment, the compound is:

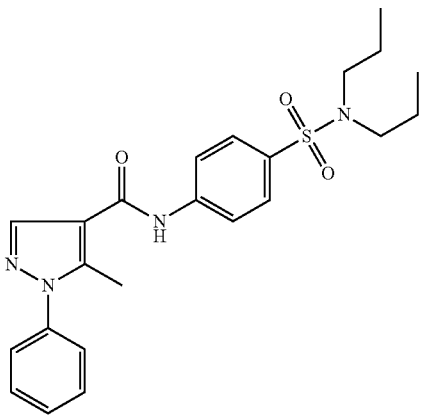 [SMILES: CCCN(CCC)S(=O)(=O)c1ccc(NC(=O)c2cnn(-c3ccccc3)c2C)cc1]

or a pharmaceutically acceptable salt thereof. thereof.

In an embodiment, the compound is:

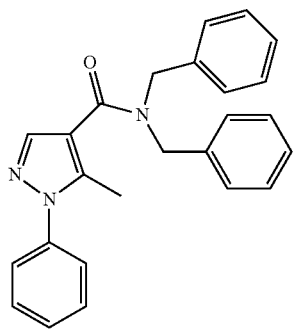 [SMILES: Cc1c(C(=O)N(Cc2ccccc2)Cc2ccccc2)cnn1-c1ccccc1]

or a pharmaceutically acceptable salt thereof.

In another aspect, the present invention provides a compound of formula 1, 1a, 1b, 2, 2a or (3) as defined above. In particular embodiments, the compound is:

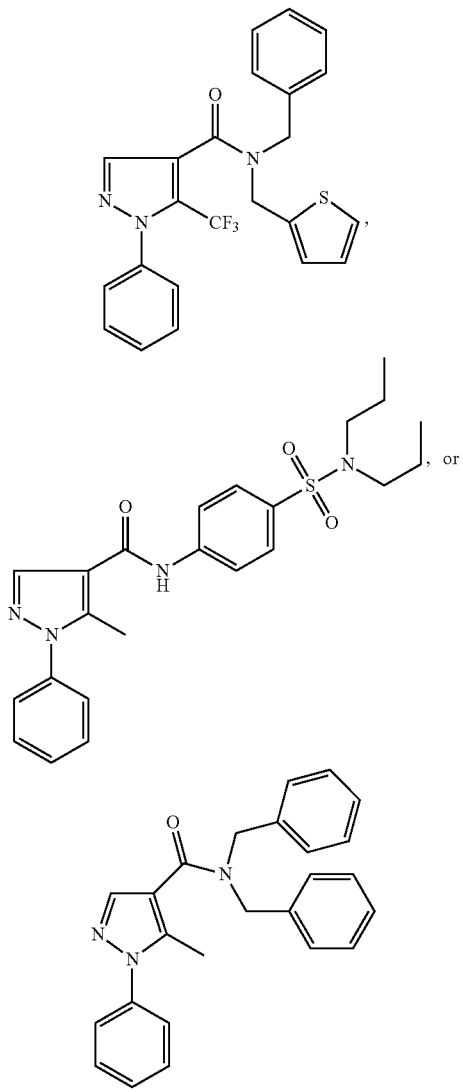

In an embodiment, the above-mentioned compound reduces the formation of mRNA foci or aggregates in a cell.

It will be appreciated that the above-defined compounds can contain one or more asymmetric carbon atoms which give rise to enantiomers. The compounds can be prepared as racemates or can be made from enantiomeric intermediates. Both racemates and enantiomers form part of the present invention.

The present invention also provides prodrugs of the compounds of the invention. Prodrugs include derivatives of the compounds of the invention that can hydrolyze, oxidize, or otherwise react under biological conditions (in vitro or in vivo) to provide an active compound of the invention. Examples of prodrugs include, but are not limited to, derivatives and metabolites of a compound of the invention that include biohydrolyzable moieties such as biohydrolyzable amides, biohydrolyzable esters, biohydrolyzable carbamates, biohydrolyzable carbonates, and biohydrolyzable phosphate analogues. In certain embodiments, prodrugs of the compounds of the invention with carboxyl functional groups are the lower alkyl esters of the carboxylic acid. The carboxylate esters are conveniently formed by esterifying any of the carboxylic acid moieties present on the molecule. Prodrugs can typically be prepared using well-known methods, such as those described by Burger's Medicinal Chemistry and Drug Discovery $6^{th}$ ed. (Donald J. Abraham ed., 2001, Wiley) and Design and Application of Prodrugs (H. Bundgaard ed., 1985, Harwood Academic Publishers Gmfh). Biohydrolyzable moieties of a compounds of the invention 1) do not interfere with the biological activity of the compound but can confer upon that compound advantageous properties in vivo, such as uptake, duration of action, or onset of action; or 2) are biologically inactive but are converted in vivo to the biologically active compound. Examples of biohydrolyzable esters include, but are not limited to, lower alkyl esters, alkoxyacyloxy esters, alkyl acylamino alkyl esters, and choline esters. Examples of biohydrolyzable amides include, but are not limited to, lower alkyl amides, α-amino acid amides, alkoxyacyl amides, and alkylaminoalkylcarbonyl amides. Examples of biohydrolyzable carbamates include, but are not limited to, lower alkylamines, substituted ethylenediamines, aminoacids, hydroxyalkylamines, heterocyclic and heteroaromatic amines, and polyether amines.

The above-mentioned compounds can be obtained via standard, well-known synthetic methodology, see e.g. March, J. Advanced Organic Chemistry; Reactions Mechanisms, and Structure, $4^{th}$ ed., 1992. Illustrative methods are described below. Starting materials useful for preparing the compounds of the invention and their intermediates are also commercially available or can be prepared from commercially available materials using known synthetic methods and reagents.

The compounds of formula 1, 1a and 1b may be synthesized, for example, based on the methods disclosed in PCT publication No. WO 99/36398.

Because of their activity, the above-defined compounds are advantageously useful in veterinary and human medicine. The compounds of formulas 1, 1a, 1b, 2, and 3 described herein are useful for the treatment of polynucleotide repeat disorders. In an embodiment, a compound described herein is formulated in a pharmaceutical composition, in association with one or more carrier(s). As used herein, "carrier", "pharmaceutical carrier" or "pharmaceutically-acceptable carrier" refers to a diluent, adjuvant, excipient, or vehicle with which a compound of the invention is administered. Such pharmaceutical carriers can be liquids, such as water and oils, including those of petroleum, animal, vegetable or synthetic origin, such as peanut oil, soybean oil, mineral oil, sesame oil and the like. Saline solutions and aqueous dextrose and glycerol solutions can also be employed as liquid carriers, particularly for injectable solutions. The pharmaceutical carriers can be saline, gum acacia, gelatin, starch paste, talc, keratin, colloidal silica, urea, and the like. In addition, auxiliary, stabilizing, thickening, lubricating and coloring agents may be used. Suitable pharmaceutical carriers also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, polyethylene glycol 300, water, ethanol, polysorbate 20, wetting or emulsifying agents, or pH buffering agents.

As used herein, and as well understood in the art, "treatment" is an approach for obtaining beneficial or desired therapeutic results, such as clinical results. Beneficial or desired results can include, but are not limited to, alleviation or amelioration of one or more symptoms or conditions (e.g., for myotonic dystrophy, one or more of the symptoms depicted in FIG. 1, such as muscle weakness, muscle wasting); diminishment of extent of disease, disorder, or condition; stabilization (i.e., not worsening) of state of disease, disorder, or condition; prevention of spread of disease, disorder, or condition; delay or slowing the progress of the disease, disorder, or condition; amelioration or palliation of the disease, disorder, or condition; and remission (whether partial or total). "Treatment" can also mean prolonging survival as compared to expected survival if not receiving treatment.

The term "polynucleotide repeat disorders" (or "polynucleotide repeat expansion disorders") refers to disorders characterized based upon the presence of unstable and abnormal expansions of DNA-repeats, which in turn typically results in abnormal expression of one or more genes. The most common types of repeats are trinucleotide repeats (often CAG, but also CCG, CTG, CGG, GCC or GAA). Accumulation of RNA foci (or RNA aggregates) is a hallmark of polynucleotide repeat disorders. Examples of polynucleotide repeat disorders include Huntington's disease (HD), Huntington's disease-like 2 (HDL2), spinocerebellar ataxias (types 1-8, 12 and 17), fragile X syndrome, fragile X-E syndrome, fragile X-associated tremor/ataxia syndrome, myotonic dystrophy (type 1 or type 2), juvenile myoclonic epilepsy, Dentatorubral-pallidoluysian atrophy (DRPLA), Friedreich's ataxia (FRDA), spinal and bulbar muscular atrophy (SBMA, also known as Kennedy's disease), chromosome 9p21 amyotrophic lateral sclerosis-frontotemporal dementia (ALS-FTD, associated with an hexanucleotide (GGGGCC) repeat expansion). In an embodiment, the trinucleotide repeat disorder is myotonic dystrophy, in a further embodiment myotonic dystrophy type 1 (DM1) (Steinert's disease).

In another aspect, the present invention provides a method for inhibiting the accumulation of RNA foci (RNA aggregates) in a cell, said method comprising contacting said cell with one or more compounds of formula 1, 1a, 1b, 2 and/or 3 defined above, or a composition defined above. In an embodiment, the method is an in vitro method. In another embodiment, the above-mentioned method is an in vivo method.

In another aspect, the present invention provides a method for treating a disease associated with accumulation of RNA foci (RNA aggregates), said method comprising administering to a subject in need thereof an effective amount of one or more compounds of formula 1, 1a, 1b, 2 and/or 3 defined above, or a composition defined above. Diseases associated with accumulation of RNA foci (RNA aggregates) include, for example, the polynucleotide repeat disorders noted above.

The patient or subject is an animal, including, but not limited to, a human, mammal, e.g., cow, horse, sheep, pig, cat, dog, mouse, rat, rabbit, mouse or guinea pig, or other animal such as a chicken, turkey, or quail. In an embodiment, the patient or subject is a human.

The present compositions, which comprise an effective amount of one or more of the above-defined compounds, can be administered by any convenient route, for example by infusion or bolus injection, or by absorption through epithelial or mucocutaneous linings (e.g., oral mucosa, rectal, intestinal mucosa, etc.), and can be administered together with another biologically active agent. Administration can be systemic or local. Various delivery systems are known, e.g., encapsulation in liposomes, microparticles, microcapsules, capsules, etc., and can be used to administer a compound. In certain embodiments, more than one compound is administered to a patient. Methods of administration include but are not limited to intradermal, intramuscular, intraperitoneal, intravenous, subcutaneous, intranasal, epidural, oral, sublingual, intranasal, intracerebral, intravaginal, transdermal, rectally, by inhalation, or topically to the ears, nose, eyes, or skin. The preferred mode of administration is left to the discretion of the practitioner.

In specific embodiments, it may be desirable to administer one or more compounds locally to the area in need of treatment. This may be achieved, for example, and not by way of limitation, by local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers.

Pulmonary administration can also be employed, e.g., by use of an inhaler or nebulizer, formulating with an aerosolizing agent, or via perfusion in a fluorocarbon or synthetic pulmonary surfactant. In certain embodiments, the compounds can be formulated as a suppository, with traditional binders and carriers such as triglycerides. In another embodiment, the compounds can be delivered in a vesicle, in particular a liposome. In yet another embodiment, the compounds can be delivered in a controlled-release system. The present compositions may include an effective amount of one or more of the above-defined compounds and a pharmaceutically acceptable carrier.

The present compositions can take the form of solutions, suspensions, emulsion, tablets, pills, pellets, capsules, capsules containing liquids, powders, sustained-release formulations, suppositories, emulsions, aerosols, sprays, suspensions, or any other form suitable for use.

Compounds, included in the present compositions, which are acidic in nature are capable of forming base salts with various pharmacologically or cosmetically acceptable cations. Examples of such salts include alkali metal or alkaline earth metal salts and, particularly, calcium, magnesium, sodium, lithium, zinc, potassium, and iron salts. In another embodiment, the compounds of the invention are formulated in accordance with routine procedures as a pharmaceutical composition adapted for intravenous administration to human beings. Typically, compounds for intravenous administration are solutions in sterile isotonic aqueous buffer. Where necessary, the compositions may also include a solubilizing agent. Compositions for intravenous administration may optionally include a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the compound is to be administered by infusion, it can be dispensed, for example, with an infusion bottle containing sterile pharmaceutical grade water or saline. Where the compound is administered by injection, an ampoule of sterile water for injection or saline can be provided so that the ingredients may be mixed prior to administration.

Compositions for oral delivery may be in the form of tablets, lozenges, aqueous or oily suspensions, granules, powders, emulsions, capsules, syrups, or elixirs, for example. Orally administered compositions may contain one or more optional agents, for example, sweetening agents such as fructose, aspartame or saccharin; flavoring agents such as peppermint, oil of wintergreen, or cherry; coloring agents; and preserving agents, to provide a pharmaceutically palatable preparation. Moreover, where in tablet or pill form, the compositions may be coated to delay disintegration and absorption in the gastrointestinal tract thereby providing a sustained action over an extended period of time. Oral compositions can include standard carriers such as mannitol, lactose, starch, magnesium stearate, sodium saccharine, cellulose, or magnesium carbonate. Such carriers can be of pharmaceutical grade.

The amount of the compound that will be effective in the treatment of a particular disorder or condition will depend on the nature of the disorder or condition, and can be determined by standard clinical techniques. In addition, in vitro or in vivo assays may optionally be employed to help identify optimal dosage ranges. The precise dose to be employed in the compositions will also depend on the route of administration, and the seriousness of the disease or disorder, and may be determined for a given case. Suitable effective dosage ranges for intravenous administration are generally about 0.01 to about 5 g, preferably about 0.01 to about 1 g of the compound per kilogram body weight. In specific embodiments, the i.v. dose is about 0.005 to about 0.5 g/kg, about 0.01 to about 0.3 g/kg, about 0.025 to about 0.25 g/kg, about 0.04 to about 0.20 g/kg, or about 0.05 to about 0.20 g/kg (or the equivalent doses expressed per square meter of body surface area). Alternatively, a suitable dose range for i.v. administration may be obtained using doses of about 1 to about 2000 mg, without adjustment for a patient's body weight or body surface area. Suitable dosage ranges for intranasal administration are generally about 0.01 pg/kg body weight to 10 mg/kg body weight. Suppositories generally contain 0.5% to 20% by weight of one or more compounds of the invention alone or in combination with another therapeutic agent. Oral compositions can contain about 10% to about 95% by weight of one or more compounds of the invention alone or in combination with another therapeutic agent. In specific embodiments of the invention, suitable dose ranges for oral administration are generally about 0.1 to about 200 mg, preferably about 0.5 to about 100 mg, and more preferably about 1 to about 50 mg of a compound of the invention per kilogram body weight or their equivalent doses expressed per square meter of body surface area. In specific embodiments the oral dose is about 0.25 to about 75 mg/kg, about 1.0 to about 50 mg/kg, about 2.0 to about 25 mg/kg, about 2.5 to about 15 mg/kg, or about 5.0 to about 20 mg/kg (or the equivalent doses expressed per square meter of body surface area). In another embodiment, a suitable dose range for oral administration, from about 10 to about 4000 mg, without adjustment for a patient's body weight or body surface area. Other effective doses may be extrapolated from dose-response curves derived from in vitro or animal model test systems. Such animal models and systems are well known in the art.

The invention also provides pharmaceutical kits comprising one or more containers containing one or more of the above-defined compounds. Optionally associated with such container(s) can be a notice in the form prescribed by a governmental agency regulating the manufacture, use or sale of pharmaceuticals or biological products, which notice reflects approval by the agency of manufacture, use or sale for human administration. In certain embodiments, the kit may also contain one or more agents useful for treating the polynucleotide repeat disorder to be administered in combination with one or more of the above-defined compounds.

Mode(s) for Carrying Out the Invention

The present invention is illustrated in further details by the following non-limiting examples.

EXAMPLE 1

Materials and Methods

C2C12 Myoblast Reporter Cell Line Assays.

C2C12 murine myoblast cells and Phoenix retrovirus packaging cells were cultivated in DMEM supplemented with 10% FBS. Phoenix cells were transfected with the desired retroviral vector by the Calcium-Phosphate method and, 48 hours after transfection, retrovirus-containing supernatant was supplemented with polybrene and deposited on cells to infect. C2C12 Tet-Off cell lines were generated by infecting cells with the retrovirus pTet-Off IN (Clontech) and selecting for Doxycycline (Dox)-regulated clones. Cell lines expressing the LacZ-5CUG, LacZ-145CUG, LUC-5CUG or LUC-200CUG transcripts were generated by infecting C2C12 Tet-Off cells with the desired reporter construct in the pRevTRE plasmid (Clontech) and selecting for stable clones with inducible expression. The 3'UTR of human DMPK containing 5 CTG repeats or 200 CTG repeats was cloned downstream of the luciferase or beta-galactosidase open reading frames. The C2C12 cell line(s) are cultivated in media containing 1 ng/ml Dox to repress transcription of the reporter constructs.

For the beta-galactosidase assay with the LacZ-145CUG and LacZ-5CUG cell lines, Dox-containing media is removed and plates are washed twice with 1×PBS, and incubated for 4 hrs in media without Dox. The cells are then trypsinised and 5,000 cells per well are plated in 100 µl of media containing 0.1 ng/ml of Dox in black 96-well plates. The next day, media is replaced with fresh media containing the compounds at the desired concentration in this manner: the media is put in a screw-cap tube and heated at 37° C. The 20 mM compound stock in 100% DMSO is pipetted directly into the media, Dox is also added to 0.1 ng/ml, and the tube is mixed well by inversion and gentle vortexing, and immediately overlayed on the cells. Pure DMSO is used for the control cells. The final concentration of DMSO is never higher than 0.5%. Stocks of compound are prepared in 100% ultra-pure tissue culture tested DMSO (SIGMA D2650), aliquoted in single use volumes to avoid freezing-thawing, and kept at −20° C. Beta-galactosidase expression is determined with the Fluorescein di(Beta-D-galactopyranoside) FDG assay. The lysis buffer is prepared as follows (for 50 ml): 15 µl Triton X-100, 5 ml HEPES 100 mM pH 7.8, and 400 µl MgSO$_4$ 8 mM. The FDG substrate (Invitrogen F1179) stock is prepared at 20 mM in a solution of dH2O/DMSO/EtOH 8:1:1. Cells are washed in 1×PBS, then lysed in 90 µl of lysis buffer, and 10 μl of 1 mM FDG (diluted in dH2O) is added for a final concentration of 100 μM. The plate is incubated at room temp for 2 hrs (protected from light) and read in fluorescence at 490 nm/515 nm.

Seven Day Treatment of DM1 Patient Myoblasts with Compounds

Human myoblasts were obtained from the Myosix institute associated with the Association Frangaise contre les Myopathies (AFM). Five primary myoblast lines were obtained as controls, and one line from a DM1 patient with a 3.8 Kb CTG triplet amplification corresponding to approximately 1250 CTG repeats. The human myoblasts are cultivated in HAM-F10 media (SIGMA N6635) with 15% FBS, 1% chick embryo extract, and 390 ng/ml of dexamethasone. One day before adding compounds, $2 \times 10^5$ cells were plated in 100 mm plates (for CUGBP1 western blot or RT-PCR alternative splicing assay) or $2 \times 10^4$ cells/well are seeded in 12-well plates containing 12 mm round glass coverslips (for FISH to detect RNA foci). One day after plating, media is replaced with fresh media containing the compounds at the desired concentration in this manner: the media is put in a screw-cap tube and heated at 37° C. The 20 mM compound stock in 100% DMSO is pipetted directly into the media and the tube is mixed well by inversion and gentle vortexing, and immediately overlayed on the cells. Pure DMSO is used for the control cells. Final concentrations on myoblasts are never higher than 0.5%. This procedure is repeated twice during the seven days of treatment, the media is thus replaced with fresh media containing compound every 2-3 days. Cells are collected or fixed for FISH after one week.

For Western blots, CUGBP1 was detected with the 3B1-3D11 monoclonal antibody (mAb) (SIGMA C5112) and GAPDH was detected with the 6C5 mAb (Millipore MAB374). The enhanced chemiluminescence signal (ECL) was acquired and quantified with the ChemiDoc™ MP imaging system (Bio-Rad). For alternative splicing assays, total RNA was collected with Trizol™ (Invitrogen), and 1 μg was used for reverse transcription with random primers with the RevertAid™ H Minus M-MuL RT (Fermentas) according to manufacturer's instructions. For MBNL2, PCR amplification was performed with primers 5'-ACAAGTGACAACACCGTAACCG-3' (SEQ ID NO:1) and 5'-TTTGGTAAAGGATGAAGAGCACC-3' (SEQ ID NO:2). SERCA1 was amplified with primers 5'-ATGATCT-TCAAGCTCCGGGC-3' (SEQ ID NO:3) and 5'-CA-GCTCTGCCTGAAGATGTG-3' (SEQ ID NO:4). For TNNT2 (cardiac Troponin T), PCR was carried out with primers 5'-ATAGAAGAGGTGGTGGAAGAGTAC-3' (SEQ ID NO:5) and 5'-GTCTCAGCCTCTGCTTCAG-CATCC-3' (SEQ ID NO:6). The alternative splicing of the hnRNPA2/B1 transcript was detected with the primers 5'-CTGAAGCGACTGAGTCCGCG-3' (SEQ ID NO:7) and 5'-ACAGTCTGTAAGCTTTCCCC-3' (SEQ ID NO:8). PCR was performed with Taq using standard conditions but the number of amplification cycles was optimized to be in the quantitative range for each gene. The products of PCR amplification were resolved on 3.5% agarose gels containing Gelred™ (Biotium) and images were acquired and quantified with the ChemiDoc™ MP imaging system (Bio-Rad).

Detection and Quantification of CUG-triplet Repeat RNA Foci

For fluorescent in situ hybridization (FISH), cells grown on glass coverslips were fixed in PBS containing 4% paraformaldehyde, dehydrated for 2 hours in 70% ethanol, and incubated overnight with 10 ng of probe in 2×SSC 40% formamide at 37° C. The next day, coverslips were washed twice in 2×SSC 40% formamide, treated with DAPI, and mounted in glycerol:PBS:PPD mounting media. To visualize CUG-triplet repeat mRNA foci, a single probe with the sequence $(CAG)_{10}$ was labelled with Cy3 and used for FISH. A control Cy3-labelled probe with the sequence $(CTG)_{10}$ gave no hybridization signal in DM1 patient myoblasts. Images for FISH were acquired on an epifluorescence light microscope with a 1.40 NA 60× oil objective and a CCD camera. For each field of cells, six image Z-stacks with 0.5 μm steps were acquired with Cy3 and DAPI filter cubes. To quantify the CUG repeat RNA aggregates, the 3D images of the foci were first processed by maximum intensity projection with the MetaMorph™ software (Molecular Devices Inc.), resulting in a 2D image containing all the foci in each cell. A script was developed with MetaMorph™ to first outline the nuclei using the DAPI images, then threshold the CUG-repeat RNA foci in the nuclei to define them, and finally sum the surface area covered by the nuclear RNA foci in each nucleus. The threshold value for the CUGn RNA foci was determined by obtaining the average value for background nucleoplasmic fluorescence when WT human myoblasts are hybridized with the $(CAG)_{10}$-Cy3 probe (this background fluorescence signal is a combination of non-specific hybridization of the probe, autofluorescence of the cells and camera background). The MetaMorph™ program then calculates the surface area covered in each nucleus for all the foci in the Cy3 image that have a) pixels with a fluorescence value above the threshold, and b) a size larger than 3 pixels (to remove single pixel background). For each treatment condition, 60 to 80 cells were analyzed and all the data points were presented, with the median value indicated. Each experiment was repeated at least three times.

EXAMPLE 2

Identification of Two "Hit" Compounds by High-throughput Screening

A high-throughput screen (HTS) of chemical compounds was performed in order to identify and validate drug candidates that relieve the nuclear retention of CUGn mRNAs and dislocate nuclear foci formation in a DM1 cell culture model. For that screen, a reporter mRNA containing a luciferase ORF with the DMPK 3' untranslated region containing 200 CUG repeats was used as a model system for DM1. This allowed the screening of a comprehensive library of 110,000 small molecules (Maybridge™ Screening collection and Specs™ screening library) for effectors on CUGn mRNA nuclear retention and RNA foci formation. In a secondary screen, fluorescent in situ hybridization (FISH) was used to visualize the disruption of the nuclear CUG-rich RNA foci. From these screens, two chemical compounds which: 1) increase nuclear export and translation of reporter mRNAs containing expanded CUG triplet repeats, and 2) decrease the number and intensity of nuclear CUGn RNA foci, were identified.

EXAMPLE 3

Characterization of the Two "Hit" Compounds

Figure 3:
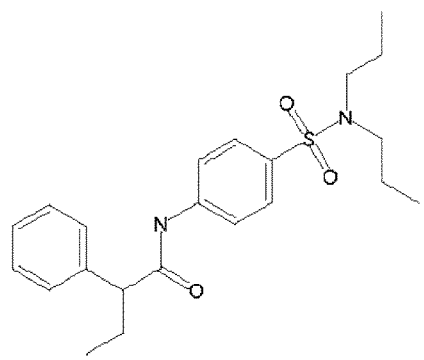
FIG. 3 shows the structure of two compounds (compounds #15 and 32) identified in the first screening experiments.
Figure 3:
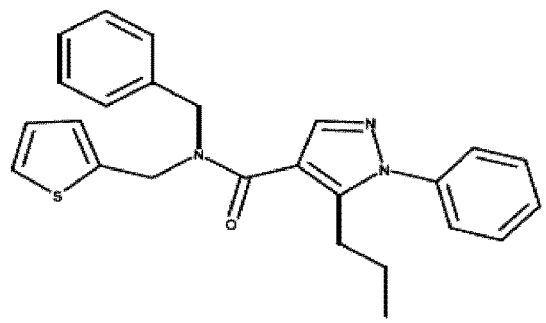

The two compounds identified by the screening assay described above, which were named compound 15 and 32, have the structure depicted in FIG. 3. Compound 15 has a para-sulfonamide structure, and compound 32 is a benzyl methylthiophene amide. Both are small molecules which fit the Lipinski's "rule of five" for drug-like properties (C. A.

Lipinski; F. Lombardo; B. W. Dominy and P. J. Feeney (2001). *Adv Drug Del Rev* 46: 3-26) and should thus demonstrate good ADME (absorption, distribution, metabolism and excretion) profiles. The dose-response effect of candidate drugs 15 and 32 on the nuclear export of luciferase-CUG200 mRNA was assessed in the C2C12 myoblast cell line. The amount of CUG repeat RNA that get exported and properly translated into luciferase in response to treatment with varying concentrations of target drugs was measured in order to determine the dose-response curves. The data show that, for compound 15, the plateau of maximal effect was reached at 15 µM ($EC_{50}$=6.8 µM), while a maximal effect peak was reached at 5 µM ($EC_{50}$=2.5 µM) for compound 32.

EXAMPLE 4

Reduction of CUG-rich RNA Foci Formation in DM1 Patient Myoblasts

Figures 4, 5:
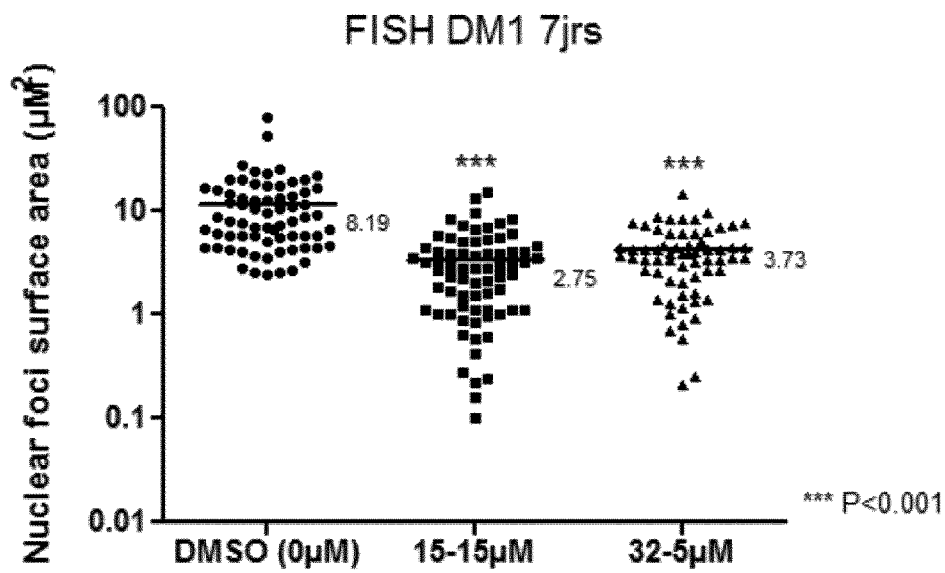
FIG. 4 shows that compounds #15 and 32 reduce the formation of mutant DMPK mRNA foci in DM1 patient myoblasts. Myoblast cells with 1250 CTG-repeats in the 3'UTR of the DMPK gene were treated with compounds 15, 32 or DMSO for 7 days. The formation of (CUG) n RNA foci was detected by FISH. The surface occupied by CUG-repeat RNA foci in the nucleus of the DM1 myoblasts was quantified with the Imaris™ program. Each data point represents one nucleus and the median value is shown on the graph. ***p<0.001.
FIG. 5 shows a structure-activity relationship (SAR) analysis of analogues of compounds 15 and 32. A screen of 49 analogues of compounds 15 and 32 was performed in C2C12 myoblasts expressing a LacZ-145CUG reporter mRNA. Sixteen analogues increase the beta-galactosidase activity in the reporter cell line (table). $EC_{50}$ assays of the analogue compounds show that they increase the expression of the beta-galactosidase expressed from the LacZ-145CUG mRNA, but not from the LacZ-5CUG mRNA. The cells were treated with 0.2, 1, 2, 5 and 25 µM concentrations of each compound for 24 hrs. The $EC_{50}$ and maximal induction of beta-galactosidase (Max) were measured for each compound.

To confirm the activity of these compounds on an endogenous target, the ability of the two chemical compounds to disrupt RNA foci formation in myoblasts from a patient with DM1 was verified. The DM1 myoblasts with approximately 1250 CTG triplets in the DMPK gene were treated for 7 days with 15 µM of compound 15 or 5 µM of compound 32, compared to the control (DMSO only). Using DAPI staining and fluorescent in situ hybridization (FISH) with a probe against CUG-repeat RNA, the surface occupied by RNA foci in the nucleus was measured with the MetaMorph™ software, which provides a quantitative measurement of the amount of CUG-repeat mRNA aggregated and retained in a given nucleus. A detailed description of the FISH and foci quantification procedures is included in the section entitled "*Detection and quantification of CUG-triplet repeat RNA foci*" of Example 1 (Materials and methods). As shown in FIG. 4, a more than two-fold decrease in RNA foci formation was observed in DM1 myoblasts for both compounds. These experiments were repeated several times, with similar results. These results confirm the inhibitory effect of the hit compounds on the formation of CUG-rich RNA foci in myoblasts from DM1 patient, which express endogenous DMPK transcripts with a large expansion of CUG triplets.

EXAMPLE 5

Structure-activity Relationship (SAR) Analysis of Compounds 15 and 32

A screen of small-molecules structurally similar to compounds 15 and 32 isolated in our original high-throughput screen was performed. 49 compounds that are structural analogues of compound 15 or 32 were chosen. These are shown in the tables below:

Analogues of compound 15

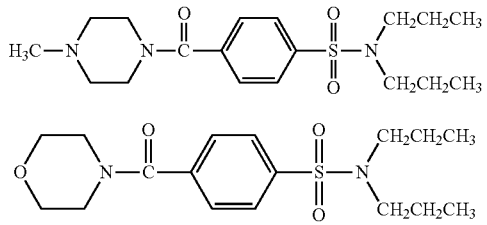

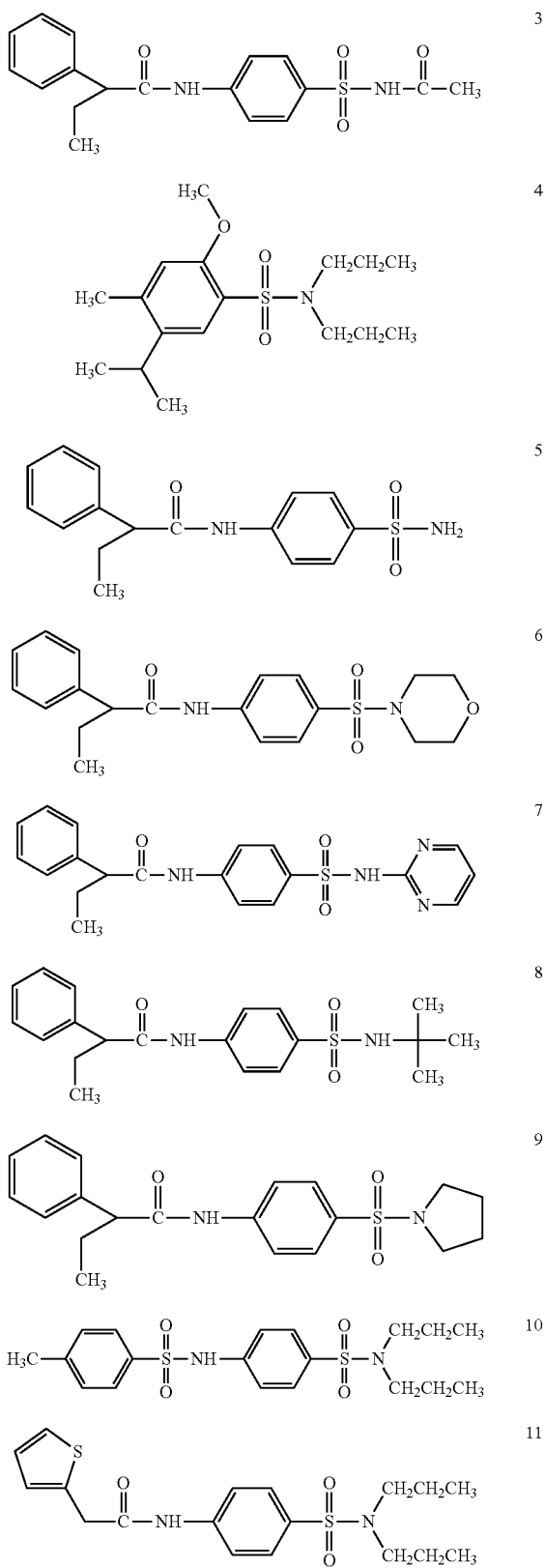

Analogues of compound 15
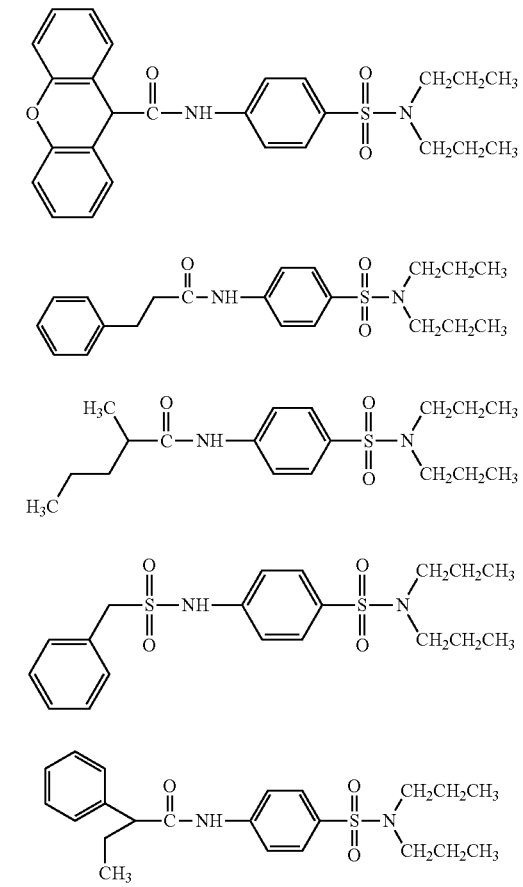
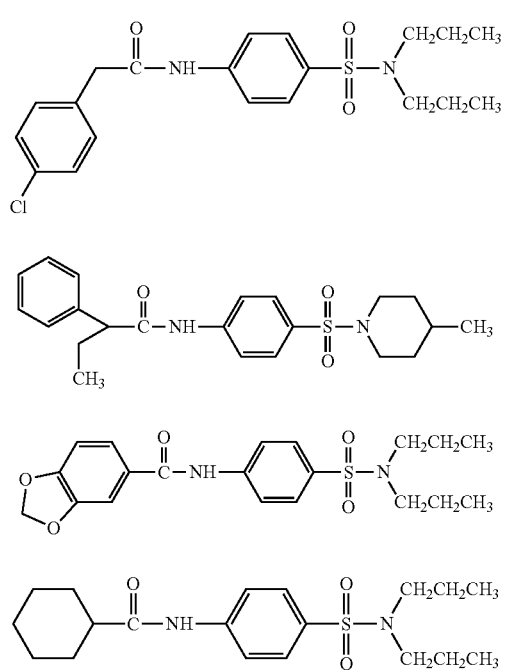
Identical to original "compound 15"
Analogues of compound 15
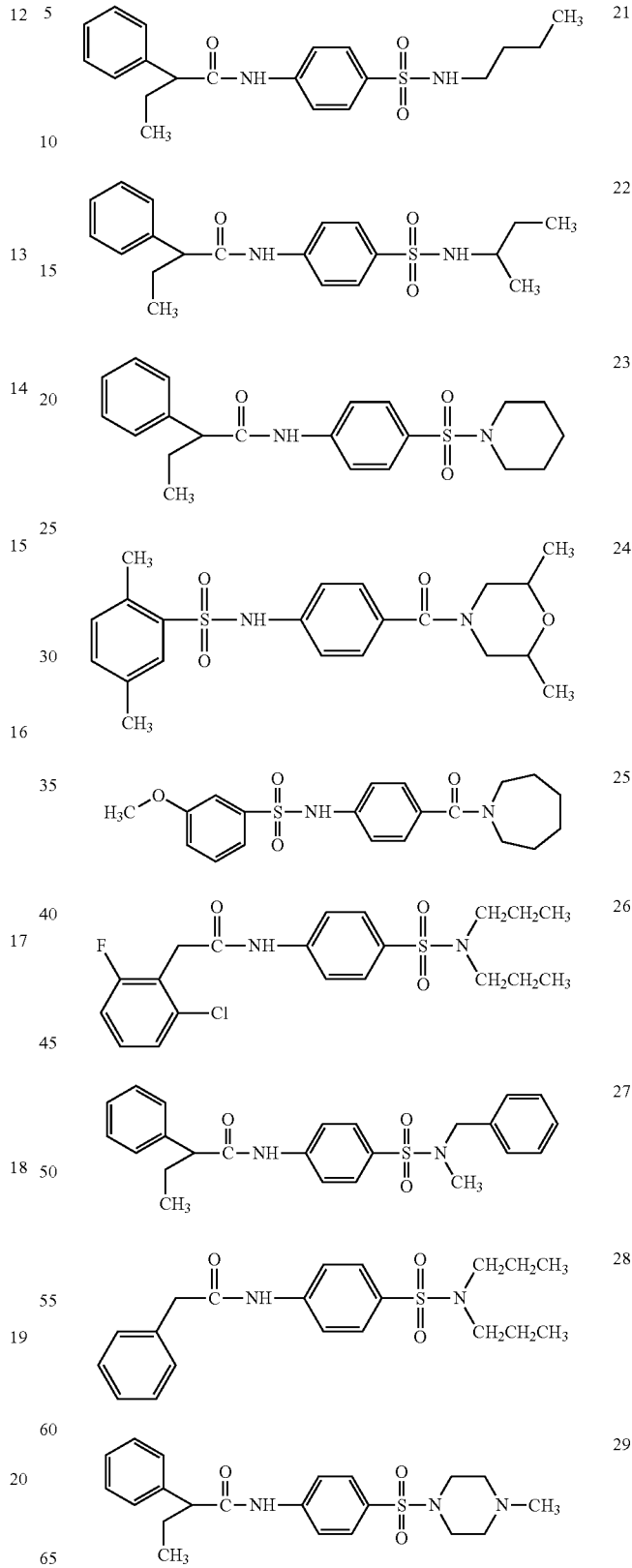

Analogues of compound 15
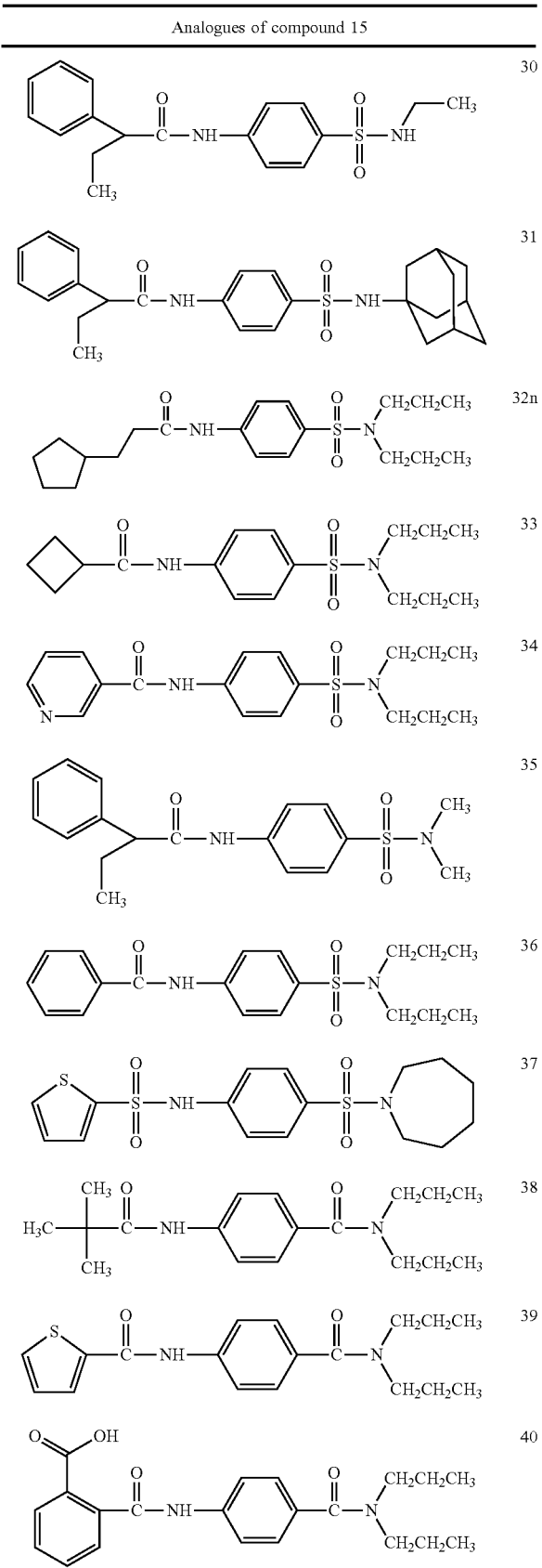
Analogues of compound 15
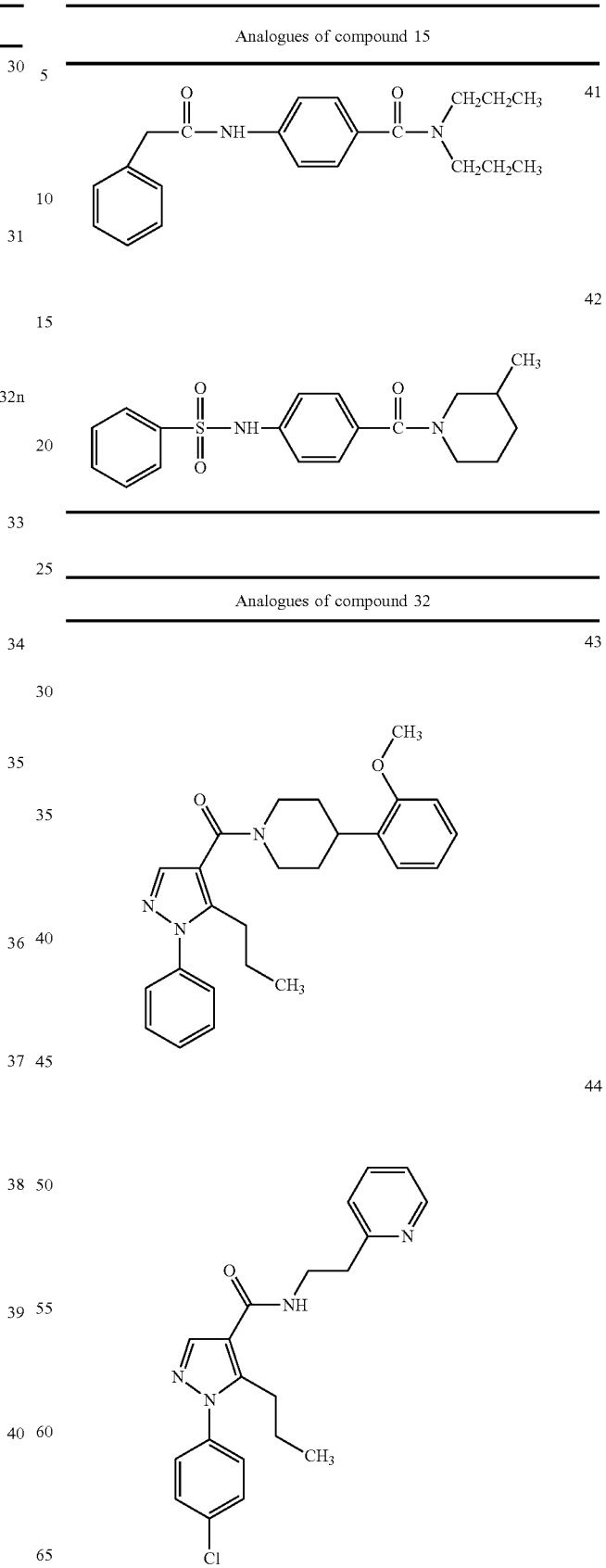
Analogues of compound 32

| Analogues of compound 32 |
|---|
| 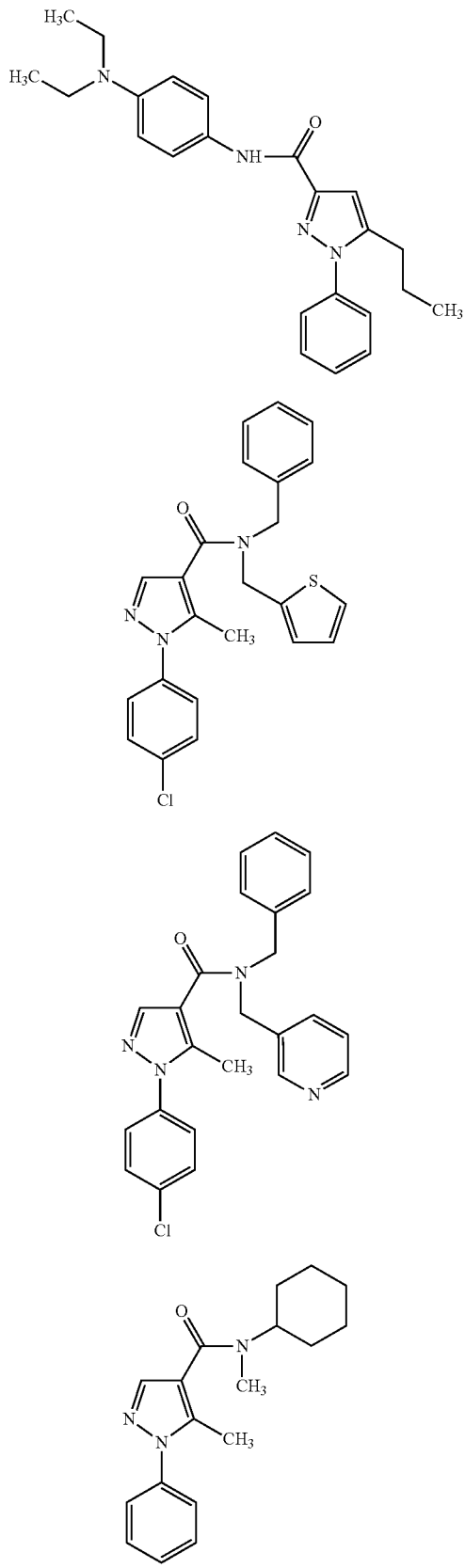 45<br>46<br>47<br>48 |

| Analogues of compound 32 |
|---|
| 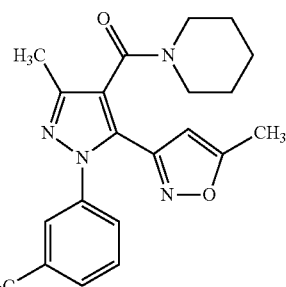 49 |

Figure 6A:
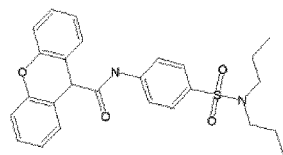
FIGS. 6A and B shows the structure of analogues of compounds #15 (FIG. 6A) and 32 (FIG. 6B) identified in the SAR analysis described in FIG. 5.
Figure 6A:
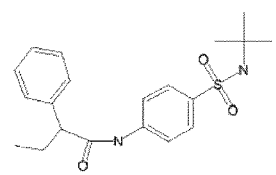
Figure 6A:
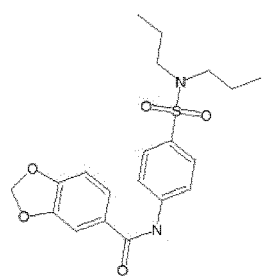
Figure 6A:
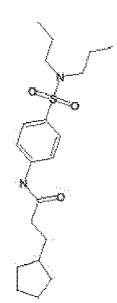
Figure 6A:
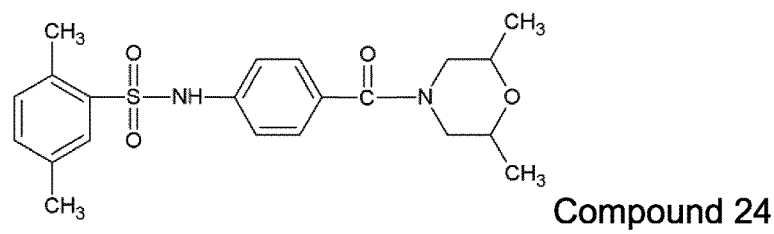
Figure 6A:
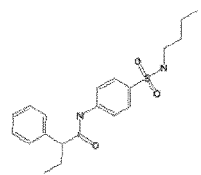
Figure 6A:
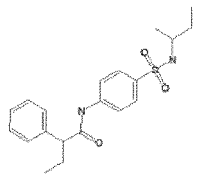
Figure 6A:
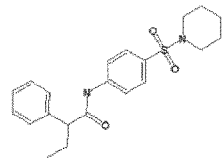
Figure 6A:
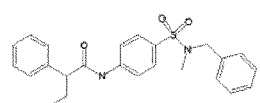
Figure 6A:
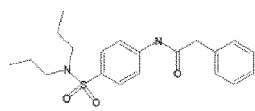
Figure 6A:
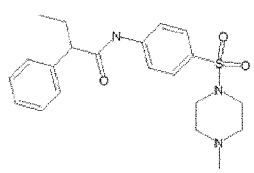
Figure 6A:
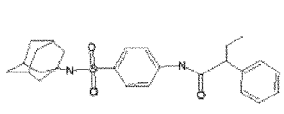
Figure 6A:
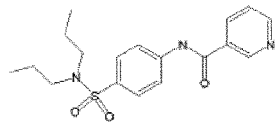
Figure 6A:
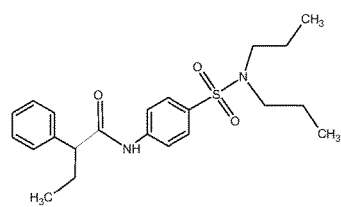
Figure 6B:
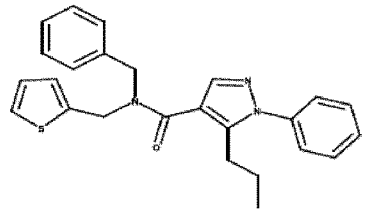
FIG. 6C shows further analogs (no. 102, 195, 196, 213, 214, 215, 216, 217, 218, 219, 220, 221) of these compounds.
Figure 6B:
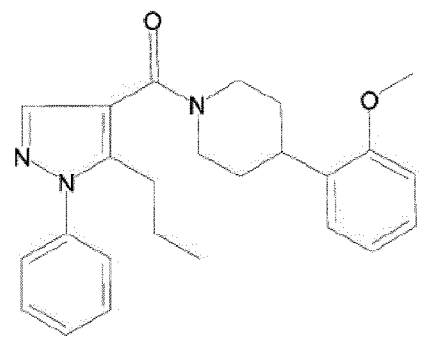
Figure 6B:
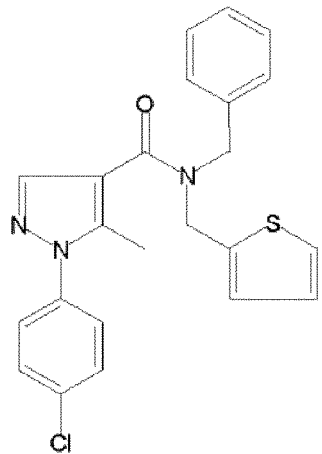

These analogous compounds allowed testing the structure-activity relationship of compounds 15 and 32. From this screen, 15 new hit compounds that increased β-galactosidase activity nearly two-fold in C2C12 myoblasts expressing the LacZ-145CUG reporter mRNA, and had no effect on activity from the LacZ-5CUG mRNA control cell line, were identified (FIG. 5). Twelve of these new compounds are related to drug candidate 15, and two are similar to drug candidate 32 (chemical structures shown in FIGS. 6A and B).

EXAMPLE 6

Synthesis of Further Analogs

Figure 6C:
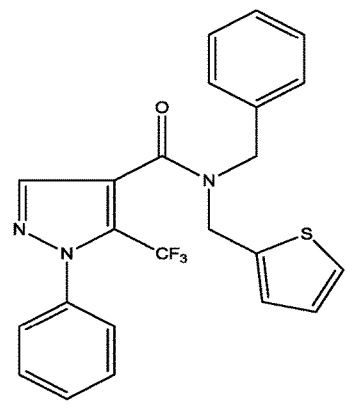
Figure 6C:
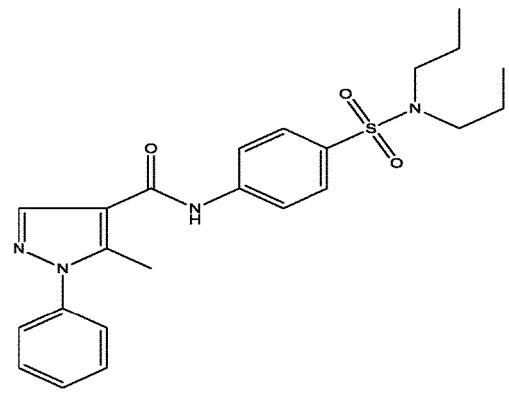
Figure 6C:
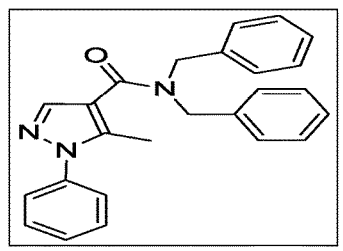
Figure 6C:
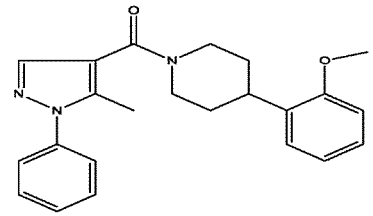
Figure 6C:
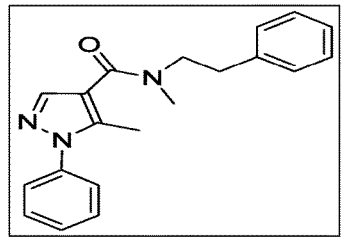
Figure 6C:
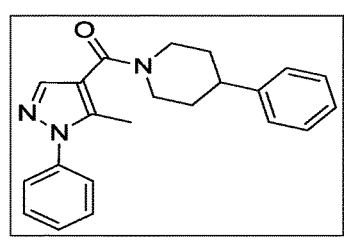
Figure 6C:
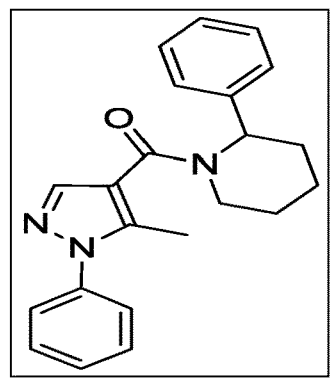
Figure 6C:
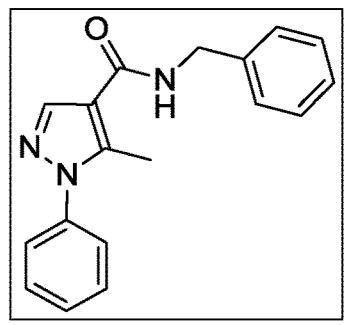
Figure 6C:
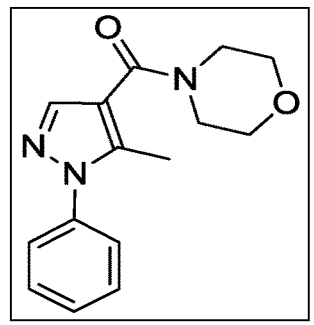
Figure 6C:
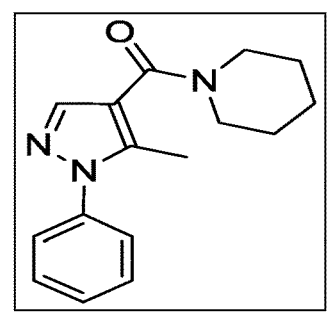
Figure 6C:
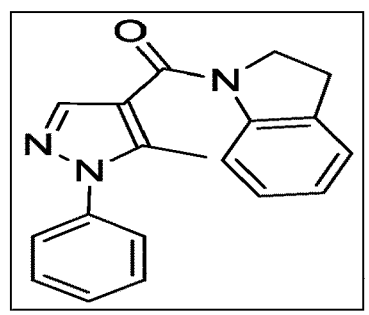
Figure 6C:
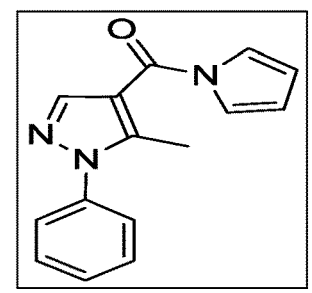

Other analogues as depicted in FIG. 6C, including a "chimera" of both compounds 15 and 32, were synthesized.
Synthetic methods for preparing these compounds are illustrated below. Starting materials are commercially available or may be prepared according to procedures known in the art or as illustrated herein.

All temperatures are in degrees Celsius. Mass spectra (MS) were measured by electrospray ion-mass spectroscopy (ESI) on an Agilent 6120 Quadrapole™ MS coupled to an Agilent 1100™ series HPLC instrument. NMR spectra were recorded on a Varian Mercury spectrometer at 400 MHz for $^1$H and 376 MHz for $^{19}$F.

The following abbreviations have the indicated meanings:
AcOH=acetic acid
Alk=alkyl
Ar=aryl
atm=atmosphere
BINAP=2,2'-bis(diphenylphosphino)-1,1'-binaphthalene
Boc=tert-butoxycarbonyl
n-BuLi=n-butyllithium
Cbz=carboxybenzyl
$CH_2Cl_2$=dichloromethane
DBU=1,8-diazabicyclo[5.4.0]undec-7-ene
DEAD=diethyl azodicarboxylate
DIPEA=N,N-diisopropylethylamine
DMAP=4-(dimethylamino)pyridine
DMF=N,N-dimethylformamide
DMSO=dimethyl sulfoxide
ESI=electrospray ionization
$Et_3N$=triethylamine
$Et_2O$=diethylether
EtOAc or EA=ethyl acetate
EtOH=ethyl alcohol
h=hour(s)
$H_2$=hydrogen HATU=O-(7-azabenzotriazol-1-yl)-N,N,N',N'-tetramethyluronium hexafluorophosphate
HCl=hydrochloric acid
HPLC=High Pressure Liquid Chromatography
iPrOH=2-propanol
KF=potassium fluoride
LC-MS=Liquid Chromatography Mass Spectrometry
LiOH=lithium hydroxide
MeCN=acetonitrile
MeMgBr=methylmagnesium bromide
MeOH=methyl alcohol
MeTHF=2-methyltetrahydrofuran
MgSO$_4$=magnesium sulfate
min=minute(s)
MS=mass spectroscopy
MTBE=methyl tert-butyl ether
N$_2$=nitrogen
NaBH$_4$=sodium borohydride
NaHCO$_3$=sodium bicarbonate
NaOH=sodium hydroxide
Na$_2$SO$_4$=sodium sulfate
NH$_3$=ammonia
NH$_4$Cl=ammonium chloride
NH$_4$OH=ammonium hydroxide
NMP=N-methyl 2-pyrrolidinone
NMR=nuclear magnetic resonance spectroscopy
Moc=methoxycarbonyl
P=pressure
Pd/C=palladium on charcoal
PG=protecting group
Ph=phenyl
Pyr=pyridine
rbf=round bottom flask
Rf=retention factor on silica gel
rt=room temperature
TBDMS=tert-butyldimethylsilyl
Ts=toluene-4-sulfonyl
TFA=trifluoroacetic acid
TFAA=trifluoroacetic anhydride
TFA-NHS=trifluoroacetic N-hydroxysuccinimide
THF=tetrahydrofuran
TLC=thin layer chromatography
TMEDA=N,N,N',N'-tetramethylethylenediamine
T3P=Propylphosphonic anhydride General Sequence 1:

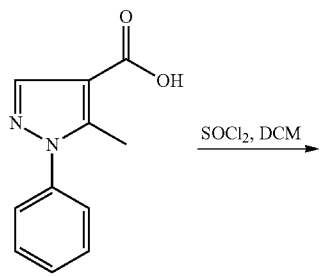

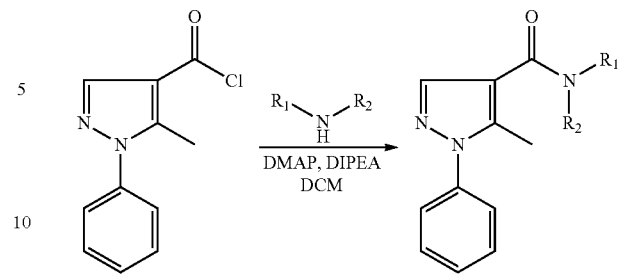

Step 1: Thionyl chloride (0.90 mL, 12 mmol, 5.0 eq.) was added dropwise to a stirred suspension of 5-methyl-1-phenyl-1H-pyrazole-4-carboxylic acid (0.5 g, 2.5 mmol; prepared according to Dycman et al. WO 2004/099156) in DCM (5.0 mL) at 00° C. The reaction was subsequently warmed to rt and stirred for an additional 6 hours before being concentrated to dryness under high vacuum. The residue was used directly in the next step.

Step 2: DIPEA (2.0 eq.) was added to a solution of the product from Step 1, an appropriate secondary amine (1.2 eq.) and DMAP (0.1 eq.) in DCM (0.2 M). The reaction was stirred at rt for 3 hours before being concentrated to dryness and the residue purified directly by flash chromatography on silica gel eluting with an increasing proportion of EtOAc in hexanes.

N,N-Dibenzyl-5-methyl-1-phenyl-1H-pyrazole-4-carboxamide (Compound 214)

Prepared as a colorless gum using dibenzylamine in General Sequence 1.

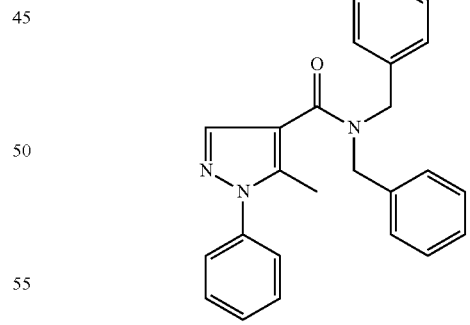

$^1$H NMR (CDCl$_3$) δ 7.58 (1H), 7.52-7.21 (15H), 4.70 (4H), 2.50 (3H). MS ESI: 382.2 [M+H]$^+$.

Indolin-1-yl(5-methyl-1-phenyl-1H-pyrazol-4-yl)methanone (Compound 220)

Prepared as a colorless gum using 2,3-dihydro-1H-indole in General Sequence 1.

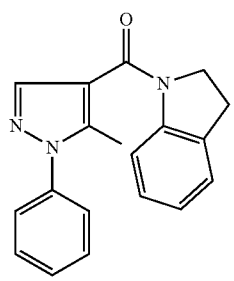 [SMILES: Cc1c(C(=O)N2CCc3ccccc32)cnn1-c1ccccc1]

¹H NMR (CDCl₃) δ 7.83 (1H), 7.54-7.49 (2H), 7.48-7.44 (3H), 7.25-7.18 (3H), 7.04 (1H), 4.31 (2H), 3.19 (2H), 2.52 (3H). MS ESI: 304.2 [M+H]⁺.

N-(4-(N,N-Dipropylsulfamoyl)phenyl)-5-methyl-1-phenyl-1H-pyrazole-4-carboxamide (Compound 196)

Reaction Sequence:

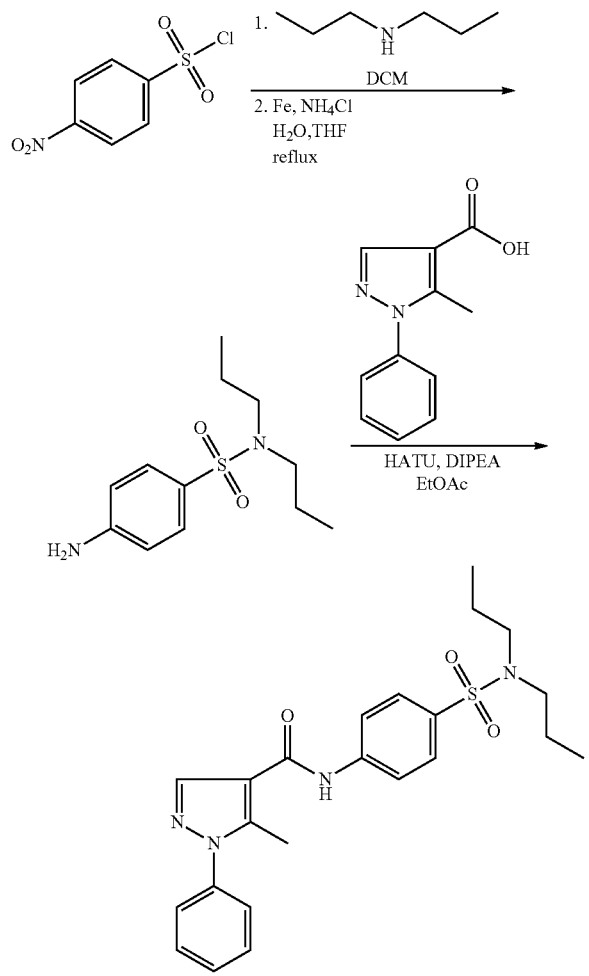

Step 1: Dipropylamine (1.9 mL, 14 mmol, 3.0 eq.) was added dropwise to a suspension of 4-nitrobenzenesulfonyl chloride (1.0 g, 4.5 mmol) in DCM (15 mL) at 00° C. After 10 minutes at 0° C., the reaction was stirred at rt for 2 hours before being partitioned between water and DCM. The layers were separated and the aqueous layer was extracted with DCM (2×). The combined organic layers were dried (MgSO₄), filtered and concentrated under reduced pressure and the residue was purified by flash chromatography on silica gel eluting with an increasing proportion of EtOAc in hexanes.

Step 2: A saturated solution of NH₄Cl (0.5 mL) and iron powder (0.59 g, 10 mmol, 10 eq.) were added to a solution of the product from Step 1 (0.30 g, 1.0 mmol) in EtOH (4.0 mL). The mixture was heated at 65° C. for 18 hours before being cooled to rt and partitioned between EtOAc and water. The layers were separated and the aqueous layer extracted with EtOAc (3×). The combined organics layers were dried (MgSO₄), filtered, concentrated and dried under suction and high vacuum to afford 4-amino-N,N-dipropylbenzenesulfonamide which was used directly without further purification.

Step 3: The product from Step 2 (42 mg, 0.16 mmol, 1.2 eq.) was added to a solution of 5-methyl-1-phenyl-1H-pyrazole-4-carbonyl chloride (30 mg, 0.14 mmol) and DIPEA (48 μL, 0.27 mmol, 2.0 eq.) in DCM (0.68 mL). The reaction was stirred at rt for 18 hours before being concentrated to dryness. The residue was purified by flash chromatography on silica gel eluting with an increasing proportion of EtOAc in hexanes to afford the title compound as a yellow solid.

¹H NMR (DMSO-d6): δ 10.19 (1H), 8.35 (1H), 7.96 (2H), 7.76 (2H), 7.61-7.49 (5H), 3.03-2.99 (4H), 2.56 (3H), 1.48-1.40 (4H), 0.85-0.77 (6H). MS ESI: 463.2 [M+Na]⁺.

N-Benzyl-1-phenyl-N-(thiophen-2-ylmethyl)-5-(trifluoromethyl)-1H-pyrazole-4-carboxamide (Compound 102)

Reaction Sequence:

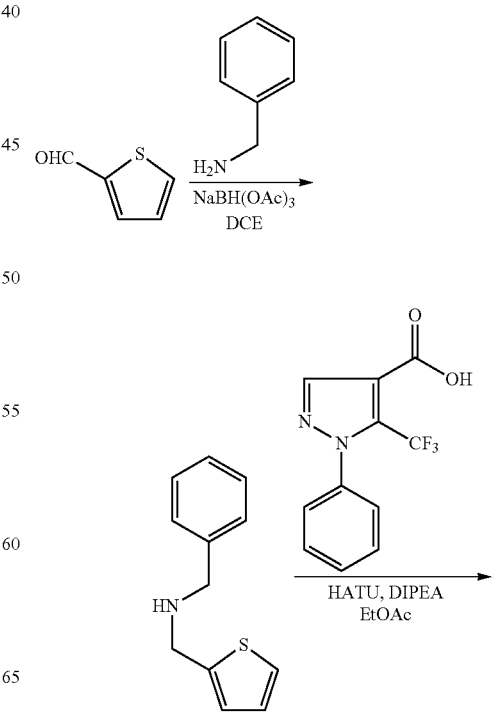

-continued

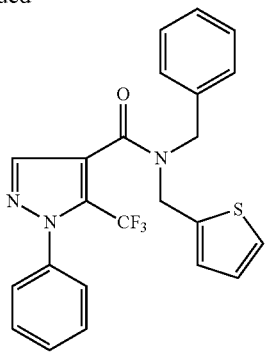

Step 1: Benzylamine (3.8 mL, 35 mmol, 1.05 eq.) and acetic acid (9.6 mL, 170 mmol, 5 eq.) were added to a solution of 2-thiophenecarboxaldehyde (3.1 mL, 34 mmol) in DCE (110 mL) with stirring at rt for 18 hours. Sodium triacetoxyborohydride (8.95 g, 42.3 mmol, 1.2 eq.) was then added with continued stirring at rt for an additional hour. The reaction vessel contents were then cooled to 0° C. and a saturated solution of NaHCO$_3$ was added slowly to pH 8. Following cessation of the evolution of hydrogen gas, the layers were separated and the aqueous layer was extracted with DCM (3×). The combined organic layers were dried (MgSO$_4$), filtered and concentrated under reduced pressure. The residue was purified by flash chromatography of the residue on silica gel eluting with an increasing proportion of EtOAc in hexanes.

Step 2: DIPEA (96 µL, 0.55 mmol, 3.0 eq.) was added to a suspension of 1-phenyl-5-(trifluoromethyl)-1H-pyrazole-4-carboxylic acid (50 mg, 0.20 mmol, 1.05 eq.), the product from Step 1 (38 mg, 0.19 mmol) and HATU (81 mg, 0.21 mmol, 1.2 eq.) in EtOAc (2.0 mL). The mixture was stirred for 18 hours before being partitioned between EtOAc and a saturated solution of NaHCO$_3$. The layers were separated and the aqueous layer extracted with EtOAc (3×). The combined organic layers were dried (MgSO$_4$), filtered and concentrated under reduced pressure. The product was isolated as a colorless solid by flash chromatography on silica gel eluting with an increasing proportion of EtOAc in hexanes.

$^1$H NMR (DMSO-d6): δ 7.84 (0.45H), 7.70 (0.55H), 7.54-7.26 (10H), 7.23-7.18 (1H), 7.02-6.94 (1.55H), 6.90-6.86 (0.45H), 4.86 (1.1H), 4.79 (0.9H), 4.58 (0.9H), 4.54 (1.1H). MS ESI: 464.2 [M+Na]$^+$.

EXAMPLE 7

Figure 7:
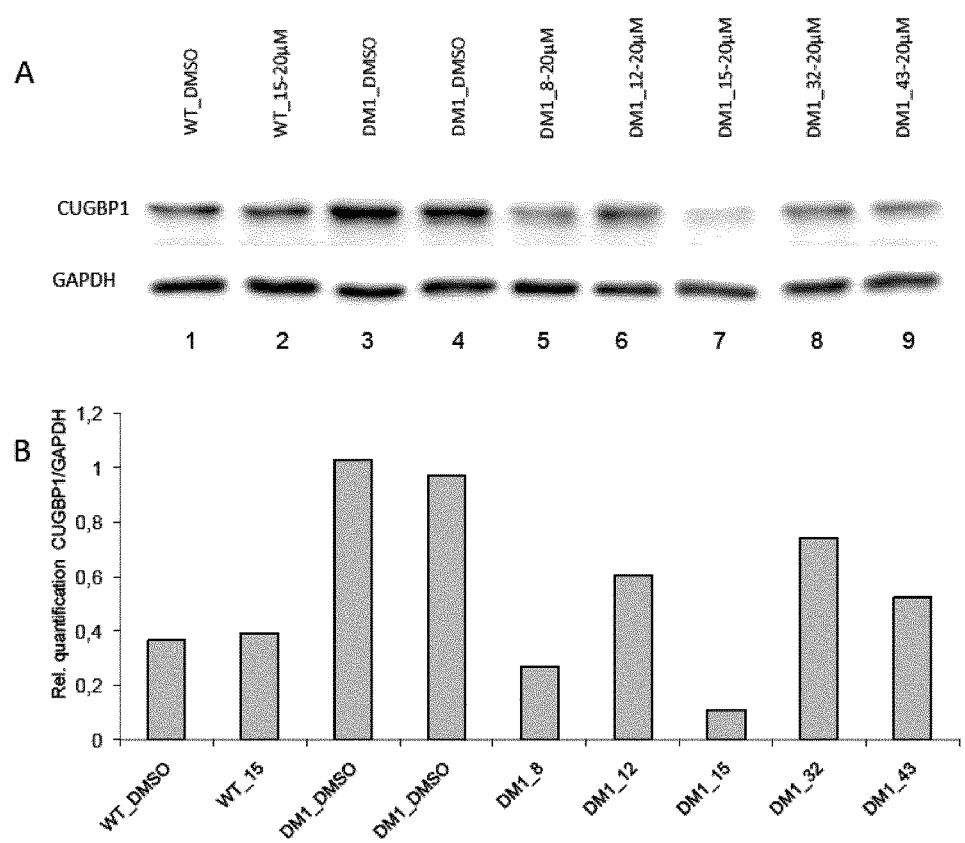
FIG. 7 shows the effect of compounds #15 and 32 and representative analogues thereof on the levels of the CUGBP1 alternative splicing factor. (A) Western blot on the CUGBP1 protein in normal human myoblasts (WT) and DM1 patient myoblasts treated with compound 15 (and its analogues 8 and 12), or compound 32 (and its analogue 43) at a concentration of 20 µM for 7 days. (B) Quantification of the bands in panel (A) acquired with the ChemiDoc™ MP imaging system (Bio-Rad). GAPDH is used as a loading control.

Effect of Disruption of CUG-rich RNA Foci on Expression of Splicing Factors and mRNA Splicing A primary consequence of RNA toxicity in DM1 is dysfunction of two classes of splicing regulators: the CUG binding protein 1 (CUGBP1/CELF1) and the muscleblind protein 1 (MBNL1). MBNL1 recognizes YGCY motifs in RNA and binds with high affinity to CUG repeats (Goers et al. 2010). MBNL1 has been shown to co-localize in vivo with the nuclear foci of CUG-triplet repeat transcripts (Fardei et al. 2001), suggesting that the sequestration of this factor in the nucleus may lead to DM1 pathogenesis. Expanded CUG-repeat RNA is believed to increase CUGBP1 levels and activity in DM1 cells via activation of protein kinase C (PKC), which phosphorylates and stabilizes CUGBP1 protein levels (Kuyumcu-Martinez et al. 2007). CUGBP1 was found to bind CUG-repeat RNA but does not co-localize in vivo with the nuclear DMPK expanded-repeat foci (Fardei et al. 2001). It was next tested whether treatment of DM1 patient myoblasts with compounds 15 and 32 and representative analogues thereof could correct the increased CUGBP1 protein levels observed in these cells (FIG. 7). Western Blot analyses show that DM1 cells have a level of CUGBP1 about 2.5-times higher than WT cells (lane 1 compared to lanes 3 and 4). The myoblast cells were treated for 7 days at a 20 µM concentration of the compounds or DMSO. As a control, it was verified that the treatment of WT cells with compound 15 does not change the levels of CUGBP1 (lane 2 compared to lane 1). Treatment of the DM1 myoblasts with compound 15 reduces CUGBP1 levels by 85% (lane 7 compared to lanes 3 and 4). Compounds 32 and 43 also reduce CUGBP1 levels by 30% and 45%, respectively (lanes 8 and 9 compared to lanes 3 and 4). Thus, the drug candidates have the capacity to correct the stabilization of the CUGBP1 alternative splicing factor in DM1 myoblasts. The abnormal increase in CUGBP1 levels has been linked to the severe muscle wasting which debilitates DM1 patients in advanced stages of the disease (Orengo et al. 2008).

Figure 8:
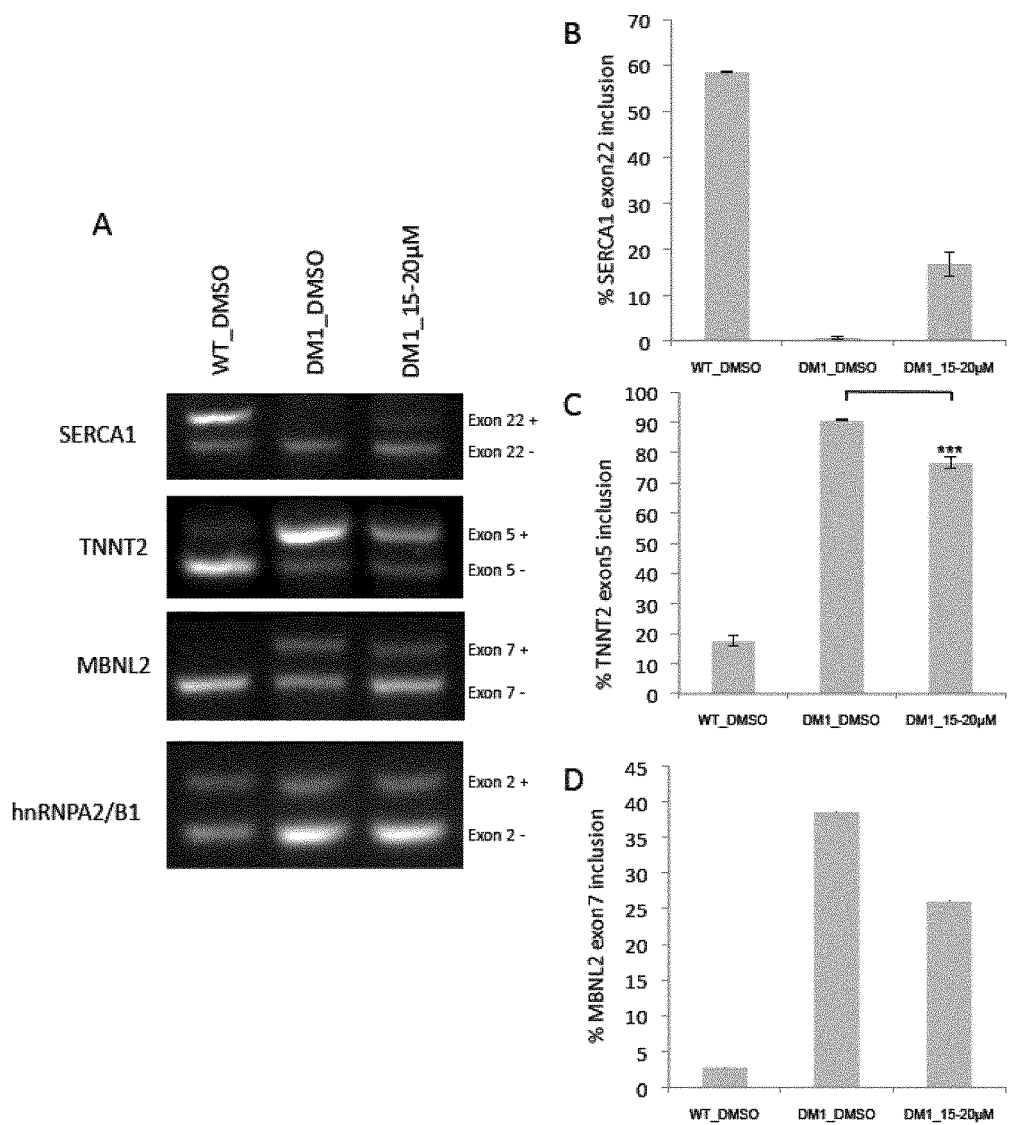
FIG. 8 shows the effect of compound 15 on the alternative splicing of three transcripts mis-spliced in DM1. Normal human myoblasts (WT) or myoblasts from a DM1 patient were treated with compound 15 at 20 µM or DMSO during 7 days. (A) RT-PCR on endogenous SERCA1, TNNT2 and MBNL2 mRNA (hnRNPA2/B1 is used as a negative control). Quantification of the percentage of exon inclusion tested for SERCA1 (B), TNNT2 (C) and MBNL2 (D). *** P<0.001.

The effect of treatment with candidate drugs 15 and 32 on the alternative splicing of specific mRNA, such as SERCA1 exon 22, TNNT2 exon 5, and MBNL2 exon 7, which are all mis-spliced to re-express a foetal or neonatal form in DM1 cells, was tested. Patient myoblasts were treated for 7 days with a 20 µM concentration of candidate drugs. Total RNA was extracted, and used in RT-PCR reactions to quantify the splicing of the endogenous mRNA. SERCA1 (ATP2A1) is a sarcoplasmic/ER Ca$^{2+}$-ATPase expressed in skeletal muscle. As shown in FIG. 8B, SERCA1 exon 22 inclusion changes from 59% in the WT cells, to less than 2% in the DM1 myoblasts. Treatment with compound 15 restores inclusion of exon 22 to 17% of total transcripts. The SERCA1 exon 22+ variant is the adult form, and the SERCA1 exon 22− is the neonatal form (Kimura et al. 2005). Mis-splicing of SERCA1 is thought to be involved in muscle wasting in DM1. The data depicted in FIG. 8C shows that treatment with candidate compound 15 reduces the inclusion of foetal TNNT2 exon 5 from 90% to 76% of total transcripts. Mis-splicing of this exon 5 of cardiac Troponin T (TNNT2/cTNT) causes cardiac conduction defects in DM1 (Ho et al. 2005, Warf et al. 2009). MBNL2 is a muscleblind splicing regulator that is ubiquitously expressed. In FIG. 8D, it is shown that treatment with compound 15 reduces the inclusion of exon 7 from 40% to 25%. Mis-splicing of MBNL2 is thought to result in the mis-splicing of several transcripts in the brain in DM1 (Charizanis et al. 2012).

Figure 9:
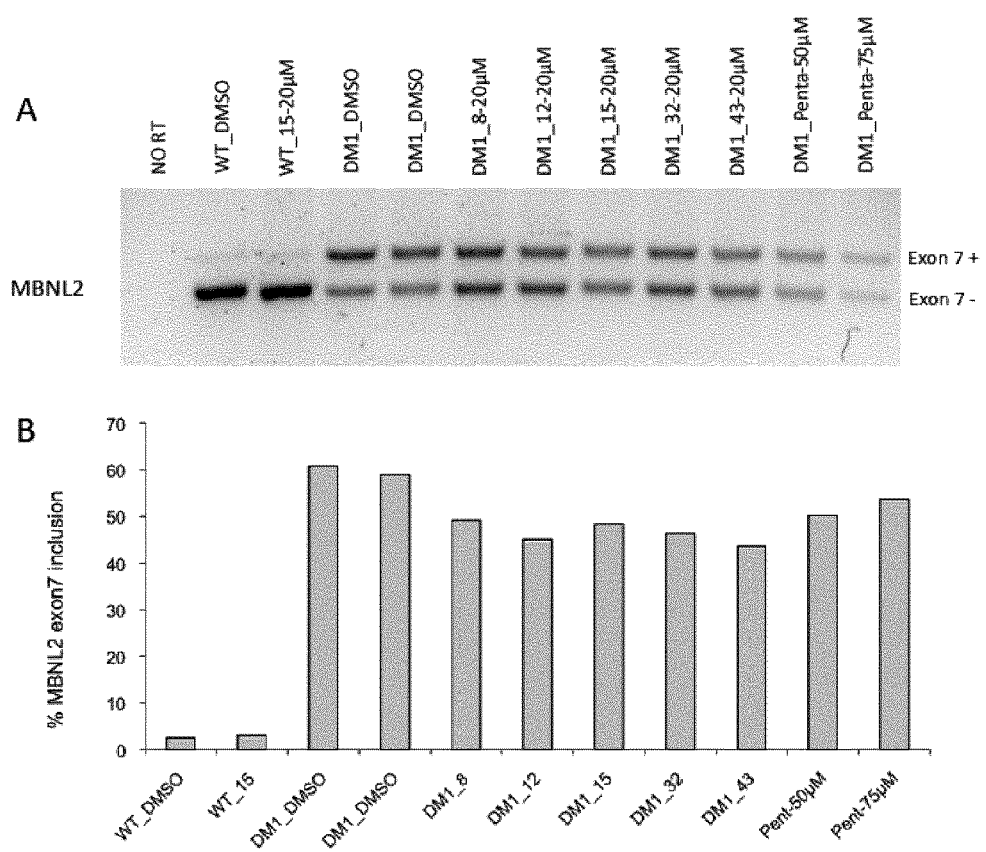
FIG. 9 shows the effect of compounds #15 and 32 and representative analogues thereof on the alternative splicing of the endogenous MBNL2 transcript. Normal human myoblasts (WT) or myoblasts from a DM1 patient, were treated with DMSO, compound 15 (or analogues 8 or 12), or compound 32 (or analogue 43) at 20 µM concentration during 7 days. Pentamidine treatment was done at a 50 µM concentration for 16 hours or at 75 µM for only 12 hours, due to the toxicity of this compound. (A) RT-PCR on the MBNL2 mRNA. (B) Quantification of the percentage of inclusion of exon 7 (band 7+/band 7++band 7−)*100.

Compounds 15 and 32, and some of their analogues, were tested for the correction of MBNL2 exon 7 mis-splicing. The data depicted in FIG. 9 shows that in DM1 cells which expressed 60% of total transcripts with the foetal form (exon 7+), treatment with the compounds reduces inclusion of exon 7 to about 45% of total transcripts. Overall, these results show that the compounds can correct some of the molecular defects in DM1 patient cells.

EXAMPLE 8

Further Testing of Compounds in the Alternative Splicing Assay

DM1 patient myoblasts were treated for 7 days with a 20 µM concentration of each compound. Total RNA was extracted, and used in RT-PCR reactions to quantify the alternative splicing of exon 7 of MBNL2 and MBNL1 mRNAs, and exon 22 of Sercal mRNA, which are all mis-spliced to re-express a foetal or neonatal form in DM1 cells (Charizanis et al. 2012, Kimura et al. 2005). With the exception of analogue 31 (which exhibits cellular toxicity), all the analogues partially corrected the mis-splicing of MBNL2 and MBNL1 mRNA (FIG. 10). However, beside compound 15, most of these analogues had little effect on the mis-splicing of exon 22 of Sercal mRNA.

The other analogues of compounds 15 and 32 (FIG. 6C) were tested in splicing assays to measure alternative splicing correction of MBNL2, MBNL1 and Sercal pre-mRNAs in DM1. Mis-splicing of exon 5 of cardiac Troponin T (TNNT2/cTNT), which causes cardiac conduction defects in DM1 (Ho et al. 2005, Warf et al. 2009), was also tested. Analogues which corrected splicing of at least 3 control pre-mRNAs above 5% were considered active. As shown in FIG. 11, analogues 102, 196, and 214 were able to correct at least 3 mis-splicing of the pre-mRNAs tested. Depending on the mRNA tested, analogue 196 (which is a "chimera" of compounds 15 and 32) is either better or comparable to the original compound 15, since it significantly corrects mis-splicing of all the pre-mRNAs tested.

EXAMPLE 9

Dose-response, Specificity and Toxicity of the Compounds

Figure 12A:
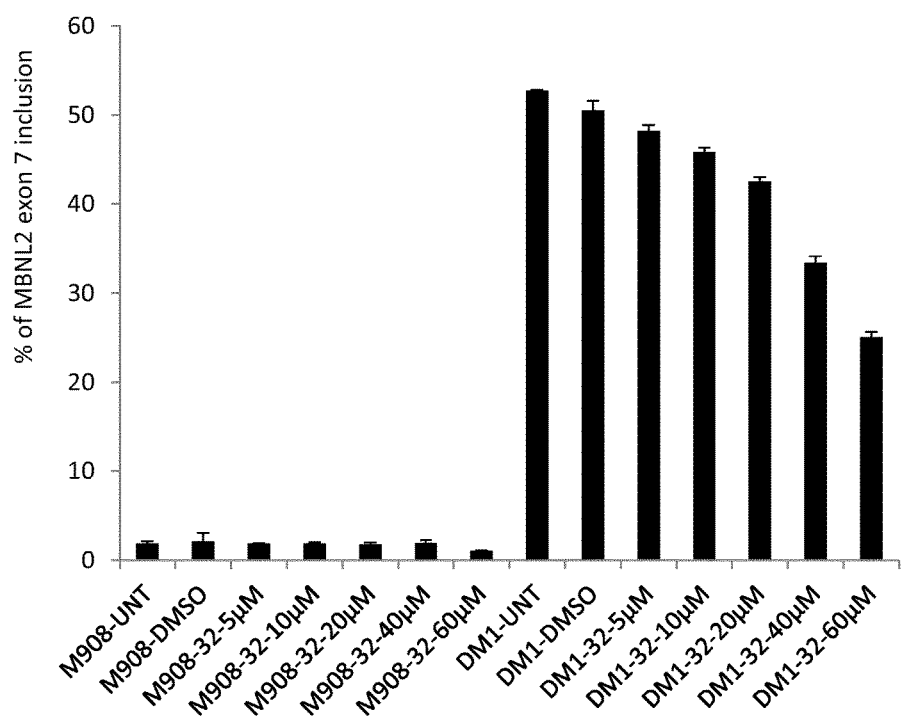
FIGS. 12A and 12B shows a dose-response effect of compound 32 on the splicing of exon 7 of MBNL2 mRNA (FIG. 12A) and exon 7 of MBNL1 mRNA (FIG. 12B) in normal (M908) or DM1 myoblasts (DM1). UNT: untreated cells. All the values were obtained from the average of 3 independent experiments.
Figure 12B:
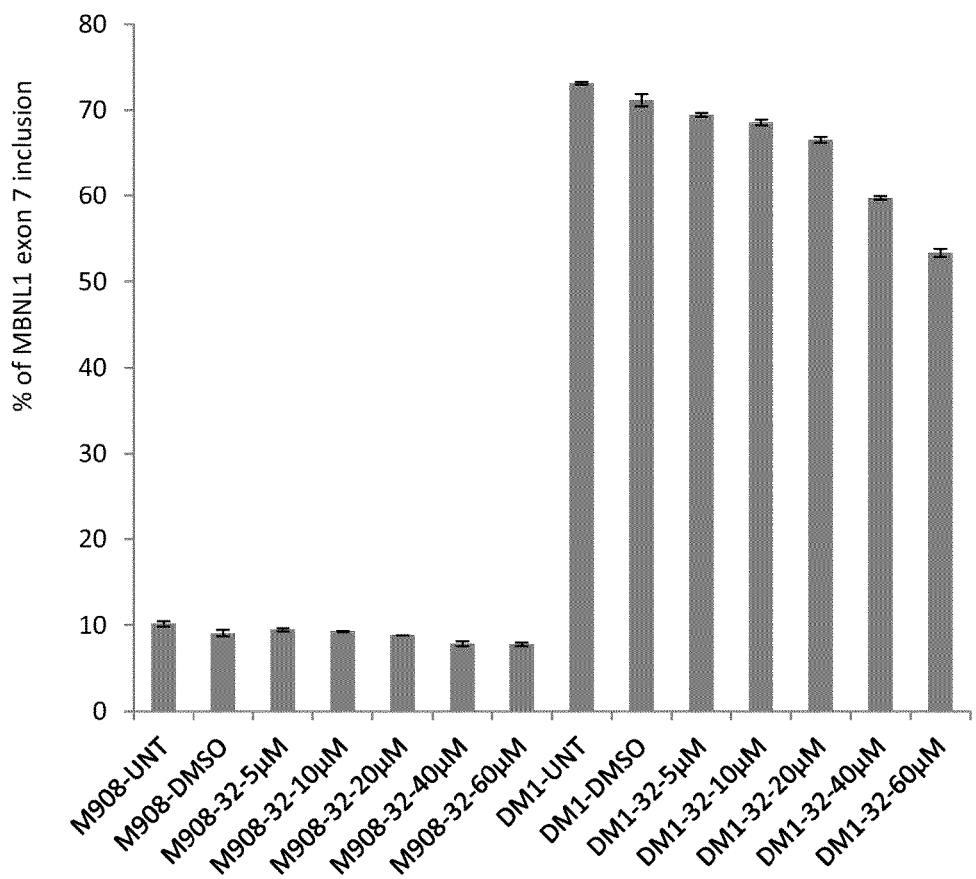

To determine if the identified compounds act as true pharmacological inhibitors, a dose-response assay was performed with the alternative splicing assay using compound 32. Normal (M908) and patient (DM1) myoblasts were treated for 7 days with compound 32 at concentrations varying from 5 to 60 µM. Total RNA was extracted, and used in RT-PCR reactions to quantify the alternative splicing of the endogenous MBNL2 and MBNL1 mRNAs. As shown in FIGS. 12A and 12B, a clear dose-response effect can be observed on the splicing of MBNL2 (FIG. 12A) and MBNL1 (FIG. 12B) mRNAs upon treatment of DM1 myoblasts, as the splicing pattern of both mRNAs shift toward the pattern observed in normal myoblasts as the concentration of compound 32 increases.

Figure 13:
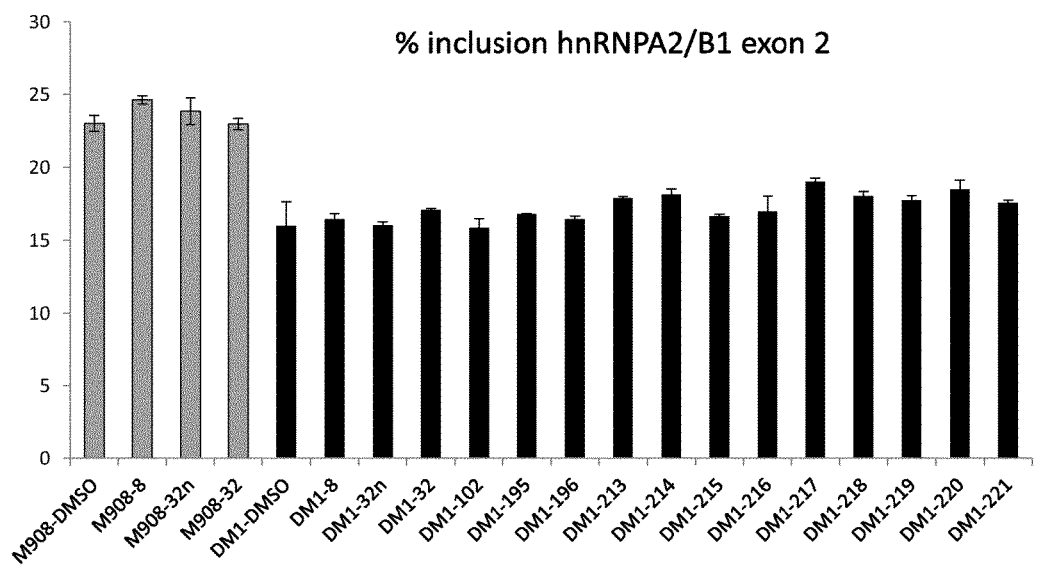
FIG. 13 shows the effect of various analogues of compounds 15 and 32 on the alternative splicing of the exon 2 of hnRNPA2/B1 mRNA, which is not mis-spliced in DM1 myoblasts. M908: normal myoblasts; DM1: DM1 patient myoblasts. All the values were obtained from the average of 3 independent experiments.

To eliminate the possibility that compounds 15 and 32 act as general regulators of splicing, the specificity of the two families of compounds was tested on the inclusion of exon 2 of the hnRNPA2/B1 pre-mRNA, which is not mis-spliced in DM1 patients (Philips et al., 1998). Normal (M908) and patient (DM1) myoblasts were treated for 7 days with a 20 µM concentration of the compounds. Total RNA was extracted, and used in RT-PCR reactions to quantify the splicing of the endogenous mRNA. As shown in FIG. 13, no significant change in exon 2 exclusion of the hnRNPA2/B1 pre-mRNA was observed between control (DMSO treated or inactive analogues) and cells treated with active compounds, for either normal or DM1 myoblasts. These results show that the compounds do not affect general splicing of pre-mRNAs, but act specifically on pre-mRNA mis-spliced in DM1.

The cellular toxicity of compounds 15 and 32, and their analogs was also measured using a validated cytotoxicity assay. Normal or DM1 myoblasts were treated with 20 µM of compound or DMSO. The ratio of viable cells was measured with a High Content Screening microscope in live cells treated with Hoescht 33342 (labels all cells) and propidium iodide (labels dead cells). The total number of cells was counted and the number of dead cells was subtracted to obtain the number of viable cells, which is presented as a ratio (drug-treated versus DMSO-treated cells). The percentage of dead cells was also measured using propidium iodide. As shown in FIG. 10, while some compounds like 15 and 31 show some toxicity, other compounds like 32 and 46 had little toxicity on the cells at this concentration.

Figure 14A:
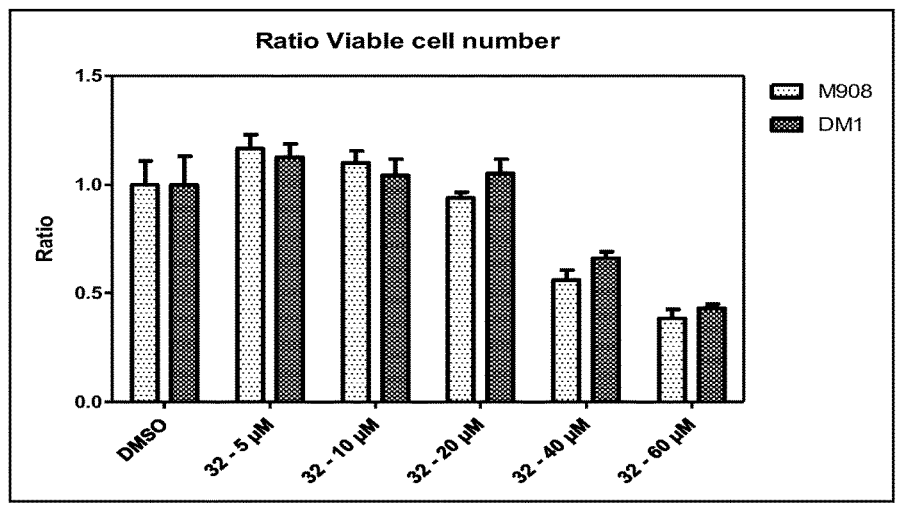
FIGS. 14A-D shows a dose-response assay of compounds 32 (FIGS. 14A-B) and 196 (FIGS. 14C-D) on the ratio of viable cell number and the percentage (%) of cell death. Both normal (M908) and DM1 myoblasts (DM1) were treated for 7 days at concentrations varying from 5 to 60 μM.
Figure 14B:
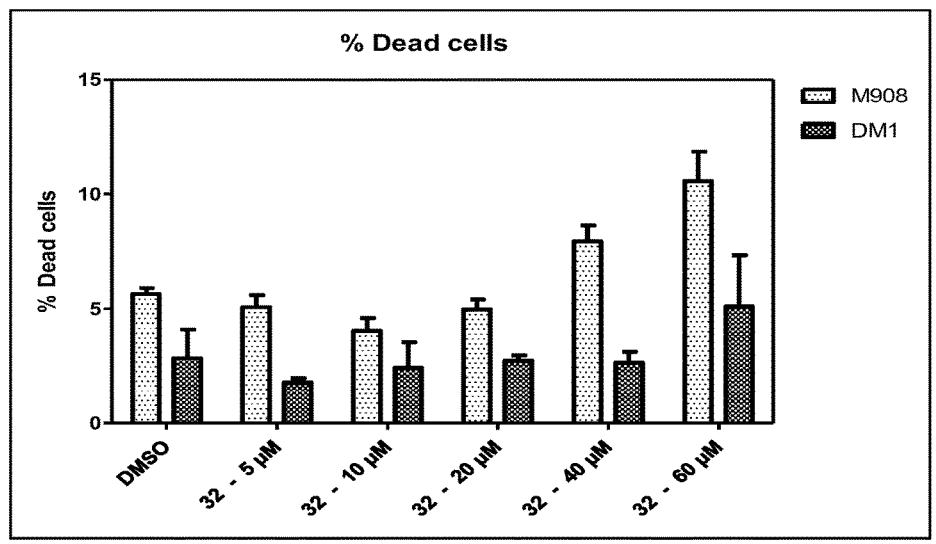
Figure 14C:
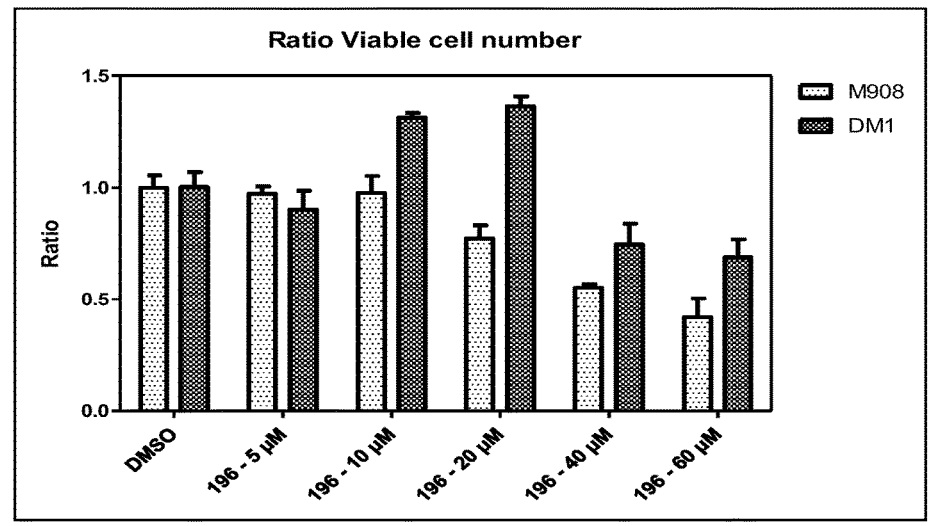
Figure 14D:
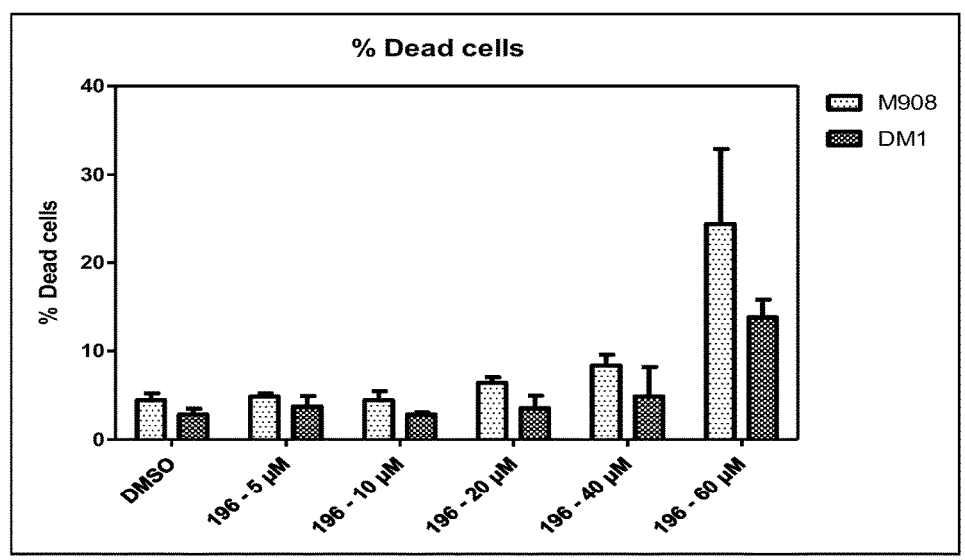

The cellular toxicity of the compounds was also measured in a dose-response assay. In this assay, normal (M908) and patient (DM1) myoblasts were treated for 7 days with compound 32 or 196 at concentrations varying from 5 to 60 µM. Cell number and cell death was quantified by High Content Screening microscope, as specified above. For both compounds, little cytotoxicity was observed at concentration of 20 µM and below (FIGS. 14A-D). The main phenotype observed was a cytostatic effect at higher concentrations, as cell death remains below 10% at concentrations lower than 60 µM. These results also show that some of the novel analogues were less toxic than the original compounds 15 and 32. Indeed, the ratio of viable cells at 20 µM of compound 15 is 0.22 (FIG. 10), while for compound 196, an analogue of compound 15, it is above 1 at the same concentration (FIG. 14C).

Although the present invention has been described hereinabove by way of specific embodiments thereof, it can be modified, without departing from the nature of the subject invention as defined in the appended claims. In the claims, the word "comprising" is used as an open-ended term, substantially equivalent to the phrase "including, but not limited to". The singular forms "a", "an" and "the" include corresponding plural references unless the context clearly dictates otherwise.

REFERENCES

1. Brook, J. D., McCurrach, M. E., Harley, H. G., Buckler, A. J., Church, D., Aburatani, H., Hunter, K., Stanton, V. P., Thirion, J. P., Hudson, T. et al. (1992). Molecular basis of myotonic dystrophy: expansion of a trinucleotide (CTG) repeat at the 3' end of a transcript encoding a protein kinase family member. Cell 68, 799-808.
2. Buxton, J., Shelbourne, P., Davies, J., Jones, C., Van Tongeren, T., Aslanidis, C., de Jong, P., Jansen, G., Anvret, M., Riley, B. et al. (1992). Detection of an unstable fragment of DNA specific to individuals with myotonic dystrophy. Nature 355, 547-548.
3. Charizanis K., Lee K. Y., Batra R., Goodwin M., Zhang C., Yuan Y., Shiue L., Cline M., Scotti M. M., Xia G. et al. (2012). Muscleblind-like 2-mediated alternative splicing in the developing brain and dysregulation in Myotonic Dystrophy. Neuron 75: 437-50.
4. Daughters, R. S., Tuttle, D. L., Gao, W., Ikeda, Y., Moseley, M. L., Ebner, T. J., Swanson, M. S. and Ranum, L. P. W. (2009). RNA gain-of-function in spinocerebellar ataxia type 8. PLoS Genet. 5, e1000600.
5. Davis, B. M., McCurrach, M. E., Taneja, K. L., Singer, R. H., and Housman, D. E. (1997) Expansion of a CUG trinucleotide repeat in the 3' untranslated region of myotonic dystrophy protein kinase transcripts results in nuclear retention of transcripts PNAS 94: 7388-7393.
6. Fardaei, M., Larkin, K., Brook, J. D., and Hamshere, M. G. (2001). In vivo co-localisation of MBNL protein with DMPK expanded-repeat transcripts. Nucleic Acids Research. 29, 2766-2771.
7. Fu, Y. H., Pizzuti, A., Fenwick, R. G. Jr., King, J., Rajnarayan, S., Dunne, P. W., Dubel, J., Nasser, G. A., Ashizawa, T., de Jong, P., et al. (1992) An unstable triplet repeat in a gene related to myotonic muscular dystrophy. Science 255:1256-1258.
8. Goers, E. S., Purcell, J., Voelker, R. B., Gates, D. P., and Berglund, J. A. (2010). MBNL1 binds GC motifs embedded in pyrimidines to regulate alternative splicing. Nucleic Acids Research 38, 2467-2484.
9. Ho T. H., Bundman D., Armstrong D. L., Cooper T. A. (2005). Transgenic mice expressing CUG-BP1 reproduce splicing mis-regulation observed in myotonic dystrophy. Hum. Mol. Genet. 14:1539-47.
10. Kimura T., Nakamori M., Lueck J. D., Pouliquin P., Aoike F., Fujimura H., Dirksen R. T., Takahashi M. P., Dulhunty A. F., Sakoda S. (2005). Altered mRNA splicing of the skeletal muscle ryanodine receptor and sarcoplasmic/endoplasmic reticulum Ca2+-ATPase in myotonic dystrophy type 1. Hum. Mol. Genet. 14:2189-2200.
11. Kuyumcu-Martinez, N. M., Wang, G.-S., and Cooper, T. A. (2007) Increased Steady-State Levels of CUGBP1 in Myotonic Dystrophy 1 Are Due to PKC-Mediated Hyperphosphorylation. Molecular Cell 28, 68-78.
12. Liquori, C L et al., (2001). Myotonic dystrophy type 2 caused by a CCTG expansion in intron 1 of ZNF9. Science 293, 864-867.
13. Mahadevan, M., Tsilfidis, C., Sabourin, L., Shutler, G., Amemiya, C., Jansen, G., Neville, C., Narang, M., Barcelo, J., O'Hoy, K. et al. (1992). Myotonic dystrophy mutation: an unstable CTG repeat in the 3 untranslated region of the gene. Science 255, 1253-1255.
14. Ranum, L. P. W. and Cooper, T. A. (2006). RNA-mediated neuromuscular disorders. Annu. Rev. Neurosci. 29, 259-277
15. Rudnicki, D. D., Holmes, S. E., Lin, M. W., Thornton, C. A., Ross, C. A. and Margolis, R. L. (2007). Huntington's disease-like 2 is associated with CUG repeat-containing RNA foci. Ann. Neurol. 61, 272-282.
16. Tassone, F., Iwahashi, C. and Hagerman, P. J. (2004). FMR1 RNA within the intranuclear inclusions of fragile X-associated tremor/ataxia syndrome (FXTAS). RNA Biol. 1, 103-105
17. Warf M B, Diegel J V, von Hippel P H., Berglund J A. (2009). The protein factors MBNL1 and U2AF65 bind alternative RNA structures to regulate splicing. Proc Natl Acad Sci USA. June 9; 106(23):9203-8.
18. Wheeler, T. M., Thornton, C. A. (2007) Myotonic dystrophy: RNA-mediated muscle disease. Curr. Opin. Neurol. 20, 572-576.
19. Wheeler, T. M. (2008) Myotonic Dystrophy: Therapeutic Strategies for the Future. Neurotherapeutics 5, 592-600.
20. Philips, Anne V., Timchenko, Lubov T., and Cooper, Thomas A., Disruption of Splicing Regulated by a CUG-Binding Protein in Myotonic Dystrophy. *Science* 280 (5364), 737 (1998).

What is claimed is:

1. A method for treating myotonic dystrophy type 1, said method comprising administering to a subject in need thereof an effective amount of at least one of the following compounds:

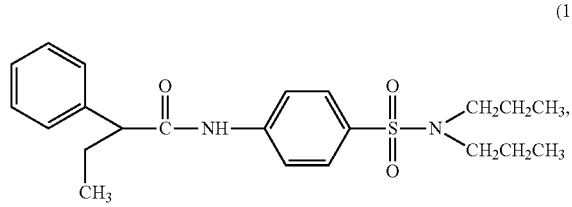

(15)

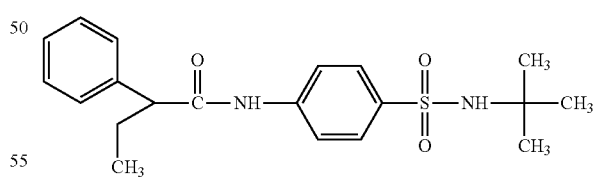

(8)

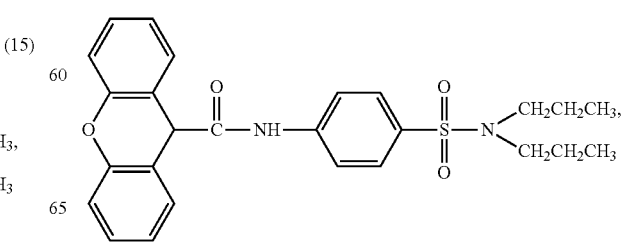

(12)

(19) 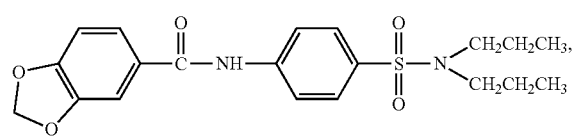
(32n) 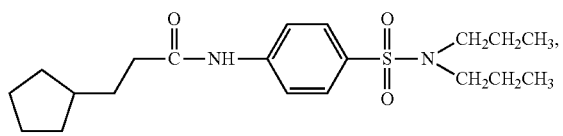
(21) 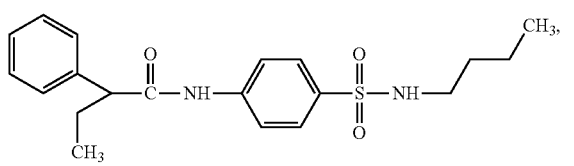
(22) 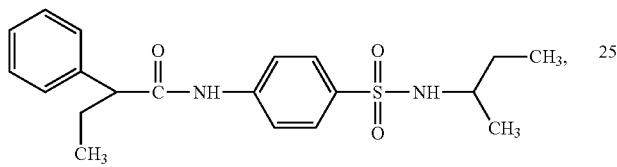
(27) 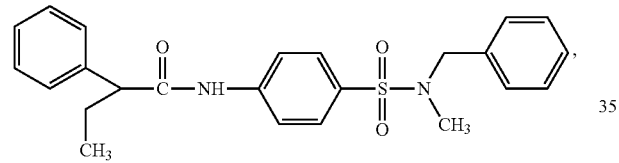
(23) 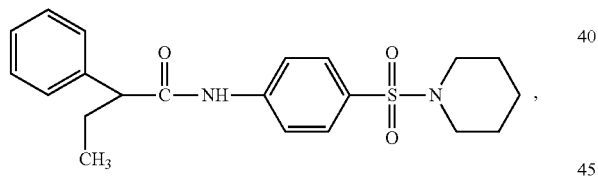
(28) 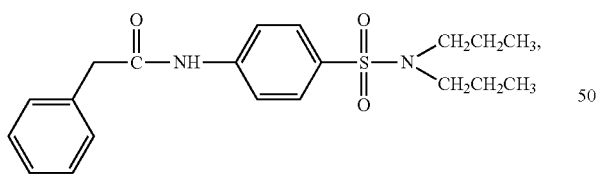
(29) 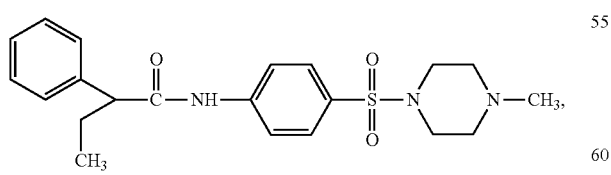
(34) 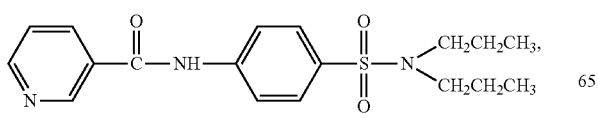
(24) 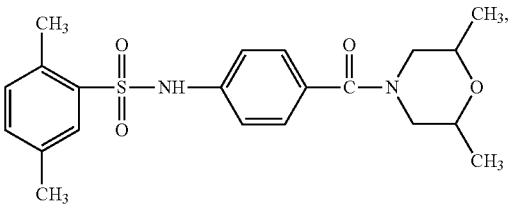
(32) 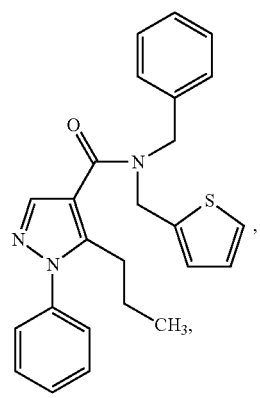
(43) 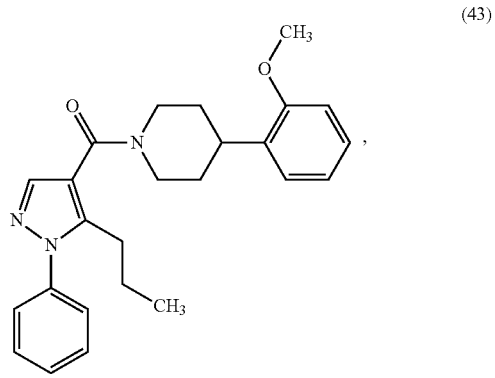
(46) 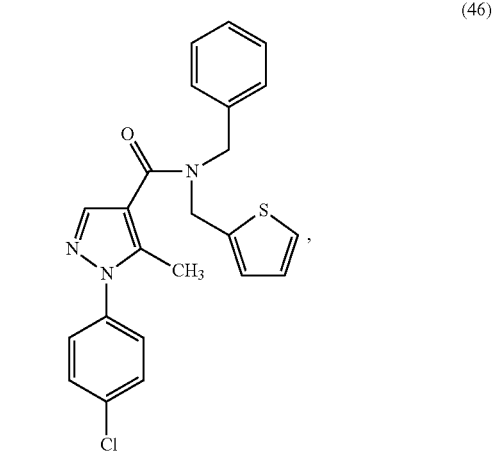

-continued (102)
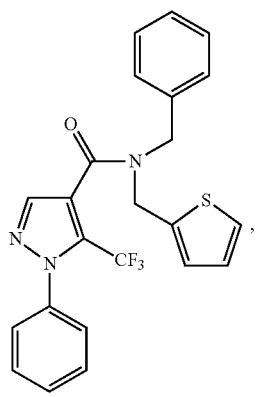

(196)
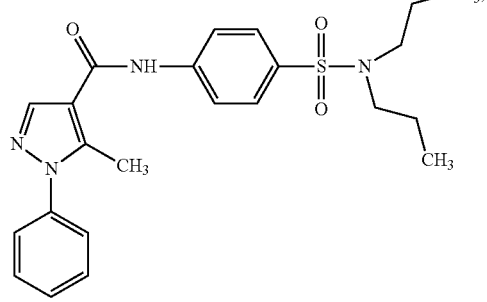

(214)
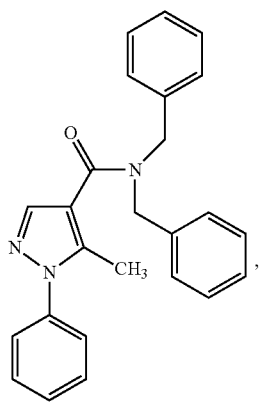

(220)
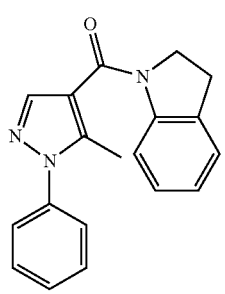

or a pharmaceutically acceptable salt thereof.

2. The method of claim 1, wherein said compound or pharmaceutically acceptable salt thereof is:

(15)
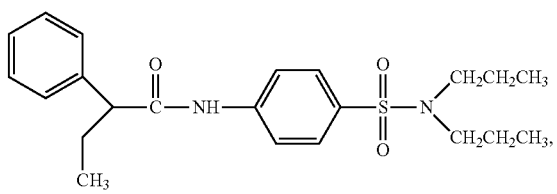

or a pharmaceutically acceptable salt thereof.

3. The method of claim 1, wherein said compound or pharmaceutically acceptable salt thereof is comprised in a composition further comprising a pharmaceutically acceptable carrier.

4. The method of claim 1, wherein said compound or pharmaceutically acceptable salt thereof is:

(8)
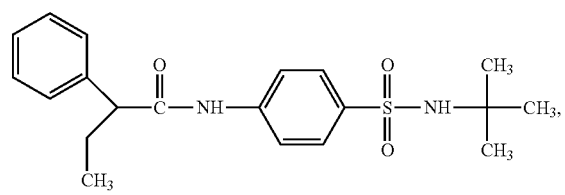

or a pharmaceutically acceptable salt thereof.

5. The method of claim 1, wherein said compound or pharmaceutically acceptable salt thereof is:

(12)

or a pharmaceutically acceptable salt thereof.

6. The method of claim 1, wherein said compound or pharmaceutically acceptable salt thereof is:

(19)

or a pharmaceutically acceptable salt thereof.

7. The method of claim 1, wherein said compound or pharmaceutically acceptable salt thereof is:

(21)

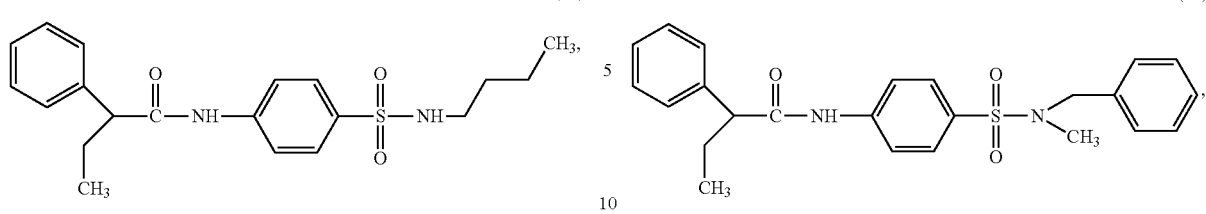

or a pharmaceutically acceptable salt thereof.

8. The method of claim 1, wherein said compound or pharmaceutically acceptable salt thereof is:

(22)

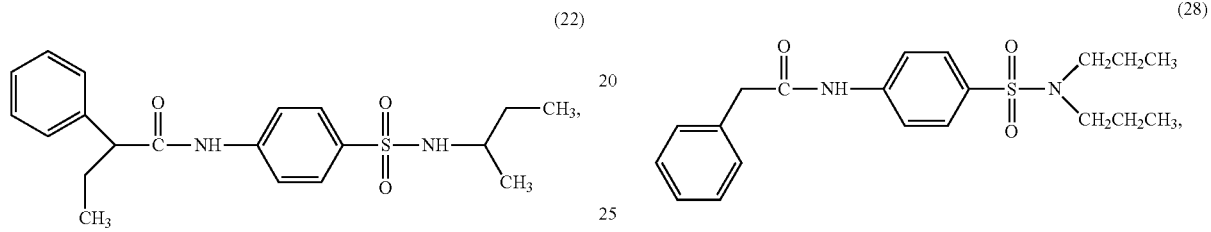

or a pharmaceutically acceptable salt thereof.

9. The method of claim 1, wherein said compound or pharmaceutically acceptable salt thereof is:

(23)

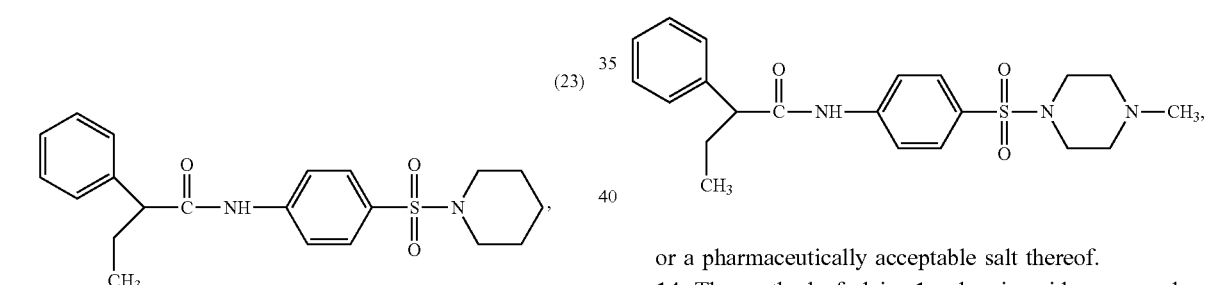

or a pharmaceutically acceptable salt thereof.

10. The method of claim 1, wherein said compound or pharmaceutically acceptable salt thereof is:

(24)

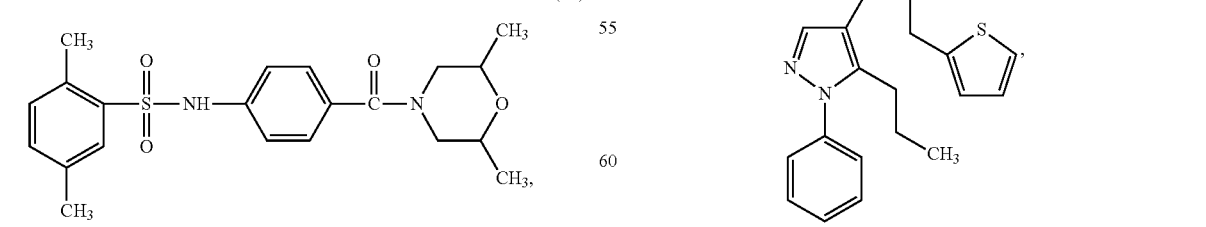

or a pharmaceutically acceptable salt thereof.

11. The method of claim 1, wherein said compound or pharmaceutically acceptable salt thereof is:

(27)

or a pharmaceutically acceptable salt thereof.

12. The method of claim 1, wherein said compound or pharmaceutically acceptable salt thereof is:

(28)

or a pharmaceutically acceptable salt thereof.

13. The method of claim 1, wherein said compound or pharmaceutically acceptable salt thereof is:

(29)

or a pharmaceutically acceptable salt thereof.

14. The method of claim 1, wherein said compound or pharmaceutically acceptable salt thereof is:

(32)

or a pharmaceutically acceptable salt thereof.

15. The method of claim 1, wherein said compound or pharmaceutically acceptable salt thereof is:

(32n)

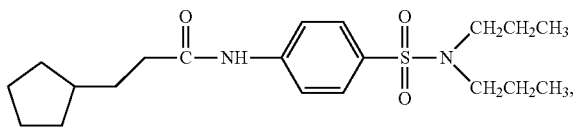

or a pharmaceutically acceptable salt thereof.

16. The method of claim 1, wherein said compound or pharmaceutically acceptable salt thereof is:

(34)

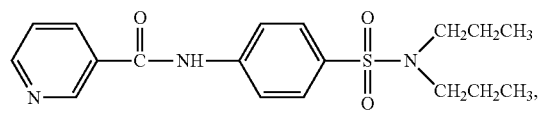

or a pharmaceutically acceptable salt thereof.

17. The method of claim 1, wherein said compound or pharmaceutically acceptable salt thereof is:

(43)

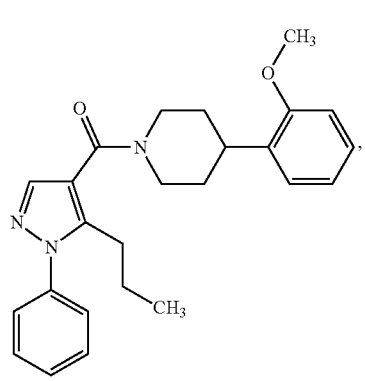

or a pharmaceutically acceptable salt thereof.

18. The method of claim 1, wherein said compound or pharmaceutically acceptable salt thereof is:

(46)

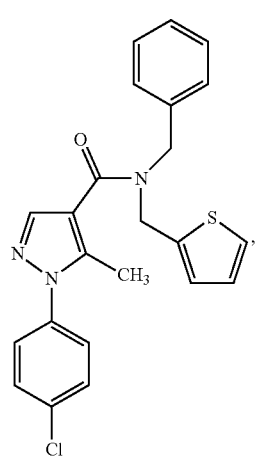

or a pharmaceutically acceptable salt thereof.

19. The method of claim 1, wherein said compound or pharmaceutically acceptable salt thereof is:

(102)

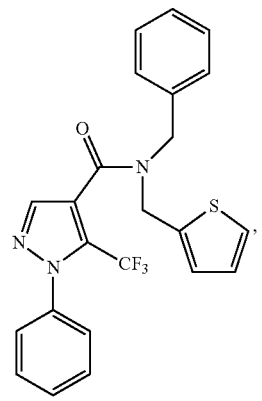

or a pharmaceutically acceptable salt thereof.

20. The method of claim 1, wherein said compound or pharmaceutically acceptable salt thereof is:

(196)

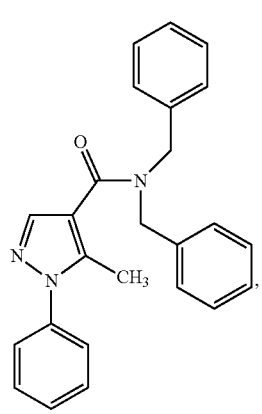

or a pharmaceutically acceptable salt thereof.

21. The method of claim 1, wherein said compound or pharmaceutically acceptable salt thereof is:

(214)

or a pharmaceutically acceptable salt thereof.

22. The method of claim 1, wherein said compound or pharmaceutically acceptable salt thereof is:

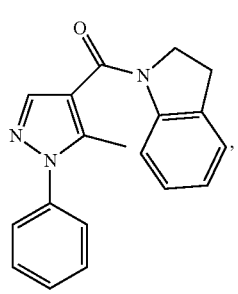
(220)
or a pharmaceutically acceptable salt thereof.
* * * * *